(12) United States Patent
Peralta-Yahya et al.

(10) Patent No.: US 9,809,862 B2
(45) Date of Patent: Nov. 7, 2017

(54) G-PROTEIN COUPLED RECEPTOR (GPCR)-BASED BIOSENSORS AND USES THEREOF

(71) Applicant: Georgia Tech Research Corporation, Atlanta, GA (US)

(72) Inventors: Pamela Peralta-Yahya, Atlanta, GA (US); Kuntal Mukherjee, Atlanta, GA (US); Souryadeep Bhattacharyya, Atlanta, GA (US); Stephen Sarria, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 14/823,317

(22) Filed: Aug. 11, 2015

(65) Prior Publication Data
US 2016/0122832 A1 May 5, 2016

Related U.S. Application Data

(60) Provisional application No. 62/035,734, filed on Aug. 11, 2014.

(51) Int. Cl.
| | |
|---|---|
| *C12Q 1/68* | (2006.01) |
| *G01N 33/92* | (2006.01) |
| *C12N 15/81* | (2006.01) |
| *G01N 33/58* | (2006.01) |
| *G01N 33/74* | (2006.01) |

(52) U.S. Cl.
CPC ............ *C12Q 1/6897* (2013.01); *C12N 15/81* (2013.01); *G01N 33/582* (2013.01); *G01N 33/74* (2013.01); *G01N 33/92* (2013.01); *G01N 2333/726* (2013.01)

(58) Field of Classification Search
None
See application file for complete search history.

(56) References Cited

U.S. PATENT DOCUMENTS

| | | | | |
|---|---|---|---|---|
| 5,576,210 A * | 11/1996 | Sledziewski | ......... | C07K 14/705 435/252.3 |
| 6,406,871 B1 * | 6/2002 | Pausch | ................ | C07K 14/723 435/254.2 |
| 6,509,447 B1 * | 1/2003 | Brown | ............... | C07K 14/4722 435/254.2 |
| 6,864,060 B1 * | 3/2005 | Fowlkes | .............. | C07K 14/395 435/254.2 |
| 2003/0108999 A1 * | 6/2003 | Manfredi | ............. | C07K 14/723 435/69.1 |

OTHER PUBLICATIONS

Minic et al., Functional expression of olfactory receptors in yeast and development of a bioassay for odorant screening, Jan. 2005, FEBS Journal 272(2):524-537.*
Mukherjee, et al., GPCR-Based Chemical Biosensors for Medium-Chain Fatty Acids, May 20, 2015, ACS Synth. Biol. 4:1261-1269.*
Charlier et al., How broadly tuned olfactory receptors equally recognize their agonists. Human OR1G1 as a test case, 2012, Cell. Mol. Life Sci. 69:4205-4213.*
Hagen et al., Pheromone Response Elements Are Necessary and Sufficient for Basal and Pheromone-Induced Transcription of the FUS1 Gene of *Saccharomyces cerevisiae*, Jun. 1991, Molecular and Cellular Biology 11(6): p. 2952-2961.*
Nehlin, J. O., Carlberg, M. & Ronne, H. Control of Yeast Gal Genes by Mig1 Repressor—a Transcriptional Cascade in he Glucose Response. Embo J 10, 3373-3377, (1991).
Erlenbach, I. et al. Functional expression of M-1, M-3 and M-5 muscarinic acetylcholine receptors in yeast. J Neurochem 77, 1327-1337, (2001).
Stewart, G. D., Sexton, P. M. & Christopoulos, A. Detection of Novel Functional Selectivity at M-3 Muscarinic Acetylcholine Receptors Using a *Saccharomyces cerevisiae* Platform. ACS Chem Biol 5, 365-375, (2010).
Wang, B. J. & Buck, M. Customizing cell signaling using engineered genetic logic circuits. Trends in microbiology 20, 376-384, (2012).
Moon, T. S., Lou, C. B., Tamsir, A., Stanton, B. C. & Voigt, C. A. Genetic programs constructed from layered logic fates in single cells. Nature 491, 249-253, (2012).
Win, M. N. & Smolke, C. D. Higher-order cellular information processing with synthetic RNA devices. Science 322, 456-460, (2008).
Dueber, J. E., Yeh, B. J., Chak, K. & Lim, W. A. Reprogramming control of an allosteric signaling switch through modular recombination. Science 301, 1904-1908, (2003).
Tabor, J. J., Levskaya, A. & Voigt, C. A. Multichromatic Control of Gene Expression in *Escherichia coli*. Journal of molecular biology 405, 315-324, (2011).
Giaever, G. et al. Functional profiling of the *Saccharomyces cerevisiae* genome. Nature 418, 387-391, (2002).
Baba, T. et al. Construction of *Escherichia coli* K-12 in-frame, single-gene knockout mutants: the Keio collection. Mol Syst Biol 2, (2006): 1-11.
Storici, F., Lewis, L. K. & Resnick, M. A. In vivo site-directed mutagenesis using oligonucleotides. Nature biotechnology 19, 773-776, (2001).
Stuckey, S. & Storid, F. Gene Knockouts, in vivo Site-Directed Mutagenesis and Other Modifications Using the Delitto Perfetto System in *Saccharomyces cerevisiae*. Method Enzymol 533, 103-131, (2013).
Wang, H. H., Kim, H., Cong, L., Jeong, J., Bang, D., and Church, G. M. (2012) Genome-scale promoter engineering by coselection MAGE, Nat Methods 9, 591-593.
Okumoto, S. (2012) Quantitative imaging using genetically encoded sensors for small molecules in plants. Plant J 70, 108-117.
Ostermeier, M. (2005) Engineering allosteric protein switches by domain insertion. Protein Eng Des Sel 18, 359-364.
O'Malley, et al., (2009) Progress toward heterologous expression of active G-protein-coupled receptors in *Saccharomyces cerevisiae*: Linking cellular stress response with translocation and trafficking. Prot Sci 18, 2356-2370.

(Continued)

*Primary Examiner* — John Ulm
(74) *Attorney, Agent, or Firm* — Thomas|Horstemeyer, LLP

(57) ABSTRACT

Provided herein are GPCR-based chemical biosensors that can have a sensing unit, a processing unit, and a response unit that can be used to detect a chemical of interest. Also provided herein are methods of making and using the GPCR-based chemical biosensors.

20 Claims, 31 Drawing Sheets

(56) References Cited

OTHER PUBLICATIONS

Emmerstorfer, A., Wriessnegger, T., Hirz, M. & Pichler, H. (2014) Overexpression of membrane proteins from higher eukaryotes in yeasts. Appl Microbiol Biotechnol 98, 7671-7698.

Fukutani, Y., et al., (2015) Improving the odorant sensitivity of olfactory receptor-expressing yeast with accessory proteins. Anal Biochem 471, 1-8.

Knothe, G. (2009) Improving biodiesel fuel properties by modifying fatty ester composition, Energ Environ Sci 2, 759-766.

Knothe, G. (2014) A comprehensive evaluation of the cetane numbers of fatty acid methyl esters. Fuel 119, 6-13.

Leber, C., and Da Silva, N. A. (2014) Engineering of *Saccharomyces cerevisiae* for the Synthesis of Short Chain Fatty Acids, Biotechnol Bioeng 111, 347-358.

Torella, J. P., Ford, T. J., Kim, S. N., Chen, A. M., Way, J. C., and Silver, P. A. (2013) Tailored fatty acid synthesis via dynamic control of fatty acid elongation, Proc Natl Acad Sci USA 110, 11290-11295.

Choi, Y. J., and Lee, S. Y. (2013) Microbial production of short-chain alkanes, Nature 502, 571-574.

Zhang, F. Z. Ouellet, M. Batth, T. S. Adams, P. D., Petzold, C. J., Mukhopadhyay, A., and Keasling, J. D. (2012) Enhancing fatty acid production by the expression of the regulatory transcription factor FadR, Metab Eng 14, 653-660.

Runguphan, W., and Keasling, J. D. (2014) Metabolic engineering of *Saccharomyces cerevisiae* for production of fatty acid-derived biofuels and chemicals, Metab Eng 21, 103-113.

Brown, et al. (2000) Functional coupling of mammalian receptors to the yeast mating pathway using novel yeast/mammalian G protein alpha-subunit chimeras. Yeast 16, 11-22.

Golemis, E. A., and Brent, R. (1992) Fused Protein Domains Inhibit DNA-Binding by Lexa, Mol Cell Biol 12, 3006-3014.

Peralta-Yahya, P., Carter, B. T., Lin, H. N., Tao, H. Y., and Cornish, V. W. (2008) High-Throughput Selection for Cellulase Catalysts Using Chemical Complementation, J Am Chem Soc 130, 17446-17452.

Mukherjee, et al., GPCR-Based Chemical Biosensors for Medium-Chain Fatty Acids, ACS Synthetic Biology, Am Chem Soc, 2014: 1261-1269.

Shcherbo D., et al. Biochem. J. 2009, 418, 567-574.

Shaner NC, et al. Nat. Biotechnol. 2004, 22, 1567-72.

Khmelinskii A, et al. Nat. Biotechnol. 2012, 30, 708-14.

Ball, David A., et al. PloS ONE 2014, 9, e107087.

Bniegowski, J.A. et al. Biochem. Biophys. Res. Commun. 2005, 332, 657-663.

Keasling, J. D. Manufacturing molecules through metabolic engineering. Science 330, 1355-1358, (2010).

Peralta-Yahya, P. P., Zhang, F. Z., del Cardayre, S. B. & Keasling, J. D. Microbial engineering for the production of advanced biofuels. Nature 488, 320-328, (2012).

Pine, C. M., De Mey, M., Prather, K. L. J. & Ajikumar, P. K. Integrating the Protein and Metabolic Engineering Toolkits for Next-Generation Chemical Biosynthesis. ACS Chem Biol 8, 662-672, (2013).

Mardis, E. R. Next-Generation Sequencing Platforms. Annu Rev Anal Chem 6, 287-303, (2013).

Caspi, R. et al. The MetaCyc database of metabolic pathways and enzymes and the BioCyc collection of Pathway/Genome Databases. Nucleic acids research 42, D459-D471, (2014).

Hillson, N. J., Rosengarten, R. D. & Keasling, J. D. j5 DNA assembly design automation software. ACS synthetic biology 1, 14-21, (2012).

Bilitchenko, L. et al. Eugene—A Domain Specific Language for Specifying and Constraining Synthetic Biological Parts, Devices, and Systems. PloS one 6, (2011): 1-12.

Lu, G. & Moriyama, E. N. Vector NTI, a balanced all-in-one sequence analysis suite. Briefings in bioinformatics 5, 378-388, (2004).

Wetterstrand, K. A. DNA sequencing costs: data from the NHGRI large-scale genome sequencing program. National human Research Project http://www.genome.gov/sequencingcosts, (2011): 1-4.

de Kok, S. et al. Rapid and reliable DNA assembly via ligase cycling reaction. ACS synthetic biology 3, 97-106, (2014).

Gibson, D. G. et al. Enzymatic assembly of DNA molecules up to several hundred kilobases. Nature methods 6, 343-345, (2009).

Li, M. Z. & Elledge, S. J. Harnessing homologous recombination in vitro to generate recombinant DNA via SLIC. Nature methods 4, 251-256, (2007).

Wang, H. H. et al. Programming cells by multiplex genome engineering and accelerated evolution. Nature 460, 894-U133, (2009).

Greenspan, P., Mayer, E. P. & Fowler, S. D. Nile Red—a Selective Fluorescent Stain for Intracellular Lipid Droplets. J Cell Biol 100, 965-973, (1985).

Xu, P. et al. Modular optimization of multi-gene pathways for fatty acids production in *E. coli*. Nature communications 4, (2013): 1-8.

Michener, J. K., Thodey, K., Liang, J. C. & Smolke, C. D. Applications of genetically-encoded biosensors for the construction and control of biosynthetic pathways. Metabolic engineering 14, 212-222, (2012).

Dietrich, J. A., Shis, D. L., Alikhani, A. & Keasling, J. D. Transcription factor-based screens and synthetic selections for microbial small-molecule biosynthesis. ACS synthetic biology 2, 47-58, (2013).

Lynch, S. A. & Gallivan, J. P. A flow cytometry-based screen for synthetic riboswitches. Nucleic acids research 37, 184-192, (2009).

Schwimmer, L. J., Rohatgi, P., Azizi, B., Seley, K. L & Doyle, D. F. Creation and discovery of ligand-receptor pairs for transcriptional control with small molecules. Proceedings of the National Academy of Sciences of the United States of America 101, 14707-14712, (2004).

McLachlan, M. J., Chockalingam, K., Lai, K. C. & Zhao, H. M. Directed Evolution of Orthogonal Ligand Specificity in a Single Scaffold. Angew Chem Int Edit 48, 7783-7786, (2009).

Yang, J. et al. Synthetic RNA devices to expedite the evolution of metabolite-producing microbes. Nature communications 4, 1413, (2013): 1-7.

Tang, S. Y. et al. Screening for Enhanced Triacetic Acid Lactone Production by Recombinant *Escherichia coli* Expressing a Designed Triacetic Acid Lactone Reporter. Journal of the American Chemical Society 135, 10099-10103, (2013).

Win, M. N. & Smolke, C. D. A modular and extensible RNA-based gene-regulatory platform for engineering cellular function. Proceedings of the National Academy of Sciences of the United States of America 104, 14283-14288, (2007).

Abril, M. A., Michan, C., Timmis, K. N. & Ramos, J. L. Regulator and Enzyme Specificities of the Tol Plasmid-Encoded Upper Pathway for Degradation of Aromatic-Hydrocarbons and Expansion of the Substrate Range of the Pathway. J Bacteriol 171, 6782-6790, (1989).

Zhang, F. Z. & Keasling, J. Biosensors and their applications in microbial metabolic engineering. Trends Microbiol 19, 323-329, (2011).

Ninfa, A. J. Use of two-component signal transduction systems in the construction of synthetic genetic networks. Curr Opin Microbiol 13, 240-245, (2010).

Wolanin, P. M., Thomason, P. A. & Stock, J. B. Histidine protein kinases: key signal transducers outside the animal kingdom. Genome biology 3, (2002): 1-8.

Granier, S. & Kobilka, B. A new era of GPCR structural and chemical biology. Nature chemical biology 8, 670-673, (2012).

Siehler, S. Cell-based assays in GPCR drug discovery. Biotechnology journal 3, 471-483, (2008).

Kue, C. Y. Hsueh, Y. P. & Heitman, J. Magnificent seven: roles of G protein-coupled receptors in extracellular sensing in fungi. Fems Microbial Rev 32, 1010-1032, (2008).

Radhika, V. et al. Chemical sensing of DNT by engineered olfactory yeast strain. Nature chemical biology 3, 325-330, (2007).

Erickson, J. P. et al. Edg-2/Vzg-1 couples to the yeast pheromone response pathway selectively in response to lysophosphatidic acid. Journal of Biological Chemistry 273, 1506-1510, (1998).

Minic, J. et al. Functional expression of olfactory receptors in yeast and development of a bioassay for odorant screening. Febs Journal 272, 524-537, (2005).

(56) References Cited

OTHER PUBLICATIONS

King, K., Dahlman, H. G., Thorner, J., Caron, M. G. & Lefkowitz, R. J. Control of Yeast Mating Signal Transduction by a Mammalian Beta-2-Adrenergic Receptor and Gs Alpha-Subunit. Science 250, 121-123, (1990).

Versele, M., Lemaire, K. & Thevelein, J. M. Sex and sugar in yeast: two distinct GPCR systems. Embo Rep 2, 574-579, (2001).

Iguchi, Y. et al. Control of signalling properties of human somatostatin receptor subtype-5 by additional signal sequences on its amino-terminus in yeast. J Biochem 147, 875-884, (2010).

Price, L. A., Strnad, J., Pausch, M. H. & Hadcock, J. R. Pharmacological characterization of the rat A(2a) adenosine receptor functionally coupled to the yeast pheromone response pathway. Mol Pharmacol 50, 829-837, (1996).

Reilander, H. & Weiss, H. M. Production of G-protein-coupled receptors in yeast. Current opinion in biotechnology 9, 510-517, (1998).

Pausch, H. M. G-protein-coupled receptors in *Saccharomyces cerevisiae*: high-throughput screening assays for drug discovery. Trends in Biotechnology 15, 487-494, (1997).

Dong, S., Rogan, S. C. & Roth, B. L. Directed molecular evolution of DREADDs: a generic approach to creating next-generation RASSLs. Nature protocols 5, 561-573, (2010).

Armbruster, B. N., Li, X., Pausch, M. H., Herlitze, S. & Roth, B. L. Evolving the lock to fit the key to create a family of G protein-coupled receptors potently activated by an inert ligand. Proceedings of the National Academy of Sciences of the United States of America 104, 5163-5168, (2007).

Wess, J., Nakajima, K. & Jain, S. Novel designer receptors to probe GPCR signaling and physiology. Trends in pharmacological sciences 34, 385-392, (2013).

Conklin, B. R. et al. Engineering GPCR signaling pathways with RASSLs. Nature methods 5, 673-678, (2008).

Itoh, Y. et al. Free fatty acids regulate insulin secretion from pancreatic beta cells through GPR40. Nature 422, 173-176, (2003).

Sanz, G., Schlegel, C., Pemollet, J. C. & Briand, L. Comparison of odorant specificity of two human olfactory receptors from different phylogenetic classes and evidence for antagonism. Chemical senses 30, 69-80, (2005).

Roberts, C. J. et al. Signaling and circuitry of multiple MAPK pathways revealed by a matrix of global gene expression profiles. Science 287, 873-880, (2000).

Pi, H. W., Chien, C. T. & Fields, S. Transcriptional activation upon pheromone stimulation mediated by a small domain of *Saccharomyces cerevisiae* Ste12p. Mol Cell Biol 17, 6410-6418, (1997).

Lee, et al., Improved Blue, Green, and Red Fluorescent Protein Tagging Vectors for *S. cerevisiae*, PLOS ONE Jul. 2013, pp. 1-8.

* cited by examiner

SEQUENCE LISTING

<160> NUMBER OF SEQ ID NOS: 89

<210> SEQ ID NO 1
<211> LENGTH: 85
<212> TYPE: DNA
<213> ORGANISM: Artificial Sequence
<220> FEATURE:
<223> OTHER INFORMATION: primer KM1

<400> SEQUENCE: 1
gtctatagat ccactggaaa gcttcgtggg cgtaagaagg caatctatta tagggataac     60
agggtaattt cgtacgctgc aggtc                                          85

<210> SEQ ID NO 2
<211> LENGTH: 70
<212> TYPE: DNA
<213> ORGANISM: Artificial Sequence
<220> FEATURE:
<223> OTHER INFORMATION: KM2

<400> SEQUENCE: 2
aaaaaaggaa aagcaaaagc ctcgaaatac gggcctcgat tcccgaacta ccgcgcgttg     60
gccgattcat                                                           70

<210> SEQ ID NO 3
<211> LENGTH: 80
<212> TYPE: DNA
<213> ORGANISM: Artificial Sequence
<220> FEATURE:
<223> OTHER INFORMATION: primer KM7

<400> SEQUENCE: 3
ccactggaaa gcttcgtggg cgtaagaagg caatctatta tagttcggga atcgaggccc     60
gtatttcgag gcttttgctt                                                80

<210> SEQ ID NO 4
<211> LENGTH: 80
<212> TYPE: DNA
<213> ORGANISM: Artificial Sequence
<220> FEATURE:
<223> OTHER INFORMATION: primer KM8

<400> SEQUENCE: 4
aagcaaaagc ctcgaaatac gggcctcgat tcccgaacta atatagattg ccttcttacg     60
cccacgaagc tttccagtgg                                                80

<210> SEQ ID NO 5
<211> LENGTH: 88
<212> TYPE: DNA
<213> ORGANISM: Artificial Sequence
<220> FEATURE:
<223> OTHER INFORMATION: primer KM9

<400> SEQUENCE: 5
tatctgaggc gttataggtt caatttggta attaaagata gagttgtaag tagggataac     60
agggtaattt cgtacgctgc aggtcgac                                       88

<210> SEQ ID NO 6
<211> LENGTH: 70
<212> TYPE: DNA
<213> ORGANISM: Artificial Sequence
<220> FEATURE:
<223> OTHER INFORMATION: primer KM10

```
<400> SEQUENCE: 6
aggactgttt gtgcaattgt acctgaagat gagtaagact ctcaatgaaa ccgcgcgttg      60
gccgattcat                                                            70

<210> SEQ ID NO 7
<211> LENGTH: 80
<212> TYPE: DNA
<213> ORGANISM: Artificial Sequence
<220> FEATURE:
<223> OTHER INFORMATION: primer KM13

<400> SEQUENCE: 7
gttataggtt caatttggta attaaagata gagttgtaag tttcattgag agtcttactc      60
atcttcaggt acaattgcac                                                 80

<210> SEQ ID NO 8
<211> LENGTH: 80
<212> TYPE: DNA
<213> ORGANISM: Artificial Sequence
<220> FEATURE:
<223> OTHER INFORMATION: primer KM14

<400> SEQUENCE: 8
gtgcaattgt acctgaagat gagtaagact ctcaatgaaa cttacaactc tatctttaat      60
taccaaattg aacctataac                                                 80

<210> SEQ ID NO 9
<211> LENGTH: 46
<212> TYPE: DNA
<213> ORGANISM: Artificial Sequence
<220> FEATURE:
<223> OTHER INFORMATION: primer KM19

<400> SEQUENCE: 9
cgtcaaggag aaaaaacccc ggatccatgg tgagcaaggg cgagga                    46

<210> SEQ ID NO 10
<211> LENGTH: 46
<212> TYPE: DNA
<213> ORGANISM: Artificial Sequence
<220> FEATURE:
<223> OTHER INFORMATION: primer KM20

<400> SEQUENCE: 10
tcttagctag ccgcggtacc aagcttttac ttgtacagct cgtcca                    46

<210> SEQ ID NO 11
<211> LENGTH: 48
<212> TYPE: DNA
<213> ORGANISM: Artificial Sequence
<220> FEATURE:
<223> OTHER INFORMATION: KM15

<400> SEQUENCE: 11
tgtaatccat cgatactagt gcggccgcac gatgattcag ttcgcctt                  48

<210> SEQ ID NO 12
<211> LENGTH: 48
<212> TYPE: DNA
<213> ORGANISM: Artificial Sequence
<220> FEATURE:
<223> OTHER INFORMATION: primer KM23
```

<400> SEQUENCE: 12
tgtaatccat cgatactagt gcggccgctg tatatgagat agttgatt                48

<210> SEQ ID NO 13
<211> LENGTH: 40
<212> TYPE: DNA
<213> ORGANISM: Artificial Sequence
<220> FEATURE:
<223> OTHER INFORMATION: primer KM24

<400> SEQUENCE: 13
ttttgaagct atggtgtgtg atccttttgt tgtttccggg                          40

<210> SEQ ID NO 14
<211> LENGTH: 46
<212> TYPE: DNA
<213> ORGANISM: Artificial Sequence
<220> FEATURE:
<223> OTHER INFORMATION: primer KM27

<400> SEQUENCE: 14
cctatagtga gtcgtattac ggatcctttg taattaaaac ttagat                   46

<210> SEQ ID NO 15
<211> LENGTH: 20
<212> TYPE: DNA
<213> ORGANISM: Artificial Sequence
<220> FEATURE:
<223> OTHER INFORMATION: primer KM28

<400> SEQUENCE: 15
agctagccgc ggtaccaagc                                                20

<210> SEQ ID NO 16
<211> LENGTH: 48
<212> TYPE: DNA
<213> ORGANISM: Artificial Sequence
<220> FEATURE:
<223> OTHER INFORMATION: primer KM43

<400> SEQUENCE: 16
aatcaactat ctcatataca gcggccgcat gaagctactg tcttctat                 48

<210> SEQ ID NO 17
<211> LENGTH: 46
<212> TYPE: DNA
<213> ORGANISM: Artificial Sequence
<220> FEATURE:
<223> OTHER INFORMATION: primer KM44

<400> SEQUENCE: 17
catccttgta atccatcgat actagtttag aacccattat tgttgg                   46

<210> SEQ ID NO 18
<211> LENGTH: 70
<212> TYPE: DNA
<213> ORGANISM: Artificial Sequence
<220> FEATURE:
<223> OTHER INFORMATION: primer KM49

<400> SEQUENCE: 18
cttttatagc ggaaccgctt tctttatttg aattgtcttg ttcaccaagg atgggtaagg    60
aaaagactca                                                           70

```
<210> SEQ ID NO 19
<211> LENGTH: 70
<212> TYPE: DNA
<213> ORGANISM: Artificial Sequence
<220> FEATURE:
<223> OTHER INFORMATION: primer KM50

<400> SEQUENCE: 19
ctggcccgca tttttaattc ttgtatcata aattcaaaaa ttatattata ttagaaaaac    60
tcatcgagca                                                           70

<210> SEQ ID NO 20
<211> LENGTH: 48
<212> TYPE: DNA
<213> ORGANISM: Artificial Sequence
<220> FEATURE:
<223> OTHER INFORMATION: primer KM54

<400> SEQUENCE: 20
tgtaatccat cgatactagt gcggccgcat caccctgcat tgcctctt                 48

<210> SEQ ID NO 21
<211> LENGTH: 46
<212> TYPE: DNA
<213> ORGANISM: Artificial Sequence
<220> FEATURE:
<223> OTHER INFORMATION: primer KM55

<400> SEQUENCE: 21
tcctcgccct tgctcaccat ggatcctttt ttttttttt ttttgt                    46

<210> SEQ ID NO 22
<211> LENGTH: 46
<212> TYPE: DNA
<213> ORGANISM: Artificial Sequence
<220> FEATURE:
<223> OTHER INFORMATION: primer KM56

<400> SEQUENCE: 22
tcctcgccct tgctcaccat ggatcctttg attttcagaa acttga                   46

<210> SEQ ID NO 23
<211> LENGTH: 88
<212> TYPE: DNA
<213> ORGANISM: Artificial Sequence
<220> FEATURE:
<223> OTHER INFORMATION: KM59

<400> SEQUENCE: 23
aattggttac ttaaaaatgc accgttaaga accatatcca agaatcaaaa tagggataac    60
agggtaattt cgtacgctgc aggtcgac                                       88

<210> SEQ ID NO 24
<211> LENGTH: 70
<212> TYPE: DNA
<213> ORGANISM: Artificial Sequence
<220> FEATURE:
<223> OTHER INFORMATION: primer KM60

<400> SEQUENCE: 24
accttatacc gaaggtcacg aaattacttt ttcaaagccg taaattttga ccgcgcgttg    60
gccgattcat                                                           70

<210> SEQ ID NO 25
```

```
<211> LENGTH: 80
<212> TYPE: DNA
<213> ORGANISM: Artificial Sequence
<220> FEATURE:
<223> OTHER INFORMATION: primer KM61

<400> SEQUENCE: 25
ttaaaaatgc accgttaaga accatatcca agaatcaaaa tcaaaattta cggctttgaa    60
aaagtaattt cgtgaccttc                                                80

<210> SEQ ID NO 26
<211> LENGTH: 80
<212> TYPE: DNA
<213> ORGANISM: Artificial Sequence
<220> FEATURE:
<223> OTHER INFORMATION: primer KM62

<400> SEQUENCE: 26
gaaggtcacg aaattacttt ttcaaagccg taaattttga ttttgattct tggatatggt    60
tcttaacggt gcatttttaa                                                80

<210> SEQ ID NO 27
<211> LENGTH: 46
<212> TYPE: DNA
<213> ORGANISM: Artificial Sequence
<220> FEATURE:
<223> OTHER INFORMATION: primer KM159

<400> SEQUENCE: 27
tcgaggtcga cggtatcgat aagcttacga tgattcagtt cgcctt                   46

<210> SEQ ID NO 28
<211> LENGTH: 46
<212> TYPE: DNA
<213> ORGANISM: Artificial Sequence
<220> FEATURE:
<223> OTHER INFORMATION: primer KM160

<400> SEQUENCE: 28
gcggccgctc tagaactagt ggatcccttc gagcgtccca aaacct                   46

<210> SEQ ID NO 29
<211> LENGTH: 46
<212> TYPE: DNA
<213> ORGANISM: Artificial Sequence
<220> FEATURE:
<223> OTHER INFORMATION: primer KM185

<400> SEQUENCE: 29
cccccctcga ggtcgacggt atcgataagc ttatcaccct gcattg                   46

<210> SEQ ID NO 30
<211> LENGTH: 46
<212> TYPE: DNA
<213> ORGANISM: Artificial Sequence
<220> FEATURE:
<223> OTHER INFORMATION: primer KM186

<400> SEQUENCE: 30
cgcggtggcg gccgctctag aactagtgga tcccttcgag cgtccc                   46

<210> SEQ ID NO 31
<211> LENGTH: 46
<212> TYPE: DNA
<213> ORGANISM: Artificial Sequence
```

```
<220> FEATURE:
<223> OTHER INFORMATION: primer KM187

<400> SEQUENCE: 31
taatccatcg atactagtgc ggccgcccga gctcttacgc gggtcg        46

<210> SEQ ID NO 32
<211> LENGTH: 46
<212> TYPE: DNA
<213> ORGANISM: Artificial Sequence
<220> FEATURE:
<223> OTHER INFORMATION: primer KM188

<400> SEQUENCE: 32
tcctcgccct tgctcaccat ggatcctata taccctctag agtcga        46

<210> SEQ ID NO 33
<211> LENGTH: 46
<212> TYPE: DNA
<213> ORGANISM: Artificial Sequence
<220> FEATURE:
<223> OTHER INFORMATION: primer KM189

<400> SEQUENCE: 33
catccttgta atccatcgat actagtttag aacccattat tgttgg        46

<210> SEQ ID NO 34
<211> LENGTH: 46
<212> TYPE: DNA
<213> ORGANISM: Artificial Sequence
<220> FEATURE:
<223> OTHER INFORMATION: primer KM190

<400> SEQUENCE: 34
tcaactatct catatacagc ggccgcatga agctactgtc ttctat        46

<210> SEQ ID NO 35
<211> LENGTH: 46
<212> TYPE: DNA
<213> ORGANISM: Artificial Sequence
<220> FEATURE:
<223> OTHER INFORMATION: KM191

<400> SEQUENCE: 35
catccttgta atccatcgat actagttcac aacaattcgt actgta        46

<210> SEQ ID NO 36
<211> LENGTH: 46
<212> TYPE: DNA
<213> ORGANISM: Artificial Sequence
<220> FEATURE:
<223> OTHER INFORMATION: primer KM192

<400> SEQUENCE: 36
tcaactatct catatacagc ggccgcatgg ggtgtacagt gagtac        46

<210> SEQ ID NO 37
<211> LENGTH: 46
<212> TYPE: DNA
<213> ORGANISM: Artificial Sequence
<220> FEATURE:
<223> OTHER INFORMATION: primer KM193

<400> SEQUENCE: 37
tcgaattcct gcagcccggg ggatccgagc gacctcatgc tatacc        46
```

<210> SEQ ID NO 38
<211> LENGTH: 46
<212> TYPE: DNA
<213> ORGANISM: Artificial Sequence
<220> FEATURE:
<223> OTHER INFORMATION: primer KM194

<400> SEQUENCE: 38
tggagctcca ccgcggtggc ggccgccttc gagcgtccca aaacct        46

<210> SEQ ID NO 39
<211> LENGTH: 46
<212> TYPE: DNA
<213> ORGANISM: Artificial Sequence
<220> FEATURE:
<223> OTHER INFORMATION: primer KM195

<400> SEQUENCE: 39
taatccatcg atactagtgc ggccgcccga gctcttacgc gggtcg        46

<210> SEQ ID NO 40
<211> LENGTH: 46
<212> TYPE: DNA
<213> ORGANISM: Artificial Sequence
<220> FEATURE:
<223> OTHER INFORMATION: primer KM196

<400> SEQUENCE: 40
tcctcgccct tgctcaccat ggatcccatt atataccctc tagagt        46

<210> SEQ ID NO 41
<211> LENGTH: 46
<212> TYPE: DNA
<213> ORGANISM: Artificial Sequence
<220> FEATURE:
<223> OTHER INFORMATION: primer KM197

<400> SEQUENCE: 41
catccttgta atccatcgat actagtttaa gaggcatcac cagaca        46

<210> SEQ ID NO 42
<211> LENGTH: 46
<212> TYPE: DNA
<213> ORGANISM: Artificial Sequence
<220> FEATURE:
<223> OTHER INFORMATION: primer KM198

<400> SEQUENCE: 42
tcaactatct catatacagc ggccgcatgg gtgctccacc taagaa        46

<210> SEQ ID NO 43
<211> LENGTH: 46
<212> TYPE: DNA
<213> ORGANISM: Artificial Sequence
<220> FEATURE:
<223> OTHER INFORMATION: primer KM245

<400> SEQUENCE: 43
catccttgta atccatcgat actagtttac aacaattcgt actgtt        46

<210> SEQ ID NO 44
<211> LENGTH: 46
<212> TYPE: DNA
<213> ORGANISM: Artificial Sequence
<220> FEATURE:
<223> OTHER INFORMATION: primer KM246

-continued

<400> SEQUENCE: 44
tcaactatct catatacagc ggccgcatgg gttgcctggg taattc                46

<210> SEQ ID NO 45
<211> LENGTH: 46
<212> TYPE: DNA
<213> ORGANISM: Artificial Sequence
<220> FEATURE:
<223> OTHER INFORMATION: primer KM251

<400> SEQUENCE: 45
tcgaattcct gcagcccggg ggatcccaca caccatagct tcaaaa                46

<210> SEQ ID NO 46
<211> LENGTH: 46
<212> TYPE: DNA
<213> ORGANISM: Artificial Sequence
<220> FEATURE:
<223> OTHER INFORMATION: primer KM252

<400> SEQUENCE: 46
tggagctcca ccgcggtggc ggccgccttc gagcgtccca aaacct                46

<210> SEQ ID NO 47
<211> LENGTH: 45
<212> TYPE: DNA
<213> ORGANISM: Artificial Sequence
<220> FEATURE:
<223> OTHER INFORMATION: primer SB3

<400> SEQUENCE: 47
atctaagttt taattacaaa ggatccatgc atcaccatca ccatc                 45

<210> SEQ ID NO 48
<211> LENGTH: 46
<212> TYPE: DNA
<213> ORGANISM: Artificial Sequence
<220> FEATURE:
<223> OTHER INFORMATION: primer SB4

<400> SEQUENCE: 48
ttagagcgga tcttagctag ccgcggttat ggggaatgaa tctttc                46

<210> SEQ ID NO 49
<211> LENGTH: 47
<212> TYPE: DNA
<213> ORGANISM: Artificial Sequence
<220> FEATURE:
<223> OTHER INFORMATION: primer SB89

<400> SEQUENCE: 49
ttagagcgga tcttagctag ccgcggttac ttttgagatt taccacc               47

<210> SEQ ID NO 50
<211> LENGTH: 49
<212> TYPE: DNA
<213> ORGANISM: Artificial Sequence
<220> FEATURE:
<223> OTHER INFORMATION: primer SB90

<400> SEQUENCE: 50
taagttttaa ttacaaagga tccaaaacaa tggatttgcc accacaatt             49

<210> SEQ ID NO 51

<211> LENGTH: 1122
<212> TYPE: DNA
<213> ORGANISM: Artificial Sequence
<220> FEATURE:
<223> OTHER INFORMATION: STF1

<400> SEQUENCE: 51

| | |
|---|---|
| atgaagctac tgtcttctat cgaacaagca tgcgatattt gccgacttaa aaagctcaag | 60 |
| tgctccaaag aaaaaccgaa gtgcgccaag tgtctgaaga caactgggga gtgtcgctac | 120 |
| tctcccaaaa ccaaaaggtc tccgctgact agggcacatc tgacagaagt ggaatcaagg | 180 |
| ctagaaagac tggaacagct atttctactg attttcctc gcgaagacct tgacatgatt | 240 |
| ttgaaaatgg attctttaca ggatataaaa gcattgttaa caggattatt tgtacaagat | 300 |
| aatgtgaata agatgccgt cacagataga ttggcttcag tggagactga tatgcctcta | 360 |
| acattgagac agcatagaat aagtgcgaca tcatcatcgg aagagagtag taacaaaggt | 420 |
| caaagacagt tgactgtatc tagaccatct agtacaacaa atcagataa ttcgcctcca | 480 |
| aaattagaaa gcgagaattt taaggataat gagttggtaa cagtaactaa tcagccgctt | 540 |
| ttaggcgttg gcctcatgga tgacgatgcg ccagaatccc cctctcaaat taatgatttt | 600 |
| attcctcaga aattgattat agaacccaat actctcgaat tgaatggtct cacagaagaa | 660 |
| acgcctcatg acttacccaa gaataccgct aagggcagag acgaagaaga ttttcctctc | 720 |
| gactattttc ctgtatctgt tgaataccct acggaggaaa atgcgtttga tccgttccct | 780 |
| ccacaggctt ttacgccagc tgcccttcc atgcctattt cctatgataa cgtgaatgaa | 840 |
| agggattcta tgcccgttaa ttctcttctt aatagatacc cctatcagtt atcagtggca | 900 |
| cccactttcc cagtgccacc atcatcatcg aggcaacatt ttatgtatcc ttacgacgtt | 960 |
| ccagattatg ctattgactc tgcagctcat catgataact ccacaattcc gttggatttt | 1020 |
| atgcccaggg atgctcttca tggatttgat tggtctgaag aggatgacat gtcggatggc | 1080 |
| ttgcccttcc tgaaaacgga ccccaacaat aatgggttct aa | 1122 |

<210> SEQ ID NO 52
<211> LENGTH: 1035
<212> TYPE: DNA
<213> ORGANISM: Artificial Sequence
<220> FEATURE:
<223> OTHER INFORMATION: STF2 sequence

<400> SEQUENCE: 52

| | |
|---|---|
| atgggtgctc cacctaagaa gaaaagaaag gttgccaaag ctttgactgc cagacaacaa | 60 |
| gaagtcttcg atttgattag agatcatatt tctcaaactg gtatgccacc aactagagct | 120 |
| gaaattgctc aaagattggg tttcagatct ccaaacgccg ctgaagaaca cttgaaagct | 180 |
| ttggctagaa agggtgtcat tgaaattgtt tctggtgctt ctagaggtat tagattgttg | 240 |
| caagaagaag aagaaggttt gccattggtt ggtagagtcg gtagaccatc ttctactact | 300 |
| aaatctgata actctccacc aaagttggaa tctgaaaact tcaaagataa cgaattggtt | 360 |
| actgttacaa atcaaccatt gttaggtgtc ggtttgatgg atgacgatgc tccagaatct | 420 |
| ccttctcaaa ttaacgattt cattccacaa aagttgatta ttgaaccaaa cactttggaa | 480 |
| ttgaacggtt tgactgaaga aactccacac gatttgccaa agaatactgc caaaggtaga | 540 |
| gatgaggaag acttcccatt ggattacttt ccagtttctg tcgaatatcc aactgaagaa | 600 |
| aacgctttcg atccatttcc accacaagcc tttactccag ctgcaccatc tatgccaatt | 660 |
| tcttacgata acgttaatga agagattct atgccagtca actcattgtt gaatagatac | 720 |

```
ccatatcaat tgtctgttgc tccaactttc ccagttcctc catcttcttc aagacaacac    780
tttatgggta ttaacaagga tattgaggaa tgtaatgcca tcattgaaca attcatcgat    840
tacttgagaa ctggtcaaga aatgccaatg gaaatggccg atcaagccat taacgttgtc    900
ccaggtatga ctccaaagac tattttgcac gctggtccac caattcaacc agattggttg    960
aaatctaacg gtttccacga aattgaagct gatgtcaatg acacatcttt gttattgtct   1020
ggtgatgcct cttaa                                                    1035

<210> SEQ ID NO 53
<211> LENGTH: 707
<212> TYPE: DNA
<213> ORGANISM: Artificial Sequence
<220> FEATURE:
<223> OTHER INFORMATION: STF3 sequence

<400> SEQUENCE: 53
tgactatgga ttctggtgct gataatcaac aatcttcttg taaagatttg aaaagattgt     60
tttctggtac tcaaatttct actattgctg aatctgaaga ttctcaagaa tctgttgatt    120
ctgttactga ttctcaaaaa agaagagaaa ttttgtctag aagaccatct tatagaaaaa    180
ttttgaatga tttgtcttct attgaacaag cttgtgatat ttgtagattg aaaaaattga    240
aatgttctaa agaaaaacca aaatgtgcta atgtttgaa aaataattgg gaatgtagat     300
attctccaaa aactaaaaga tctccattga ctagagctca tttgactgaa gttgaatcta    360
gattggaaag attggaacaa ttgttttttgt tgattttttcc aagagaagat ttggatatga    420
ttttgaaaat ggattctttg caagatatta agctttgtt gactggtttg tttgttcaag    480
ataatgttaa taaagatgct gttactgata gattggcttc tgttgaaact gatatgccat    540
tgactttgag acaacataga atttctgcta cttcttcttc tgaagaatct tctaataaag    600
gtcaaagaca attgactgtt tctattgatt ctgctgctca tcatgataat tctactattc    660
cattggattt tatgccaaga gatgctttgc atggttttga ttggtaa                 707

<210> SEQ ID NO 54
<211> LENGTH: 173
<212> TYPE: DNA
<213> ORGANISM: Artificial Sequence
<220> FEATURE:
<223> OTHER INFORMATION: PGal4(5x)

<400> SEQUENCE: 54
ccgagctctt acgcgggtcg aagcggagta ctgtcctccg agtggagtac tgtcctccga     60
gcggagtact gtcctccgag tcgagggtcg aagcggagta ctgtcctccg agtggagtac    120
tgtcctccga gcggagtact gtcctccgag tcgactctag agggtatata atg           173

<210> SEQ ID NO 55
<211> LENGTH: 185
<212> TYPE: DNA
<213> ORGANISM: Artificial Sequence
<220> FEATURE:
<223> OTHER INFORMATION: PLexA(4x)

<400> SEQUENCE: 55
ccgagctctt acgcgggtcg aagtgctgta tatactcaca gcaagtggag tactgtcctc     60
cgagaactgt atatacaccc agggagtcga gggtcgaagt actgtatgag catacagtaa    120
gtggagtact gtcctccgag aactgtatat aaatacagtt agtcgactct agagggtata    180
```

```
taatg                                                              185

<210> SEQ ID NO 56
<211> LENGTH: 329
<212> TYPE: DNA
<213> ORGANISM: Artificial Sequence
<220> FEATURE:
<223> OTHER INFORMATION: PCRE

<400> SEQUENCE: 56
tcctggaagt ctcatggaga ttatacttta tgcaccagac agtgacgtca gctgccagat     60
cccatggccg tcatactgtg acgtctttca gacaccccat tgacgtcaat gggagaactt    120
tagtatccgt ttagctagtt agtacctttg cacggaaatg tattaattag gagtatattg    180
agaaatagcc gccgacaaaa aggaagtctc ataaaagtgt ctaacagaca attagcgcaa    240
taagaagaaa gaaaacggat tgaagttgag tcgagaataa tatggcaccc agaaaacgct    300
ttaggctact cgaattaggg tcaccaatg                                      329

<210> SEQ ID NO 57
<211> LENGTH: 179
<212> TYPE: DNA
<213> ORGANISM: Artificial Sequence
<220> FEATURE:
<223> OTHER INFORMATION: pGal4(5x) repressor

<400> SEQUENCE: 57
tcgactctag agggtatata ccgagctctt acgcgggtcg aagcggagta ctgtcctccg     60
agtggagtac tgtcctccga gcggagtact gtcctccgag tcgagggtcg aagcggagta    120
ctgtcctccg agtggagtac tgtcctccga gcggagtact gtcctccgag ggatccatg     179

<210> SEQ ID NO 58
<211> LENGTH: 188
<212> TYPE: DNA
<213> ORGANISM: Artificial Sequence
<220> FEATURE:
<223> OTHER INFORMATION: pLexA(4x) repressor

<400> SEQUENCE: 58
ccgagctctt acgcgggtcg aagtgctgta tatactcaca gcaagtggag tactgtcctc     60
cgagaactgt atatacaccc agggagtcga gggtcgaagt actgtatgag catacagtaa    120
gtggagtact gtcctccgag aactgtatat aaatacagtt agtcgactct agagggtata    180
taatgatg                                                             188

<210> SEQ ID NO 59
<211> LENGTH: 960
<212> TYPE: DNA
<213> ORGANISM: Artificial Sequence
<220> FEATURE:
<223> OTHER INFORMATION: OR1G1 wild type sequence

<400> SEQUENCE: 59
atgcatcacc atcaccatca cgaaggtaag aatttgacct ctatttccga gtgtttctta     60
cttggtttct ccgaacaatt ggaagaacag aagccattgt tcggttcctt cctgtttatg    120
tacttggtca ccgtcgctgg taacttgtta atcatattag tcattattac cgatacccag    180
ttacataccc caatgtattt cttcttggct aacttatccc tagctgacgc ttgtttcgtt    240
tccactaccg tcccaaagat gttggctaac attcaaattc aatcccaagc tatttcctac    300
tccggttgtt tattgcaatt gtacttcttt atgttgttcg ttatgttgga ggctttcttg    360
```

```
ttggctgtta tggcttacga ttgctacgtc gctatttgtc atccattgca ttacatcttg    420
attatgtccc caggtttgtg tatcttctta gtctccgcct cctggattat gaacgctttg    480
cattccttgt tgcataacctt gttaatgaac tctttatcct tctgtgctaa ccacgaaatt    540
ccacatttct tttgtgatat taacccattg ttgtccttgt cctgtaccga tccattcacc    600
aacgaattgg ttatcttcat taccggtggt ttgactggtt tgatttgtgt cttgtgtttg    660
attatctcct acactaacgt cttctccacc attttgaaaa ttccatccgc tcaaggtaaa    720
agaaaagcat tctccacctg ttcctcccat tgtccgttg tctccttgtt ctttggtacc    780
tcattctgtg tcgatttctc ttccccatcc actcattccg ctcaaaagga taccgttgct    840
tccgttatgt acaccgtcgt cactccaatg ttgaatccat ttatttattc cttaagaaat    900
caagaaatta gtcctccctt gagaaagttg atttgggtta gaaagattca ttccccataa    960
```

<210> SEQ ID NO 60
<211> LENGTH: 960
<212> TYPE: DNA
<213> ORGANISM: Artificial Sequence
<220> FEATURE:
<223> OTHER INFORMATION: A2 hit

<400> SEQUENCE: 60

```
atgcatcacc atcaccatca cgaaggtaag aatttgacct ctatttccga gtgtttctta     60 cttggttttct ccgaacaatt ggaagaacag aagccattgt tcggttcctt cctgtttatg    120
tacttggtca ccgtcgctgg taacttgtta atcatattag tcattattac cgatacccag    180
ttacataccc caatgtattt cttcttggct aacttatccc tagctgacgc ttgtttcgtt    240
tccactaccg tcccaaagtc tttggctaac attcaaattc aatcccaagc tatttcctac    300
tccggttgtt tattgcaatt gtacttcttt atgttgttcg ttatgttgga ggcttttcttg    360 ttggctgtta tggcttacga ttgctacgtc gctatttgtc atccattgca ttacatcttg    420
attatgtccc caggtttgtg tatcttctta gtctccgcct cctggattat gaacgctttg    480
cattccttgt tgcataacctt gttaatgaac tctttatcct tctgtgctaa ccacgaaatt    540
ccacatttct tttgtgatat aacgtgttg ttgtccttgt cctgtaccga tccattcacc    600
aacgaattgg ttatcttcat taccggtggt ttgactggtt tgatttgtgt cttgtgtttg    660
attatctcct acactaacgt cttctccacc attttgaaaa ttccatccgc tcaaggtaaa    720
agaaaagcat tctccacctg ttcctcccat tgtccgttg tctccttgtt ctttggtacc    780
tcattctgtg tcggcttctc ttccccatcc actcattccg ctcaaaagga taccgttgct    840
tccactatgt acaccgtcgt cactccaatg ttgaatccat ttatttattc cttaagaaat    900
caagaaatta gtcctccctt gagaaagttg atttgggtta gaaagattca ttccccataa    960
```

<210> SEQ ID NO 61
<211> LENGTH: 319
<212> TYPE: PRT
<213> ORGANISM: Artificial Sequence
<220> FEATURE:
<223> OTHER INFORMATION: A2 hit

<400> SEQUENCE: 61

```
Met His His His His His His Glu Gly Lys Asn Leu Thr Ser Ile Ser
1               5                   10                  15

Glu Cys Phe Leu Leu Gly Phe Ser Glu Gln Leu Glu Glu Gln Lys Pro
            20                  25                  30
```

Leu Phe Gly Ser Phe Leu Phe Met Tyr Leu Val Thr Val Ala Gly Asn
                 35                  40                  45

Leu Leu Ile Ile Leu Val Ile Ile Thr Asp Thr Gln Leu His Thr Pro
 50                  55                  60

Met Tyr Phe Phe Leu Ala Asn Leu Ser Leu Ala Asp Ala Cys Phe Val
 65                  70                  75                  80

Ser Thr Thr Val Pro Lys Ser Leu Ala Asn Ile Gln Ile Gln Ser Gln
                 85                  90                  95

Ala Ile Ser Tyr Ser Gly Cys Leu Leu Gln Leu Tyr Phe Phe Met Leu
                100                 105                 110

Phe Val Met Leu Glu Ala Phe Leu Leu Ala Val Met Ala Tyr Asp Cys
                115                 120                 125

Tyr Val Ala Ile Cys His Pro Leu His Tyr Ile Leu Ile Met Ser Pro
                130                 135                 140

Gly Leu Cys Ile Phe Leu Val Ser Ala Ser Trp Ile Met Asn Ala Leu
145                 150                 155                 160

His Ser Leu Leu His Thr Leu Leu Met Asn Ser Leu Ser Phe Cys Ala
                165                 170                 175

Asn His Glu Ile Pro His Phe Phe Cys Asp Ile Asn Val Leu Leu Ser
                180                 185                 190

Leu Ser Cys Thr Asp Pro Phe Thr Asn Glu Leu Val Ile Phe Ile Thr
                195                 200                 205

Gly Gly Leu Thr Gly Leu Ile Cys Val Leu Cys Leu Ile Ile Ser Tyr
                210                 215                 220

Thr Asn Val Phe Ser Thr Ile Leu Lys Ile Pro Ser Ala Gln Gly Lys
225                 230                 235                 240

Arg Lys Ala Phe Ser Thr Cys Ser Ser His Leu Ser Val Val Ser Leu
                245                 250                 255

Phe Phe Gly Thr Ser Phe Cys Val Gly Phe Ser Ser Pro Ser Thr His
                260                 265                 270

Ser Ala Gln Lys Asp Thr Val Ala Ser Thr Met Tyr Thr Val Val Thr
                275                 280                 285

Pro Met Leu Asn Pro Phe Ile Tyr Ser Leu Arg Asn Gln Glu Ile Lys
290                 295                 300

Ser Ser Leu Arg Lys Leu Ile Trp Val Arg Lys Ile His Ser Pro
305                 310                 315

<210> SEQ ID NO 62
<211> LENGTH: 960
<212> TYPE: DNA
<213> ORGANISM: Artificial Sequence
<220> FEATURE:
<223> OTHER INFORMATION: J6

<400> SEQUENCE: 62
atgcatcacc atcaccatca cgaaggtaag aatttgacct ctatttccga gtgtttctta      60 cttggttct ccgaacaatt ggaagaacag aagccattgt tcggttcctt cctgtttatg     120
tacttggtca ccgtcgctgg taacttgtta atcatattag tcattattac cgatacccag     180
ttacataccc caatgtattt cttcttggct aacttatccc tagctgacgc ttgtttcgtt     240
tccactaccg tcccaaagat gttggctaac attcaaattc aatcccaagc tatttcctac     300
tccggttgtt tattgcaatt gtacttcttt atgttgttcg ttatgttgga ggctttcttg     360
ttggctgtta tggcttacga ttgctacgtc gctatttgtc atccattgca ttacatcttg     420
attatgtccc caggtttgtg tatcttctta gtctccgcct cctggattat gaacgctttg     480

```
cattccttgt tgcatacctt gttaatgaac tctttatcct tctgtgctaa ccacgaaatt    540
ccacatttct tttgtgatat taacccattg ttgtccttgt cctgtaccga tccattcacc    600
aacgaattgg ttatcttcat taccggtggt ttgactggtt tgatttgtgt cttgtgtttg    660
attatctcct acactaacgt cttctccacc atttgaaaa ttcatccgc tcaaggtaaa    720 agaaaagcat tctccacctg ttcctcccat ttgtccgttg tctccttgtt ctttggtacc    780
tcattctgtg tcgattctc ttccccatcc actcattccg ctcaaaagga taccgttgct    840
tccgttatgt acaccgtcgt cactccaatg ttgaatccat ttatttattc cttaagaaat    900
caagaaatta agtcctccct gagaaagttg atttgggtta gaaagattca ttccccataa    960
```

<210> SEQ ID NO 63
<211> LENGTH: 960
<212> TYPE: DNA
<213> ORGANISM: Artificial Sequence
<220> FEATURE:
<223> OTHER INFORMATION: J8

<400> SEQUENCE: 63

```
atgcatcacc atcaccatca cgaaggtaag aatttgacct ctatttccga gtgtttctta     60
cttggtttct ccgaacaatt ggaagaacag aagccattgt tcggttcctt cctgtttatg    120

tacttggtca ccgtcgctgg taacttgtta atcatattag tcattattac cgatacccag    180
ttacataccc caatgтатττ cttcttggct aacttatccc tagctgacgc ttgtttcgtt    240
tccactaccg tcccaaagat gttggctaac attcaaattc aatcccaagc tatttcctac    300

tccgttgtt tattgcaatt gтаcттcтττ atgttgttcg ttatgttgga ggctttcttg    360

ttggctgtta tggcttacga ttgctacgtc gctatttgtc atccattgca ttacatcttg    420
attatgtccc caggtttgtg tatcttctta gtctccgcct cctggattat gaacgстττg    480 cattccttgt tgcatacctt gttaatgaac tctttatcct tctgtgctaa ccacgaaatt    540
ccacatttct tttgtgatat taacccattg ttgtccttgt cctgtaccga tccattcacc    600
aacgaattgg ttatcttcat taccggtggt ttgactggtt tgatttgtgt cttgtgtttg    660
attatctcct acactaacgt cttctccacc atttgaaaa ttcatccgc tcaaggtaaa    720 agaaaagcat tctccacctg ttcctcccat ttgtccgttg tctccttgtt ctttggtacc    780
tcattctgtg tcgattctc ttccccatcc actcattccg ctcaaaagga taccgttgct    840
tccgttatgt acaccgtcgt cactccaatg ttgaatccat ttatttattc cttaagaaat    900
caagaaatta agtcctccct gagaaagttg atttgggtta gaaagattca ttccccataa    960
```

<210> SEQ ID NO 64
<211> LENGTH: 960
<212> TYPE: DNA
<213> ORGANISM: Artificial Sequence
<220> FEATURE:
<223> OTHER INFORMATION: L3 C10EE 4

<400> SEQUENCE: 64

```
atgcatcacc atcaccatca cgaaggtaag aatttgacct ctatttccga gtgtttctta     60
cttggtttct ccgaacaatt ggaagaacag aagccattgt tcggttcctt cctgtttatg    120

tacttggtca ccgtcgctgg taacttgtta atcatattag tcattattac cgatacccag    180
ttacataccc caatgтатττ cttcttggct aacttatccc tagctgacgc ttgtttcgtt    240
tccactaccg tcccaaagat gttggctaac attcaaattc aatcccaagc tatttcctac    300
```

```
tccggttgtt tattgcaatt gtacttcttt tgcttgttcg ttatgttgga ggctttcttg      360
ttggctgtta tggcttacga ttgctacgtc gctatttgtc atccattgca ttacatcttg      420
attatgtccc caggtttgtg tatcttctta gtctccgcct cctggattat gaacgctttg      480
cattccttgt tgcataccct tgttaatgaac tctttatcct tctgtgctaa ccacgaaatt      540
ccacatttct tttgtgatat aacccattg ttgtccttgt cctgtaccga tccattcacc      600
aacgaattgg ttatcttcat taccggtggt ttgactggtt tgatttgtgt cttgtgtttg      660
attatctcct acactaacgt cttctccacc attttgaaaa ttccatccgc tcaaggtaaa      720
agaaaagcat tctccacctg ttcctcccat tgtccgttg tctccttgtt ctttggtacc       780
ctcacttgtg tcgatttctc ttccccatcc actcattccg ctcaaaagga taccgttgct      840
tcctatatgt acaccgtcgt cactccaatg ttgaatccat ttatttattc cttaagaaat      900
caagaaatta agtcctcctt gagaaagttg atttgggtta gaaagattca ttccccataa      960
```

<210> SEQ ID NO 65
<211> LENGTH: 1054
<212> TYPE: DNA
<213> ORGANISM: Artificial Sequence
<220> FEATURE:
<223> OTHER INFORMATION: L3 C12EE 5

<400> SEQUENCE: 65

```
atgcatcacc atcaccatca cgaaggtaag aatttgacct ctatttccga gtgtttctta       60
cttggttcct ccgaacaatt ggaagaacag aagccattgt tcggttcctt cctgtttatg      120
tacttggtca ccgtcgctgg taacttgtta atcatattag tcattattac cgatacccag      180
ttacataccc caatgtattt cttcttggct aacttatccc tagctgacgc ttgtttcgtt      240
tccactaccg tcccaaagat gttggctaac attcaaattc aatcccaagc tatttcctac      300
tccggttgtt tattgcaatg tacttcaaca tgttgttcgt tatgttggag ctttcttgt      360 tggctgttat ggcttacgat tgctacgtcg ctatttgtca tccattgcat acatcttga      420 ttatgtcccc aggtttgtgt atcttcttag tctccgcctc tggattatg aacgctttgc       480 attccttgtt gcataccttg ttaatgaact ctttatcctt ctgtgctaac cacgaaattc      540
cacatttctt ttgtgatatt aacccatagt tgtccttgtc ctgtaccgat ccattcacca      600
acgaattggt tatcttcatt accggtggtt tgactggttt gatttgtgtc ttgtgtttga      660
ttatctccta cactaacgtc ttctccacca ttttgaaaat tccatccgct caaggtaaaa      720
gaaaagcatt ctccacctgt tcctcccatt gtccgttgt ctccttgttc tttggtacct       780
cagactgtgt cgatttctct tccccatcca ctcattccgc taaaggatac cgttgcttcc      840
ccatttgtcc gttgtctcct tgttctttgg tacctcacgc tgtgtcgatt tctcttcccc      900
atccactcat tccgctcaaa aggataccgt tgcttccgtt atgtacaccg tcgtcactcc      960
aatgttgaat ccattatttt attccttaag aaatcaagaa attaagtcct ccttgagaaa     1020
gttgatttgg gttagaaaga ttcattcccc ataa                                  1054
```

<210> SEQ ID NO 66
<211> LENGTH: 1054
<212> TYPE: DNA
<213> ORGANISM: Artificial Sequence
<220> FEATURE:
<223> OTHER INFORMATION: L3 C12EE 6

<400> SEQUENCE: 66

```
atgcatcacc atcaccatca cgaaggtaag aatttgacct ctatttccga gtgtttctta       60
```

```
cttggtttct ccgaacaatt ggaagaacag aagccattgt tcggttcctt cctgtttatg      120
tacttggtca ccgtcgctgg taacttgtta atcatattag tcattattac cgatacccag      180
ttacataccc caatgtattt cttcttggct aacttatccc tagctgacgc ttgtttcgtt      240
tccactaccg tcccaaagat gttggctaac attcaaattc aatcccaagc tatttcctac      300
tccggttgtt tattgcaatg tacttcaaca tgttgttcgt tatgttggag ctttcttgt       360 tggctgttat ggcttacgat tgctacgtcg ctatttgtca tccattgcat tacatcttga     420
ttatgtcccc aggtttgtgt atcttcttag tctccgcctc ctggattatg aacgctttgc     480
attccttgtt gcataccttg ttaatgaact ctttatcctt ctgtgctaac cacgaaattc     540
cacatttctt ttgtgatatt aacccatagt tgtccttgtc ctgtaccgat ccattcacca    600
acgaattggt tatcttcatt accggtggtt tgactggttt gatttgtgtc ttgtgtttga    660
ttatctccta cactaacgtc ttctccacca ttttgaaaat tccatccgct caaggtaaaa    720
gaaaagcatt ctccacctgt tcctcccatt tgtccgttgt ctccttgttc tttggtacct    780
cagactgtgt cgatttctct tccccatcca ctcattccgc taaaggatac cgttgcttcc    840
ccatttgtcc gttgtctcct tgttctttgg tacctcacgc tgtgtcgatt tctcttcccc    900
atccactcat tccgctcaaa aggataccgt tgcttccgtt atgtacaccg tcgtcactcc    960
aatgttgaat ccatttattt attccttaag aaatcaagaa attaagtcct ccttgagaaa   1020
gttgatttgg gttagaaaga ttcattcccc ataa                                1054

<210> SEQ ID NO 67
<211> LENGTH: 960
<212> TYPE: DNA
<213> ORGANISM: Artificial Sequence
<220> FEATURE:
<223> OTHER INFORMATION: L5 C10ME 2

<400> SEQUENCE: 67
atgcatcacc atcaccatca cgaaggtaag aatttgacct ctatttccga gtgtttctta       60
cttggtttct ccgaacaatt ggaagaacag aagccattgt tcggttcctt cctgtttatg      120
tacttggtca ccgtcgctgg taacttgtta atcatattag tcattattac cgatacccag      180
ttacataccc caatgtattt cttcttggct aacttatccc tagctgacgc ttgtttcgtt      240
tccactaccg tcccaaagat gttggctaac attcaaattc aatcccaagc tatttcctac      300
tccggttgtt tattgcaatt gtacttcttt cccttgttcg ttatgttgga gctttcttg      360 ttggctgtta tggcttacga ttgctacgtc gctatttgtc atccattgca ttacatcttg    420
attatgtccc caggtttgtg tatcttctta gtctccgcct cctggattat gaacgctttg    480
cattccttgt tgcataccgt gttaatgaac tctttatcct tctgtgctaa ccacgaaatt    540
ccacatttct tttgtgatat taacccattg ttgtccttgt cctgtaccga tccattcacc    600
aacgaattgg ttatcttcat taccggtggt ttgactggtt tgatttgtgt cttgtgtttg    660
attatctcct acactaacgt cttctccacc attttgaaaa ttccatccgc tcaaggtaaa    720
agaaaagcat ctccacctgt tcctcccat tgtccgttg tctccttgtt ctttggtacc      780
cacctttgtg tcgatttctc ttccccatcc actcattccg ctcaaaagga taccgttgct    840
tcctagatgt acaccgtcgt cactccaatg ttgaatccat ttatttattc cttaagaaat    900
caagaaatta gtcctccctt gagaaagttg atttgggtta gaaagattca ttccccataa    960

<210> SEQ ID NO 68
```

```
<211> LENGTH: 960
<212> TYPE: DNA
<213> ORGANISM: Artificial Sequence
<220> FEATURE:
<223> OTHER INFORMATION: L5 C10ME 3

<400> SEQUENCE: 68
atgcatcacc atcaccatca cgaaggtaag aatttgacct ctatttccga gtgtttctta      60
cttggtttct ccgaacaatt ggaagaacag aagccattgt tcggttcctt cctgtttatg     120
tacttggtca ccgtcgctgg taacttgtta atcatattag tcattattac cgatacccag     180
ttacataccc caatgtattt cttcttggct aacttatccc tagctgacgc ttgtttcgtt     240
tccactaccg tcccaaagat gttggctaac attcaaattc aatcccaagc tatttcctac     300
tccggttgtt tattgcaatt gtacttcttt gtcttgttcg ttatgttgga ggctttcttg     360
ttggctgtta tggcttacga ttgctacgtc gctatttgtc atccattgca ttacatcttg     420
attatgtccc caggtttgtg tatcttctta gtctccgcct cctggattat gaacgctttg     480
cattccttgt tgcatacctt gttaatgaac tctttatcct tctgtgctaa ccacgaaatt     540
ccacatttct tttgtgatat taacccattg ttgtccttgt cctgtaccga tccattcacc     600
aacgaattgg ttatcttcat taccggtggt ttgactggtt tgattgtgt cttgtgtttg     660
attatctcct acactaacgt cttctccacc attttgaaaa ttccatccgc tcaaggtaaa     720
agaaaagcat tctccacctg ttcctcccat tgtccgttg tctccttgtt ctttggtacc     780
caggattgtg tcgatttctc ttccccatcc actcattccg ctcaaaagga taccgttgct     840
tcctcgatgt acaccgtcgt cactccaatg ttgaatccat ttatttattc cttaagaaat     900
caagaaatta agtcctcctt gagaaagttg atttgggtta gaaagattca ttccccataa     960

<210> SEQ ID NO 69
<211> LENGTH: 960
<212> TYPE: DNA
<213> ORGANISM: Artificial Sequence
<220> FEATURE:
<223> OTHER INFORMATION: L5 C10ME 4

<400> SEQUENCE: 69
atgcatcacc atcaccatca cgaaggtaag aatttgacct ctatttccga gtgtttctta      60
cttggtttct ccgaacaatt ggaagaacag aagccattgt tcggttcctt cctgtttatg     120
tacttggtca ccgtcgctgg taacttgtta atcatattag tcattattac cgatacccag     180
ttacataccc caatgtattt cttcttggct aacttatccc tagctgacgc ttgtttcgtt     240
tccactaccg tcccaaagat gttggctaac attcaaattc aatcccaagc tatttcctac     300
tccggttgtt tattgcaatt gtacttcttt gtcttgttcg ttatgttgga ggctttcttg     360
ttggctgtta tggcttacga ttgctacgtc gctatttgtc atccattgca ttacatcttg     420
attatgtccc caggtttgtg tatcttctta gtctccgcct cctggattat gaacgctttg     480
cattccttgt tgcatacctt gttaatgaac tctttatcct tctgtgctaa ccacgaaatt     540
ccacatttct tttgtgatat taacccattg ttgtccttgt cctgtaccga tccattcacc     600
aacgaattgg ttatcttcat taccggtggt ttgactggtt tgattgtgt cttgtgtttg     660
attatctcct acactaacgt cttctccacc attttgaaaa ttccatccgc tcaaggtaaa     720
agaaaagcat tctccacctg ttcctcccat tgtccgttg tctccttgtt ctttggtacc     780
gcggcttgtg tcgatttctc ttccccatcc actcattccg ctcaaaagga taccgttgct     840
tccaatatgt acaccgtcgt cactccaatg ttgaatccat ttatttattc cttaagaaat     900
```

```
caagaaatta agtcctcctt gagaaagttg atttgggtta gaaagattca ttccccataa    960
```

<210> SEQ ID NO 70
<211> LENGTH: 960
<212> TYPE: DNA
<213> ORGANISM: Artificial Sequence
<220> FEATURE:
<223> OTHER INFORMATION: L5 C10ME 6

<400> SEQUENCE: 70

```
atgcatcacc atcaccatca cgaaggtaag aatttgacct ctatttccga gtgtttctta     60
cttggtttct ccgaacaatt ggaagaacag aagccattgt tcggttcctt cctgtttatg    120
tacttggtca ccgtcgctgg taacttgtta atcatattag tcattattac cgatacccag    180
ttacataccc caatgtattt cttcttggct aacttatccc tagctgacgc ttgtttcgtt    240
tccactaccg tcccaaagat gttggctaac attcaaattc aatcccaagc tatttcctac    300
tccggttgtt tattgcaatt gtacttcttt atccttgttcg ttatgttgga ggcttcttg    360
ttggctgtta tggcttacga ttgctacgtc gctatttgtc atccattgca ttacatcttg    420
attatgtccc caggtttgtg tatcttctta gtctccgcct cctggattat gaacgctttg    480
cattccttgt tgcatacctt gttaatgaac tctttatcct tctgtgctaa ccacgaaatt    540
ccacatttct tttgtgatat taacccattg ttgtccttgt cctgtaccga tccattcacc    600
aacgaattgg ttatcttcat taccggtggt ttgactggtt tgatttgtgt cttgtgtttg    660
attatctcct acactaacgt cttctccacc attttgaaaa ttccatccgc tcaaggtaaa    720
agaaaagcat tctccacctg ttcctcccat ttgtccgttg tctccttgtt ctttggtacc    780
gcggcttgtg tcgatttctc ttccccatcc actcattccg ctcaaaagga taccgttgct    840
tccaggatgt acaccgtcgt cactccaatg ttgaatccat ttatttattc cttaagaaat    900
caagaaatta agtcctcctt gagaaagttg atttgggtta gaaagattca ttccccataa    960
```

<210> SEQ ID NO 71
<211> LENGTH: 957
<212> TYPE: DNA
<213> ORGANISM: Artificial Sequence
<220> FEATURE:
<223> OTHER INFORMATION: L5 C10ME 7

<400> SEQUENCE: 71

```
atgcatcacc atcaccatca cgaaggtaag aatttgacct ctatttccga gtgtttctta     60
cttggtttct ccgaacaatt ggaagaacag aagccattgt tcggttcctt cctgtttatg    120
tacttggtca ccgtcgctgg taacttgtta atcatattag tcattattac cgatacccag    180
ttacataccc caatgtattt cttcttggct aacttatccc tagctgacgc ttgtttcgtt    240
tccactaccg tcccaaagat gttggctaac attcaaattc aatcccaagc tatttcctac    300
tccggttgtt tattgcaatt gtacttcttt accttgcgtt atgttggagg ctttcttgtt    360
ggctgttatg gcttacgatt gctacgtcgc tatttgtcat ccattgcatt acatcttgat    420
tatgtcccca ggtttgtgta tcttcttagt ctccgcctcc tggattatga acgctttgca    480
ttccttgttg catacttgt taatgaactc tttatccttc tgtgctaacc acgaaattcc    540
acatttcttt tgtgatatta acccattgtt gtccttgtcc tgtaccgatc cattcaccaa    600
cgaattggtt atcttcatta ccggtggttt gactggtttg atttgtgtct tgtgtttgat    660
tatctcctac actaacgtct tctccaccat tttgaaaatt ccatccgctc aaggtaaaag    720
```

```
aaaagcattc tccacctgtt cctcccattt gtccgttgtc tccttgttct ttggtacctt    780
cacgtgtgtc gatttctctt ccccatccac tcattccgct caaaaggata ccgttgttcc    840
aatatgtaca ccgtcgtcac tccaatgttg aatccattta tttattcctt aagaaatcaa    900
gaaattaagt cctccttgag aaagttgatt tgggttagaa agattcattc cccataa       957
```

<210> SEQ ID NO 72
<211> LENGTH: 959
<212> TYPE: DNA
<213> ORGANISM: Artificial Sequence
<220> FEATURE:
<223> OTHER INFORMATION: L6 isobutanol 10

<400> SEQUENCE: 72

```
atgcatcacc atcaccatca cgaaggtaag aatttgacct ctatttccga gtgtttctta     60
cttggtttct ccgaacaatt ggaagaacag aagccattgt tcggttcctt cctgtttatg    120
tacttggtca ccgtcgctgg taacttgtta atcatattag tcattattac cgatacccag    180
ttacataccc caatgtattt cttcttggct aacttatccc tagctgacgc ttgtttcgtt    240
tccactaccg tcccaaagat ttggctgtca ttcaaattca atcccaagct atttcctact    300
ccggttgttt attgaatttg tacttcttta tgttgttcgt tatgttggag ctttcttgt    360 tggctgttat ggcttacgat tgctacgtcg ctatttgtca tccattgcat tacatcttga    420
ttatgtcccc aggtttgtgt atcttcttag tctccgcctc ctggattatg aacgctttgc    480
attccttgtt gcatacccttg ttaatgaact ctttatcctt ctgtgctaac cacgaaattc    540
cacatttctt ttgtgatatt aacccattgt tgtccttgtc ctgtaccgat ccattcacca    600
acgaattggt tatcttcatt accggtggtt tgactggttt gatttgtgtc ttgtgtttga    660
ttatctccta cactaacgtc ttctccacca ttttgaaaat tccatccgct caaggtaaaa    720
gaaaagcatt ctccacctgt tcctcccatt tgtccgttgt ctccttgttc tttggtacct    780
cattctgtgt cgatttctct tccccatcca ctcattccgc tcaaaaggat accgttgctt    840
ccgttatgta caccgtcgtc actccaatgt tgaatccatt tatttattcc ttaagaaatc    900
aagaaattaa gtcctccttg agaaagttga tttgggttag aaagattcat tccccataa    959
```

<210> SEQ ID NO 73
<211> LENGTH: 957
<212> TYPE: DNA
<213> ORGANISM: Artificial Sequence
<220> FEATURE:
<223> OTHER INFORMATION: L6 isobutanol 12

<400> SEQUENCE: 73

```
atgcatcacc atcaccatca cgaaggtaag aatttgacct ctatttccga gtgtttctta     60
cttggtttct ccgaacaatt ggaagaacag aagccattgt tcggttcctt cctgtttatg    120
tacttggtca ccgtcgctgg taacttgtta atcatattag tcattattac cgatacccag    180
ttacataccc caatgtattt cttcttggct aacttatccc tagctgacgc ttgtttcgtt    240
tccactaccg tcccaaagaa gttggctatg attcaaattc aatcccaagc tatttcctac    300
tccggttgtt tattgtagtt gtacttcttt atgttgttcg ttatgttgga ggctttcttg    360
ttggctgtta tggcttacga ttgctacgtc gctatttgtc atccattgca ttacatcttg    420
attatgtccc caggtttgtg tatcttctta gtctccgcct cctggattat gaacgctttg    480
cattccttgt tgcatacctt gttaatgaac tctttatcct tctgtgctaa ccacgaaatt    540
ccacatttct ttgatattaa cccattgttg tccttgtcct gtaccgatcc attcaccaac    600
```

```
gaattggtta tcttcattac cggtggtttg actggtttga tttgtgtctt gtgtttgatt    660
atctcctaca ctaacgtctt ctccaccatt ttgaaaattc catccgctca aggtaaaaga    720
aaagcattct ccacctgttc ctcccatttg tccgttgtct ccttgttctt tggtacctca    780
ttctgtgtcg atttctcttc cccatccact cattccgctc aaaaggatac cgttgcttcc    840
gttatgtaca ccgtcgtcac tccaatgttg aatccattta tttattcctt aagaaatcaa    900
gaaattaagt cctccttgag aaagttgatt tgggttagaa agattcattc cccataa      957
```

<210> SEQ ID NO 74
<211> LENGTH: 960
<212> TYPE: DNA
<213> ORGANISM: Artificial Sequence
<220> FEATURE:
<223> OTHER INFORMATION: L7 C10EE 6

<400> SEQUENCE: 74

```
atgcatcacc atcaccatca cgaaggtaag aatttgacct ctatttccga gtgtttctta     60
cttggtttct ccgaacaatt ggaagaacag aagccattgt tcggttcctt cctgtttatg    120
tacttggtca ccgtcgctgg taacttgtta atcatattag tcattattac cgatacccag    180
ttacataccc caatgtattt cttcttggct aacttatccc tagctgacgc ttgtttcgtt    240
tccactaccg tcccaaagat gttggctaac attcaaattc aatcccaagc tatttcctac    300
tccggttgtt tattgcaatt gtacttcttt atgttgttcg ttatgttgga ggcttcttg     360 ttggctgtta tggcttacga ttgctacgtc gctatttgtc atccattgca ttacatcttg    420
attatgtccc caggtttgtg tatcttctta gtctccgcct cctggattat gaacgctttg    480
cattccttgt tgcataacctt gttaatgaac tctttatcct tctgtgctaa ccacgaaatt    540
ccacatttct tttgtgatat taacccattg ttgtccttgt cctgtaccga tccattcacc    600
aacgaattgg ttatcttcat taccggtggt ttgactggtt tgatttgtgt cttgtgtttg    660
attatctcct acactaacgt cttctccacc attttgaaaa ttccatccgc tcaaggtaaa    720
agaaaagcat tctccacctg ttcctcccat ttgtccgttg tctccttgtt ctttggtacc    780
tcattctgtg tcgatttctc ttccccatcc actcattccg ctcaaaagga taccgttgct    840
tccgttatgt acaccgtcgt cactccaatg ttgaatccat ttatttattc cttaagaaat    900
caagaaatta gtcctccctt gagaaagttg atttgggtta gaaagattca ttccccataa    960
```

<210> SEQ ID NO 75
<211> LENGTH: 959
<212> TYPE: DNA
<213> ORGANISM: Artificial Sequence
<220> FEATURE:
<223> OTHER INFORMATION: L7 C10EE 9

<400> SEQUENCE: 75

```
atgcatcacc atcaccatca cgaaggtaag aatttgacct ctatttccga gtgtttctta     60
cttggtttct ccgaacaatt ggaagaacag aagccattgt tcggttcctt cctgtttatg    120
tacttggtca ccgtcgctgg taacttgtta atcatattag tcattattac cgatacccag    180
ttacataccc caatgtattt cttcttggct aacttatccc tagctgacgc ttgtttcgtt    240
tccactaccg tcccaaagat gttggctaac attcaaattc aatcccaagc tatttcctac    300
tccggttgtt tattgcaatt gtacttcttt atgttgttcg tatgtggag gctttcttgt    360 tggctgttat ggcttacgat tgctacgtcg ctatttgtca tccattgcat tacatcttga    420
```

```
ttatgtcccc aggtttgtgt atcttcttag tctccgcctc ctggattatg aacgctttgc    480
attccttgtt gcatacccttg ttaatgaact ctttatcctt ctgtgctaac cacgaaattc    540
cacatttctt ttgtgatatt aacccattgt tgtccttgtc ctgtacctct ccattcacca    600
acgaattggt tatcttcatt accgtggtt tgactggttt gatttgtgtc ttgtgtttga    660
ttatctccta cactaacgtc ttctccacca ttttgaaaat tccatccgct caaggtaaaa    720
gaaaagcatt ctccacctgt tcctcccatt tgtccgttgt ctccttgttc tttggtaccc    780
cgaagtgtgt cgccttctct tccccatcca ctcattccgc tcaaaaggat accgttgctt    840
ccgttatgta caccgtcgtc actccaatgt tgaatccatt tatttattcc ttaagaaatc    900
aagaaattaa gtcctccttg agaaagttga tttgggttag aaagattcat tccccataa    959
```

```
<210> SEQ ID NO 76
<211> LENGTH: 50
<212> TYPE: DNA
<213> ORGANISM: Artificial Sequence
<220> FEATURE:
<223> OTHER INFORMATION: primer RP1

<400> SEQUENCE: 76
acaaacaaaa aaaaaaaaaa aaaaggatcc atgacagtca cactaagac                 50

<210> SEQ ID NO 77
<211> LENGTH: 52
<212> TYPE: DNA
<213> ORGANISM: Artificial Sequence
<220> FEATURE:
<223> OTHER INFORMATION: primer RP2

<400> SEQUENCE: 77
cggatcttag ctagccgcgg taccaagctt ttataattgg ccagtctttt tc            52

<210> SEQ ID NO 78
<211> LENGTH: 49
<212> TYPE: DNA
<213> ORGANISM: Artificial Sequence
<220> FEATURE:
<223> OTHER INFORMATION: primer RP3

<400> SEQUENCE: 78
acaaacaaaa aaaaaaaaaa aaaaggatcc atgggtagga gggcttttg                 49

<210> SEQ ID NO 79
<211> LENGTH: 49
<212> TYPE: DNA
<213> ORGANISM: Artificial Sequence
<220> FEATURE:
<223> OTHER INFORMATION: primer RP4

<400> SEQUENCE: 79
cggatcttag ctagccgcgg taccaagctt ttacaacact cccttcgtg                 49

<210> SEQ ID NO 80
<211> LENGTH: 48
<212> TYPE: DNA
<213> ORGANISM: Artificial Sequence
<220> FEATURE:
<223> OTHER INFORMATION: primer RP5

<400> SEQUENCE: 80
acaaacaaaa aaaaaaaaaa aaaaggatcc atggtgagca agggcgag                  48
```

```
<210> SEQ ID NO 81
<211> LENGTH: 52
<212> TYPE: DNA
<213> ORGANISM: Artificial Sequence
<220> FEATURE:
<223> OTHER INFORMATION: primer RP6

<400> SEQUENCE: 81
cggatcttag ctagccgcgg taccaagctt ttataatttg gacttgtaca gc          52

<210> SEQ ID NO 82
<211> LENGTH: 49
<212> TYPE: DNA
<213> ORGANISM: Artificial Sequence
<220> FEATURE:
<223> OTHER INFORMATION: primer RP7

<400> SEQUENCE: 82
acaaacaaaa aaaaaaaaaa aaaaggatcc atggtgagcg agctgatta              49

<210> SEQ ID NO 83
<211> LENGTH: 49
<212> TYPE: DNA
<213> ORGANISM: Artificial Sequence
<220> FEATURE:
<223> OTHER INFORMATION: primer RP8

<400> SEQUENCE: 83
cggatcttag ctagccgcgg taccaagctt ttatctgtgc cccagtttg              49

<210> SEQ ID NO 84
<211> LENGTH: 52
<212> TYPE: DNA
<213> ORGANISM: Artificial Sequence
<220> FEATURE:
<223> OTHER INFORMATION: primer RP9

<400> SEQUENCE: 84
acaaacaaaa aaaaaaaaaa aaaaggatcc atgtctaaag gtgaagaatt at          52

<210> SEQ ID NO 85
<211> LENGTH: 53
<212> TYPE: DNA
<213> ORGANISM: Artificial Sequence
<220> FEATURE:
<223> OTHER INFORMATION: primer RP10

<400> SEQUENCE: 85
cggatcttag ctagccgcgg taccaagctt ttatttgtac aattcatcca tac         53

<210> SEQ ID NO 86
<211> LENGTH: 46
<212> TYPE: DNA
<213> ORGANISM: Artificial Sequence
<220> FEATURE:
<223> OTHER INFORMATION: primer KM296

<400> SEQUENCE: 86
tcgaattcct gcagcccggg ggatccatca ccctgcattg cctctt                 46

<210> SEQ ID NO 87
<211> LENGTH: 46
<212> TYPE: DNA
<213> ORGANISM: Artificial Sequence
<220> FEATURE:
<223> OTHER INFORMATION: primer KM297
```

```
<400> SEQUENCE: 87
tggagctcca ccgcggtggc ggccgccttc gagcgtccca aaacct                46

<210> SEQ ID NO 88
<211> LENGTH: 46
<212> TYPE: DNA
<213> ORGANISM: Artificial Sequence
<220> FEATURE:
<223> OTHER INFORMATION: primer KM304

<400> SEQUENCE: 88
acaaaaaaaa aaaaaaaaaa ggatccatga aagtccaaat aaccaa                46

<210> SEQ ID NO 89
<211> LENGTH: 46
<212> TYPE: DNA
<213> ORGANISM: Artificial Sequence
<220> FEATURE:
<223> OTHER INFORMATION: primer KM305

<400> SEQUENCE: 89
tcttagctag ccgcggtacc aagctttcag gttgcatctg gaaggt                46
```

US 9,809,862 B2

G-PROTEIN COUPLED RECEPTOR (GPCR)-BASED BIOSENSORS AND USES THEREOF

CROSS-REFERENCE TO RELATED APPLICATIONS

This application claims the benefit of U.S. Provisional Application Ser. No. 62/035,734 filed on Aug. 11, 2014, having the title GPCR-Based Biosensors for Medium-Chain Fatty Acids, the entirety of which is incorporated herein by reference.

STATEMENT REGARDING FEDERALLY SPONSORED RESEARCH OR DEVELOPMENT

This invention was made with government support under grant number DP14AP00041 awarded by the Defense Advanced Research Projects Agency. The government has certain rights to this invention.

SEQUENCE LISTING

This application contains a sequence listing filed in electronic form as an ASCII.txt file entitled 02333365.txt, created on Jan. 5, 2016, and having a size of 44194 bytes. The content of the sequence listing is incorporated herein in its entirety.

BACKGROUND

Current techniques for identification of microbially produced chemicals, including biofuels, rely on chromatography-based screening assays. As such, these current techniques only allow for the processing of about $10^2$ samples per day. Therefore, there exists a need for improved compositions and techniques that can allow for greater and more efficient processing of samples.

BRIEF DESCRIPTION OF THE DRAWINGS

Further aspects of the present disclosure will be readily appreciated upon review of the detailed description of its various embodiments, described below, when taken in conjunction with the accompanying drawings.

Figure 15A:
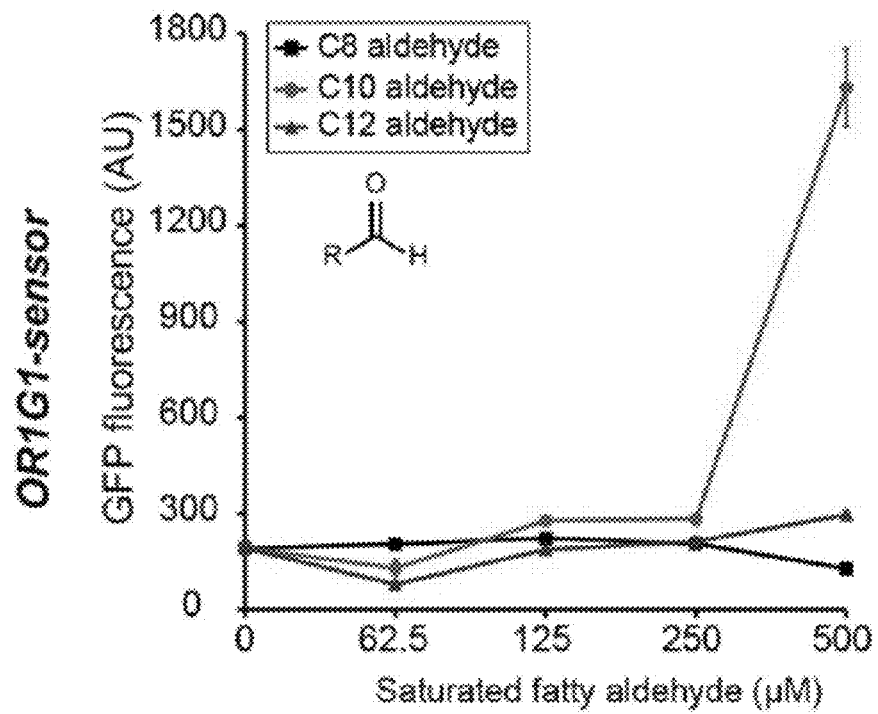
Figure 15B:
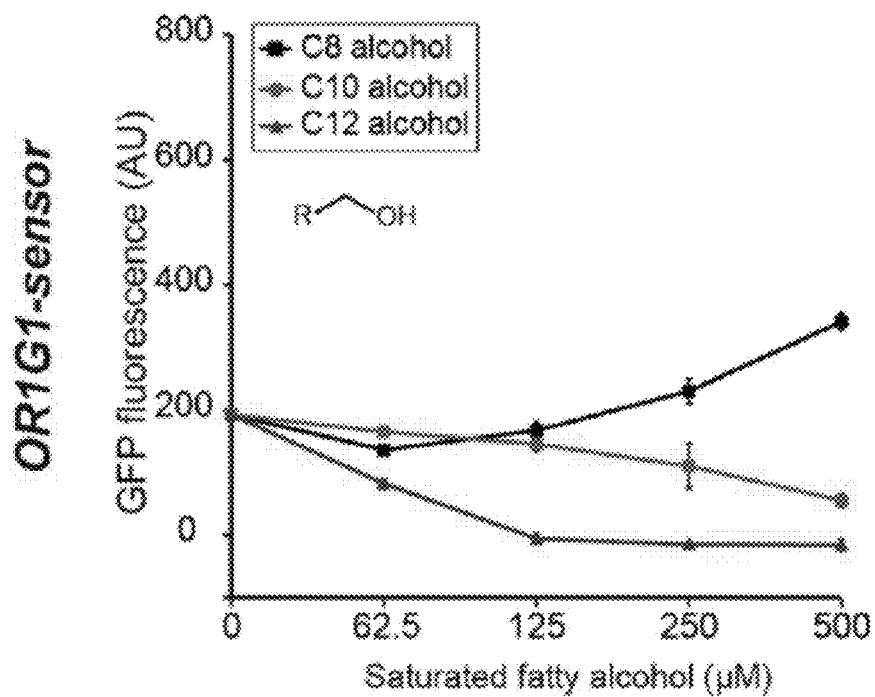
Figure 15C:
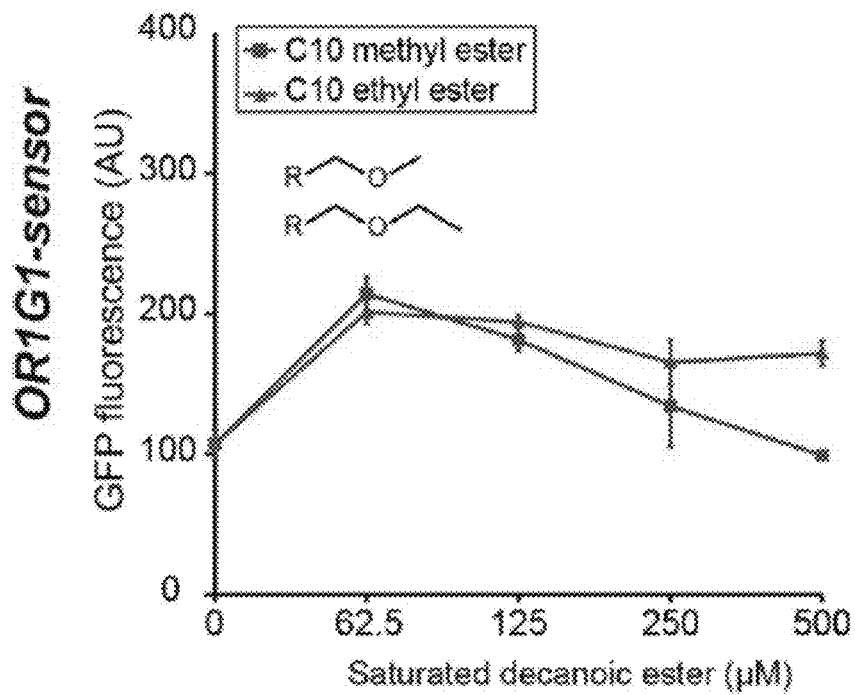

FIGS. 15A-15C show graphs demonstrating dose response curves for the OR1G1-based sensor with C8, C10 and C12 fatty aldehydes (FIG. 15A), alcohols (FIG. 15B) and C10 methyl- and ethyl-esters (FIG. 15C). All experiments were done in triplicate and the error bars represent the standard deviation from the mean.

Figure 16A:
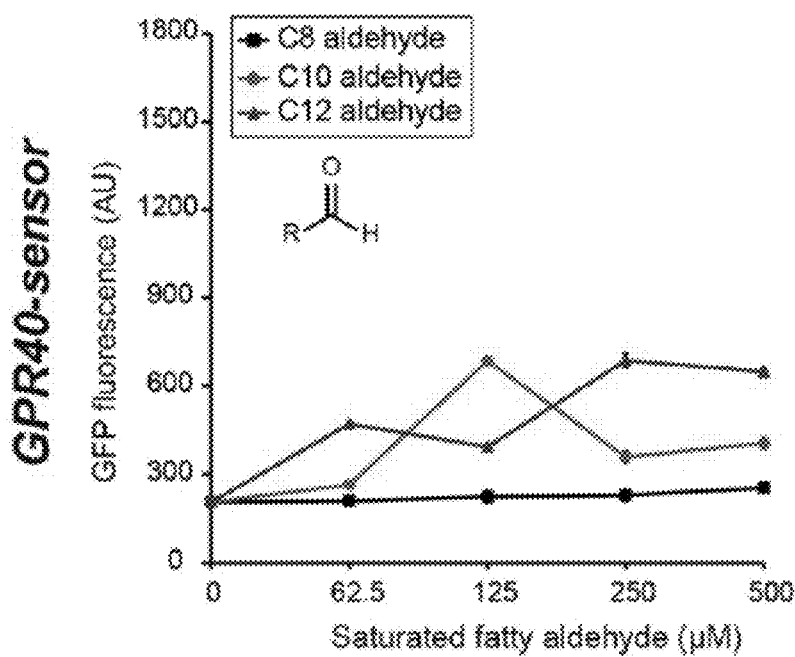
Figure 16B:
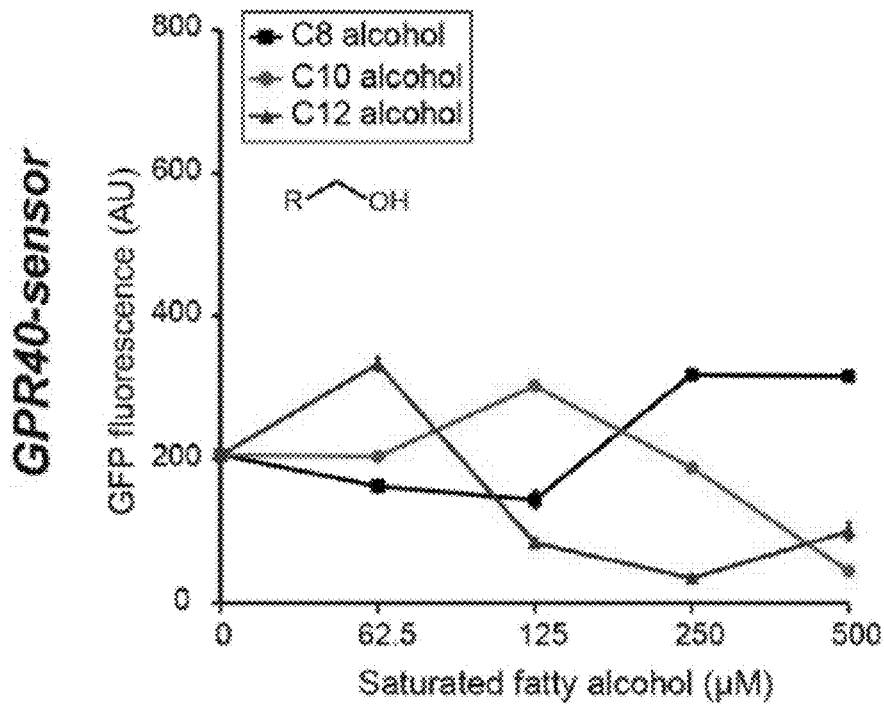
Figure 16C:
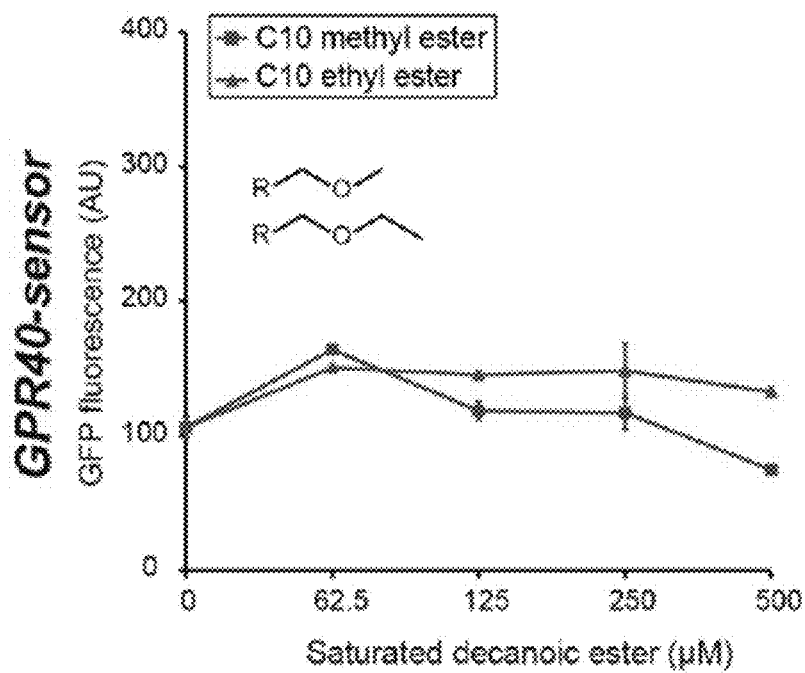

FIGS. 16A-16C show graphs demonstrating dose response curves for the GPR40-based sensor with C8, C10 and C12 fatty aldehydes (FIG. 16A), alcohols (FIG. 16B) and C10 methyl- and ethyl-esters (FIG. 16C). All experiments were done in triplicate and the error bars represent the standard deviation from the mean.

Figure 17:
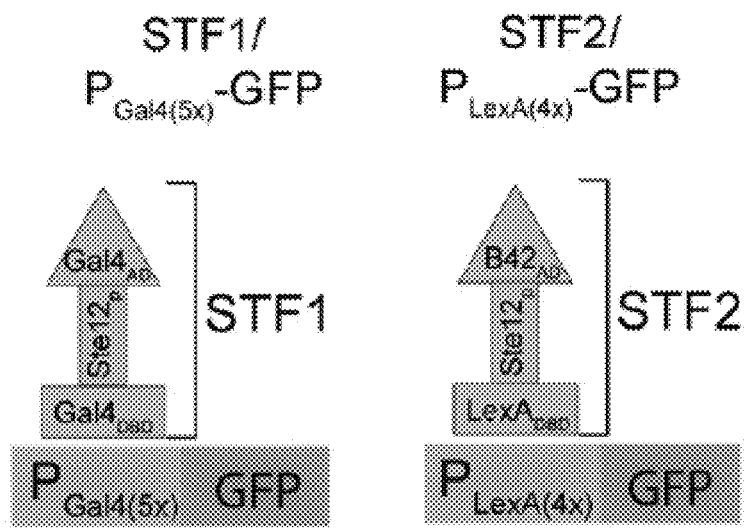

FIG. 17 shows a cartoon depicting embodiments of GPCR-based chemical biosensors having synthetic response units. Synthetic transcription factor (STF)/synthetic promoter composition. AD=activation domain. P=phosphorylation domain. DBD=DNA binding domain. STF1 is composed of a Gal4AD, Ste12p, and a Gal4DBD. STF1 binds to PGal4(5×), a synthetic promoter carrying five Gal4 DNA binding sites. STF2 can be composed of a B42AD, Ste12p, and a LexADBD. STF2 binds to PLexA (4×), a synthetic promoter carrying four lexA DNA binding sites.

Figure 18:
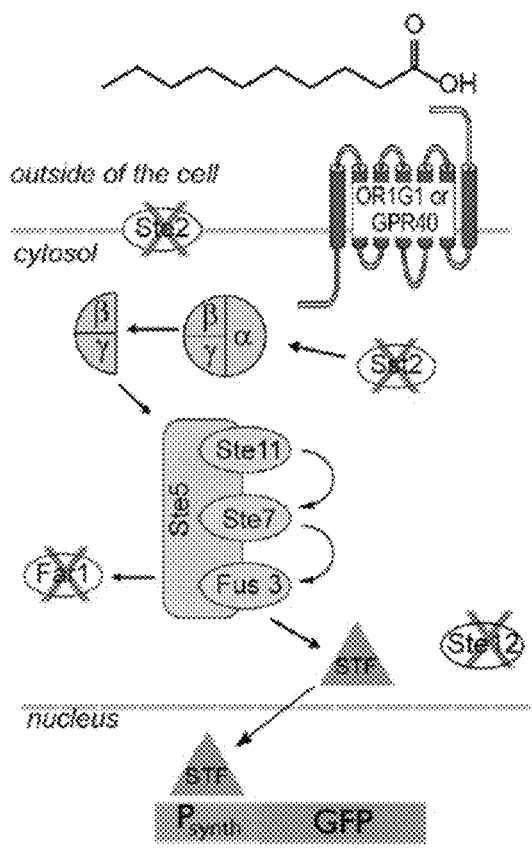

FIG. 18 shows a cartoon depicting embodiments of a GPCR-based chemical biosensor. Schematic of the OR1G1- and GPR40-based sensors use a synthetic response unit (STF/Psynthetic-GFP). In addition to deletion of the far1, sst2, and ste2 genes, the chemical sensor strain using a synthetic response unit can also have the endogenous transcription factor Ste12 deleted (W303 Δfar1, Δsst2, Δste2, Δste12).

Figure 19:
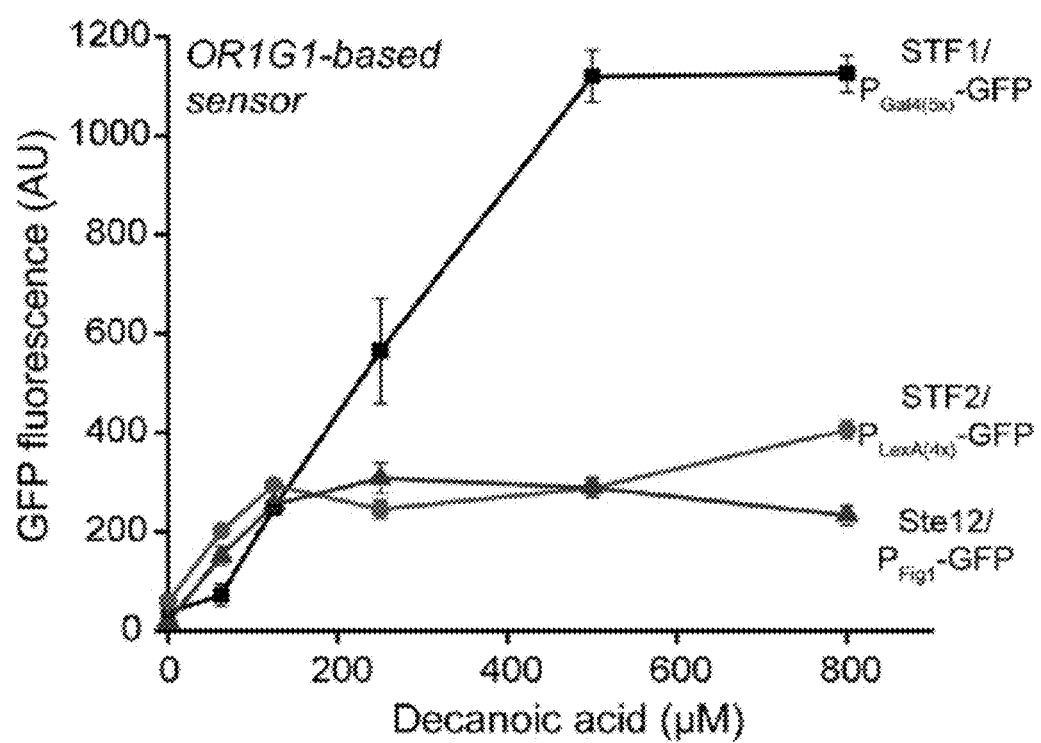

FIG. 19 shows a graph demonstrating dose response curves for decanoic acid using the OR1G1-based sensor coupled to Ste12/PFig1-GFP(s) (blue), STF1/PGal4(5×)-GFP (black), or STF2/PLexA(4×)-GFP (red) response units. All experiments were done in triplicate and the error bars represent the standard deviation from the mean. P-values, obtained from a two-tailed t test, are shown for statistically different samples.

Figure 20:
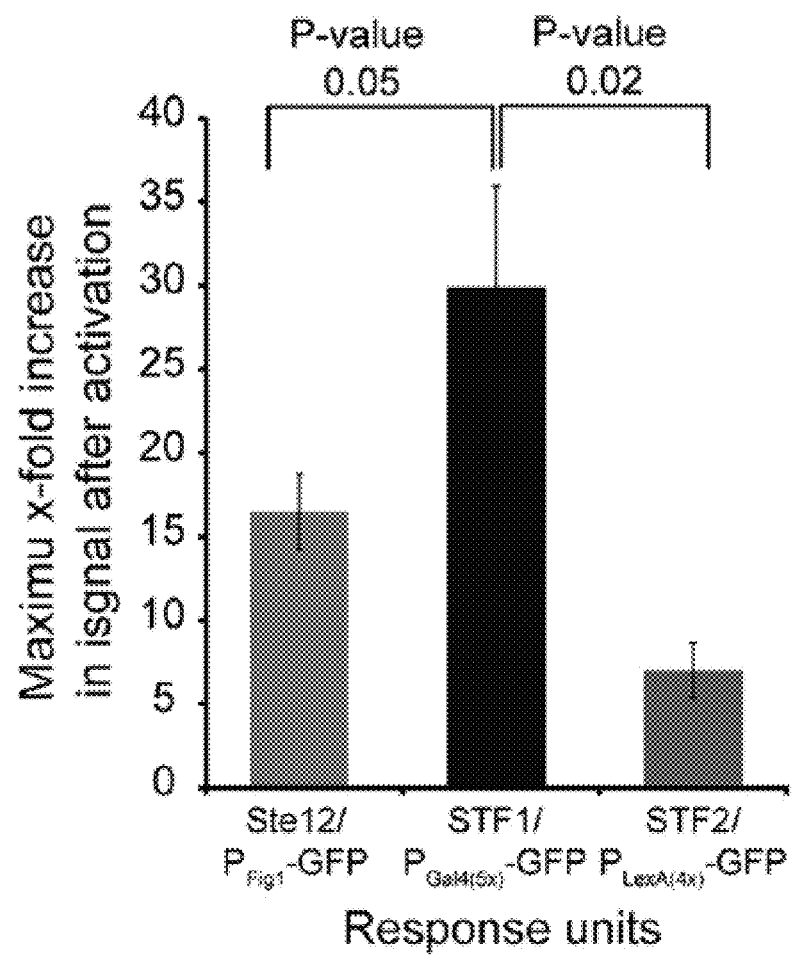

FIG. 20 shows a graph demonstrating OR1G1-based sensor maximum x-fold increase in signal after activation upon addition of decanoic acid when coupled to Ste12/PFig1-GFP(s): 250 μM C10 acid, STF1/PGal4(5×)-GFP: 800 μM C10 acid, and STF2/PLexA(4×)-GFP: 800 μM C10 acid. All experiments were done in triplicate and the error bars represent the standard deviation from the mean. P-values, obtained from a two-tailed t test, are shown for statistically different samples.

Figure 21:
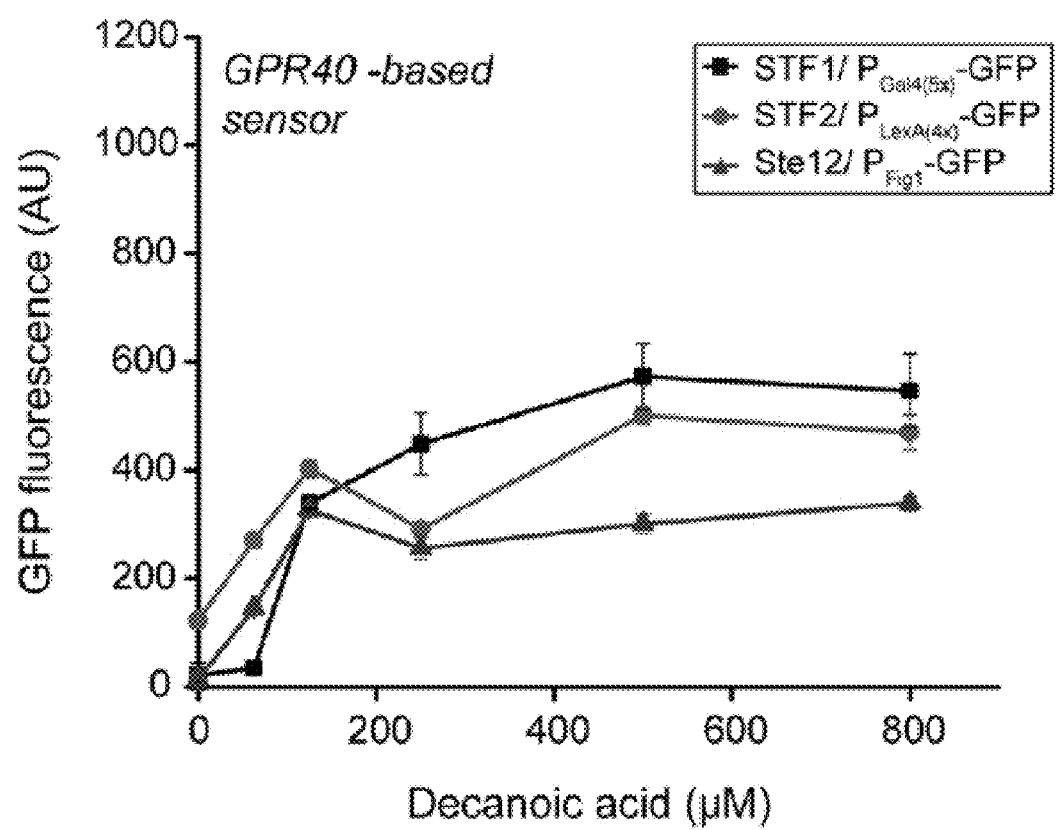

FIG. 21 shows a graph demonstrating dose response curves for decanoic acid using the GPR40-based sensor coupled to Ste12/PFig1-GFP(s) (blue), STF1/PGal4(5×)-GFP (black) or STF2/PLexA(4×)-GFP (red) response units. All experiments were done in triplicate and the error bars represent the standard deviation from the mean.

Figure 22:
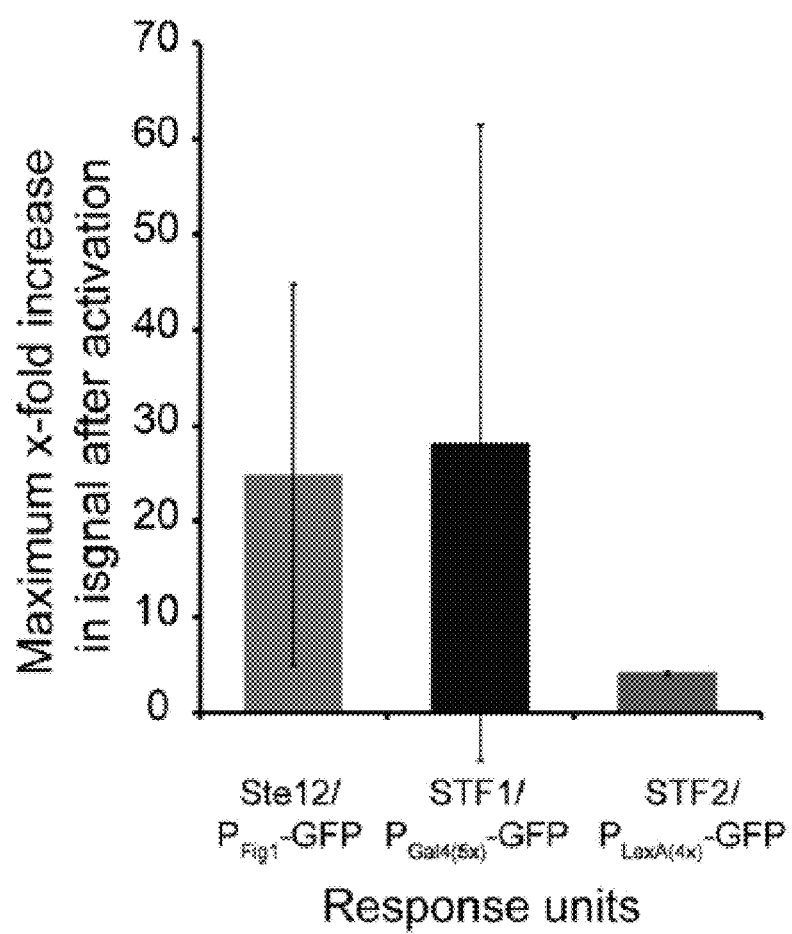

FIG. 22 shows a graph demonstrating GPR40-based sensor maximum x-fold increase in signal after activation upon addition of decanoic acid when coupled to Ste12/PFig1-GFP(s): 800 μM C10 acid, STF1/PGal4(5×)-GFP: 500 μM C10 acid, and STF2/PLexA(4×)-GFP: 500 μM C10 acid. P-values, obtained from a two-tailed t test, shown for statistically different samples. All experiments were done in triplicate and the error bars represent the standard deviation from the mean.

Figure 1:
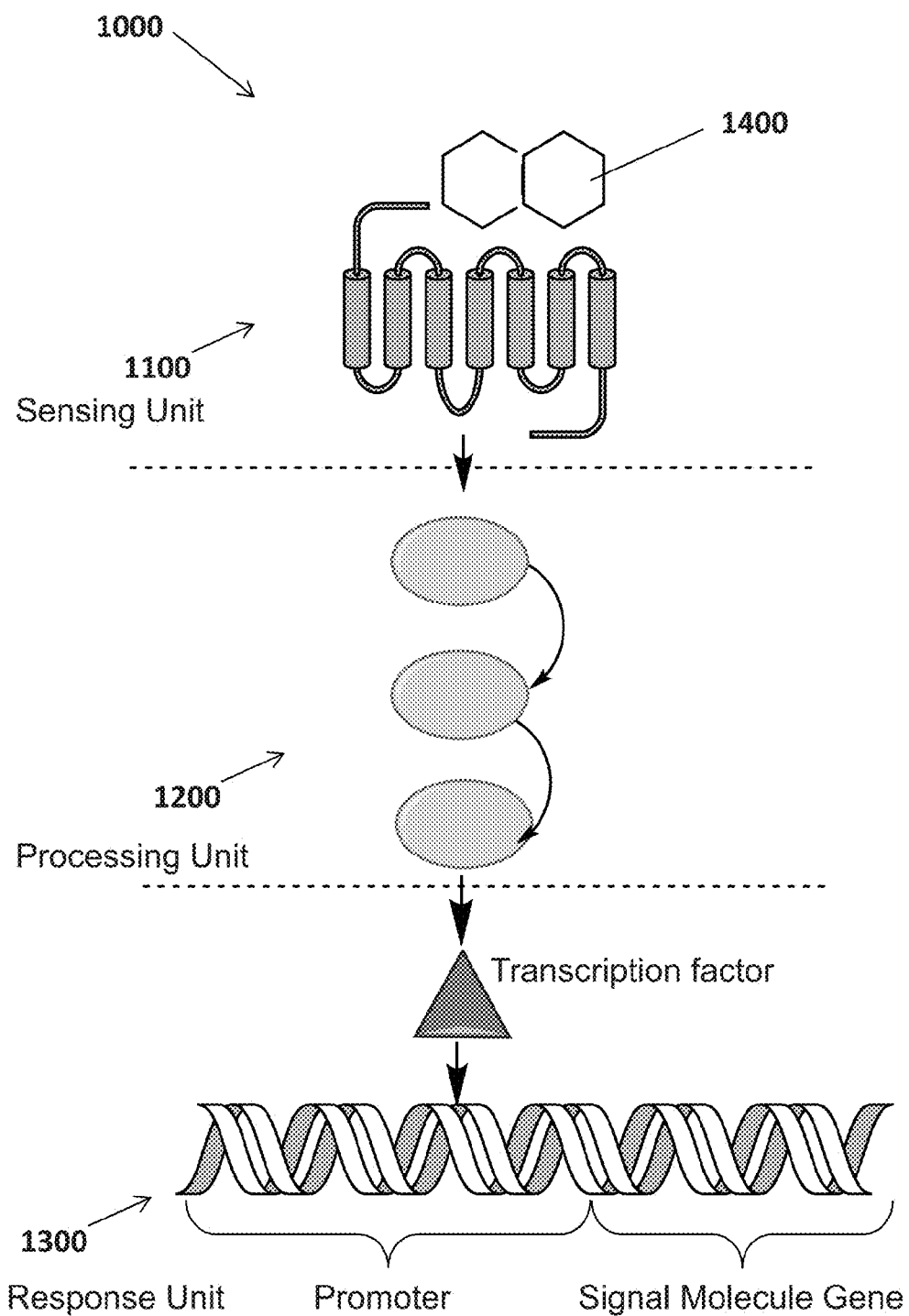
FIG. 1 shows one embodiment of a GPCR-based chemical biosensor.
Figure 23:
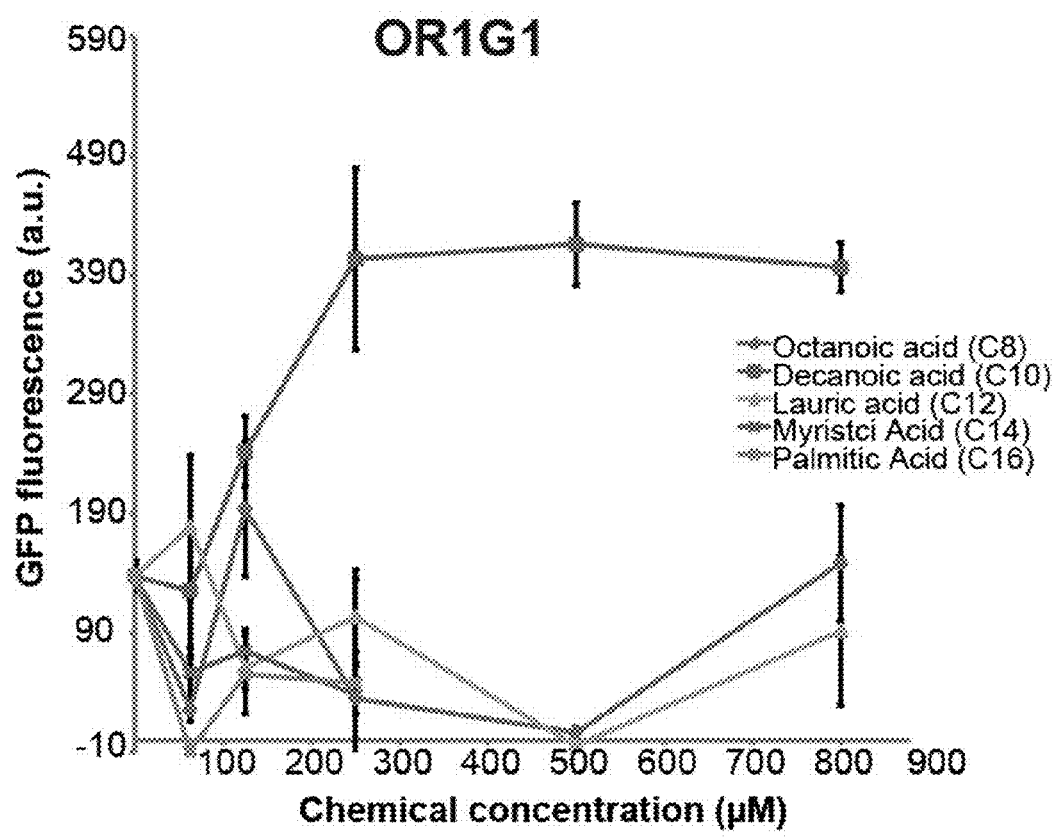

FIG. 23 is a graph demonstrating GFP fluorescence from OR1G1-based sensors with $P_{FIG1}$-GFP multi-copy reporter plasmid. The OR1G1 sensor had the following characteristics: (W303 Δfar1, Δsst2, Δste2, pESC-His3-$P_{TEF1}$-OR1G1, pESC-Leu2-$P_{FIG1}$-GFP).

Figure 24:
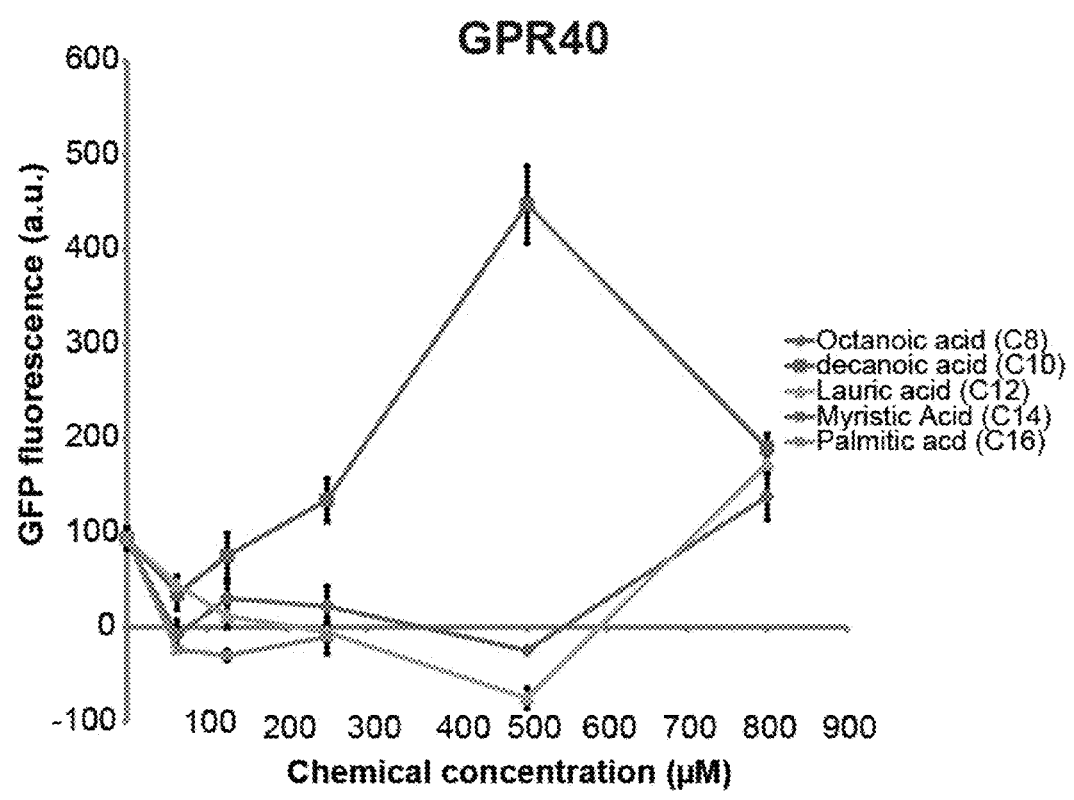

FIG. 24 is a graph demonstrating GFP fluorescence from GPR40-based sensors with $P_{FIG1}$-GFP multi-copy reporter plasmid. The GPR40 sensor had the following characteristics: (W303 Δfar1, Δsst2, Δste2, pESC-His3-$P_{TEF1}$-GPR40, pESC-Leu2-$P_{FIG1}$-GFP).

Figure 25:
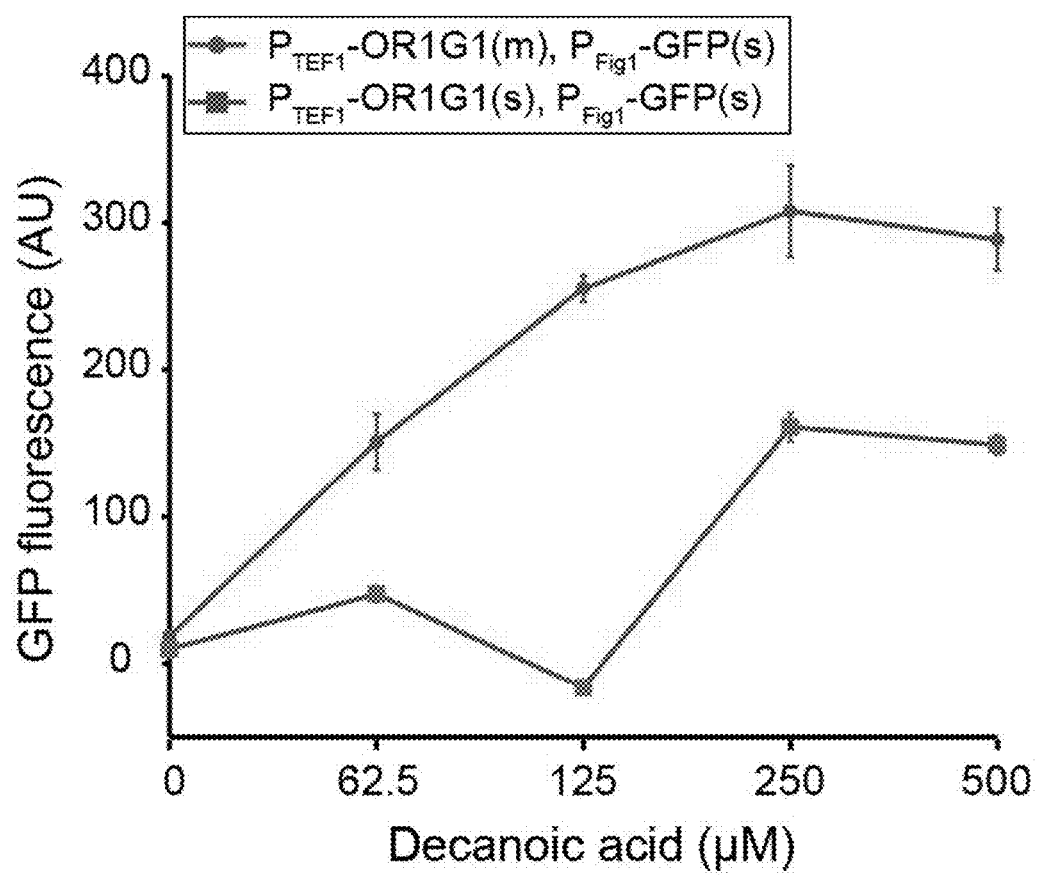

FIG. 25 is a graph demonstrating OR1G1-based sensor decanoic acid response curves when the OR1 G1 GPCR is expressed from a multi- or a single-copy plasmid.

Figure 26:
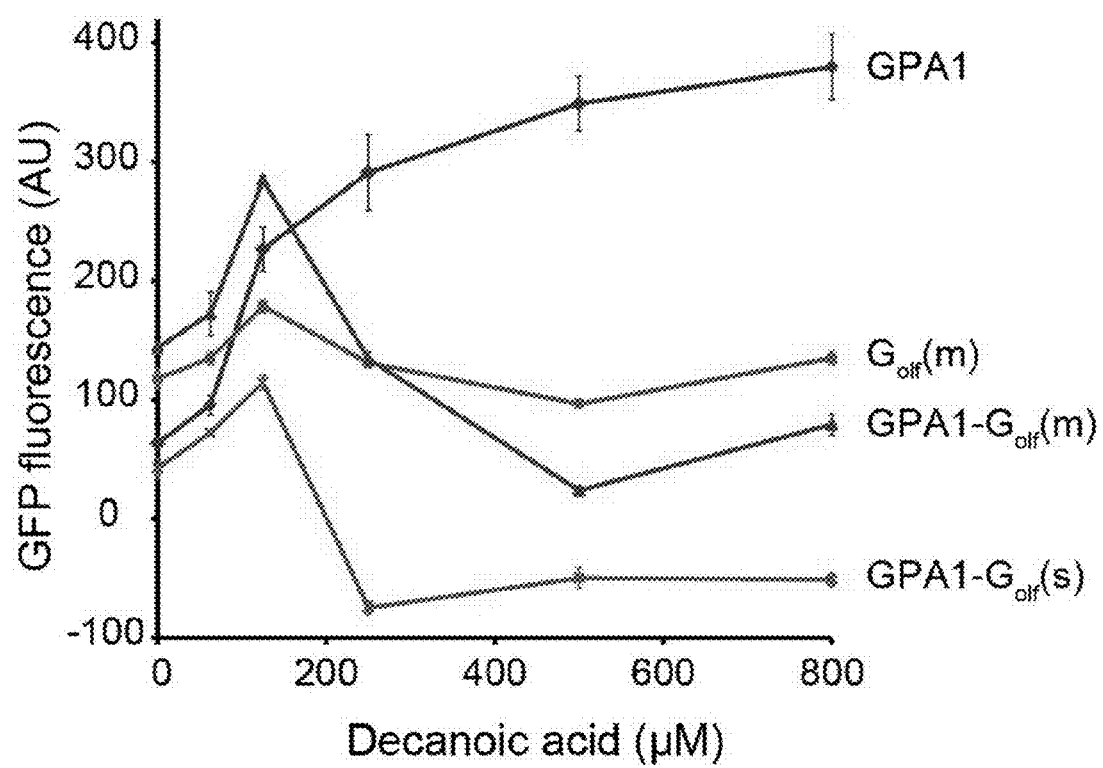

FIG. 26 is a graph demonstrating OR1G1-based sensor decanoic acid response curves when signaling through the endogenous yeast Gα subunit expressed from the chromosome (GPA1), the mammalian olfactory Gα subunit from a multi-copy plasmid ($G_{olf}$(m)), a hybrid yeast/mammalian Gα subunit composed of GPA1 carrying the five C-terminal amino acids from $G_{olf}$ from a multi-(GPA1-$G_{olf}$(m)) or a single-copy plasmid (GPA1-$G_{olf}$(m)).

Figure 27:
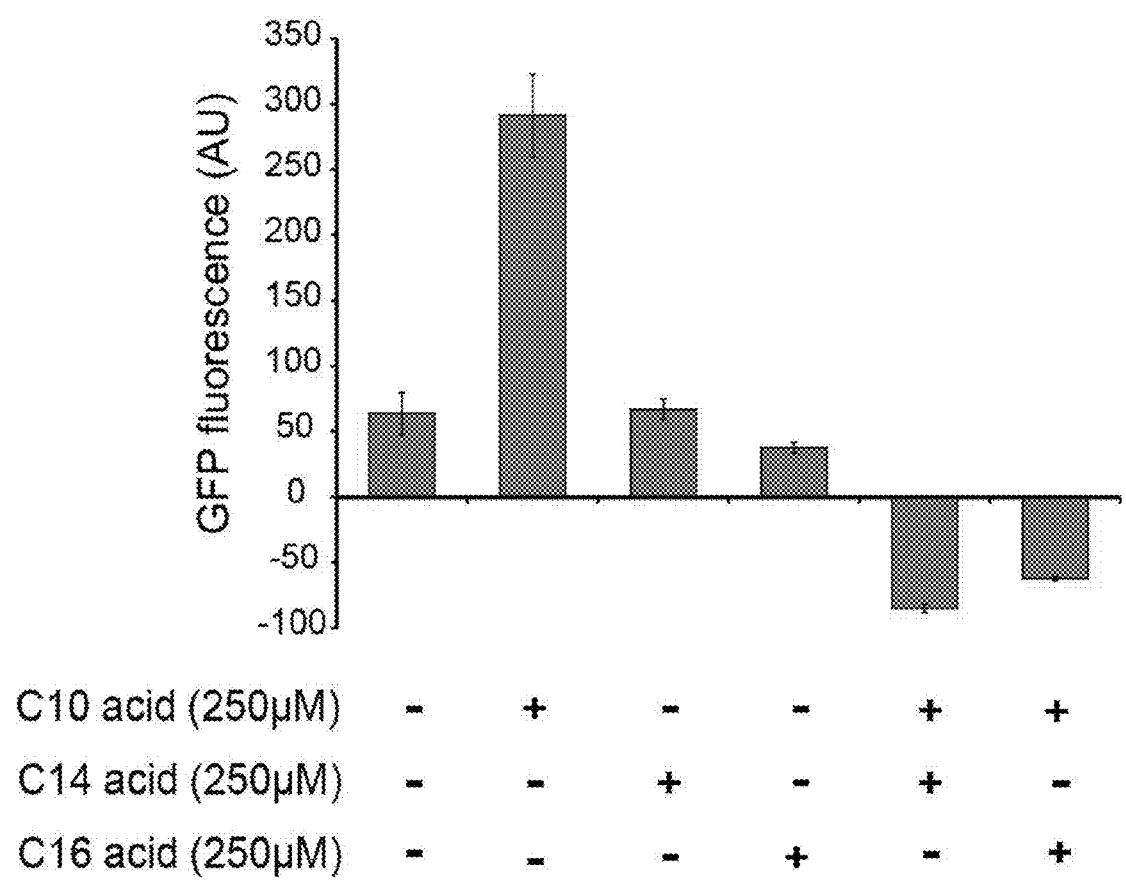

FIG. 27 shows a graph demonstrating OR1G1-sensor performance in a mixture of fatty acids. Although the OR1G1-sensor is able to detect C10, C14 and C16 acids at 250 μM independently, it is not able to detect them in a mixture of acids.

Figure 28A:
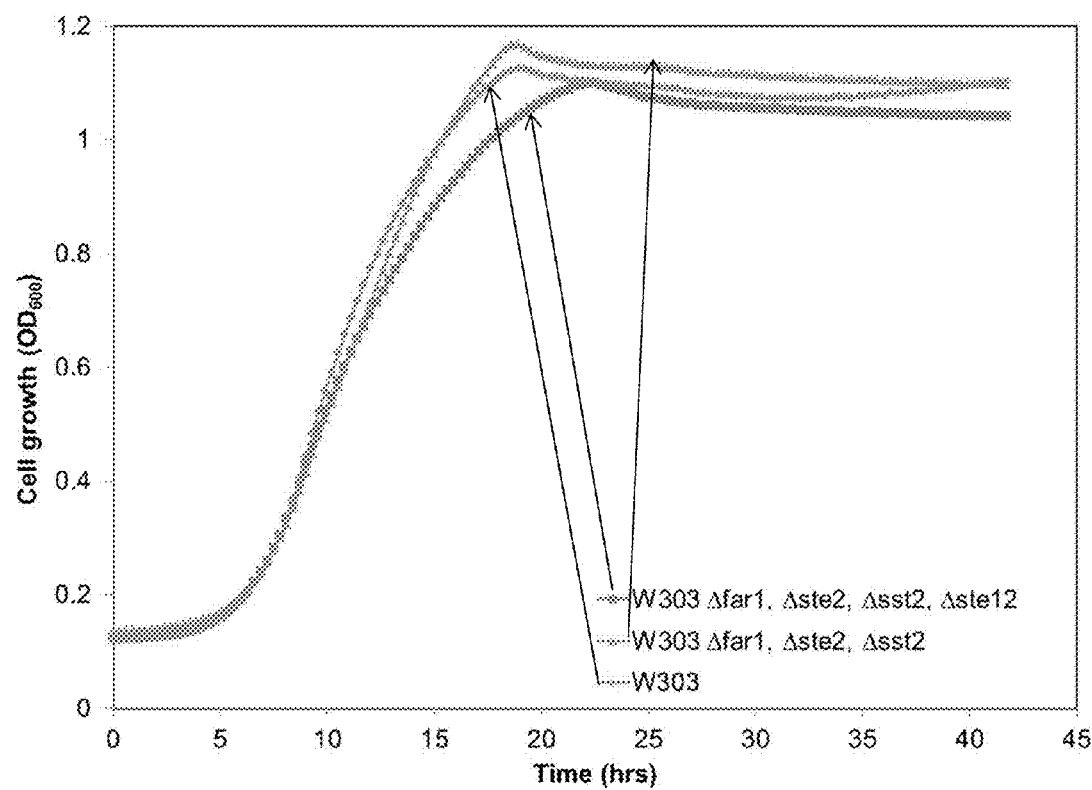
Figure 28B:
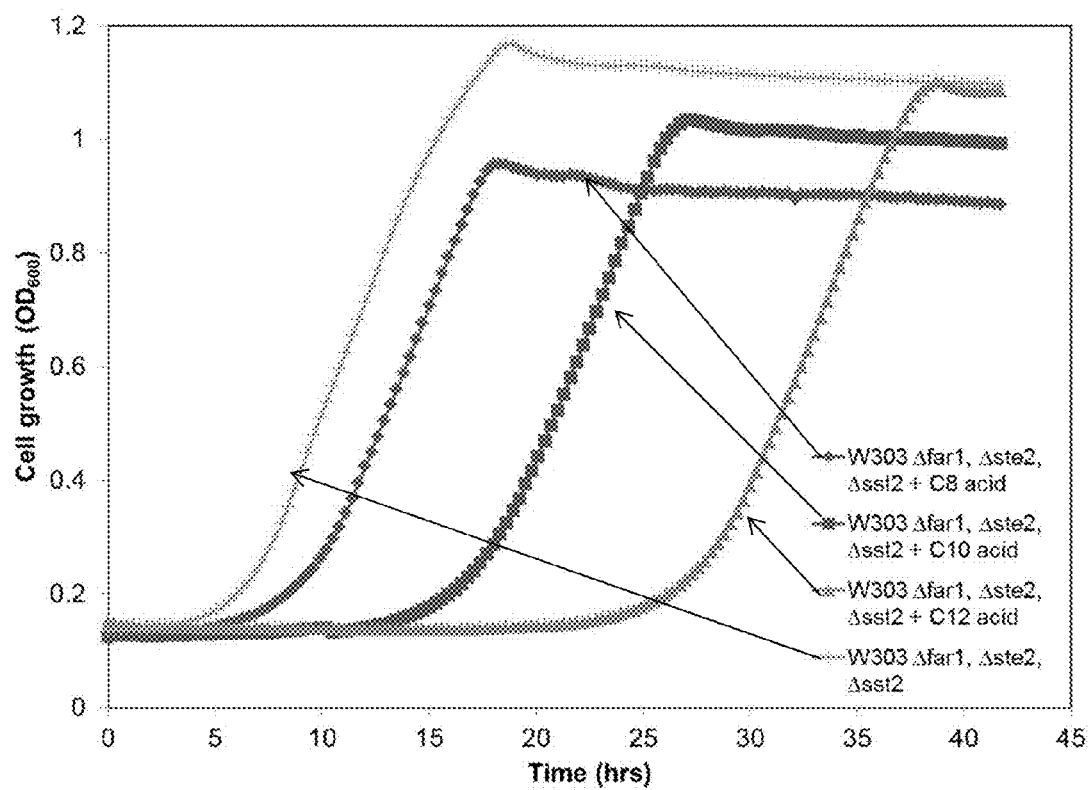
Figure 28C:
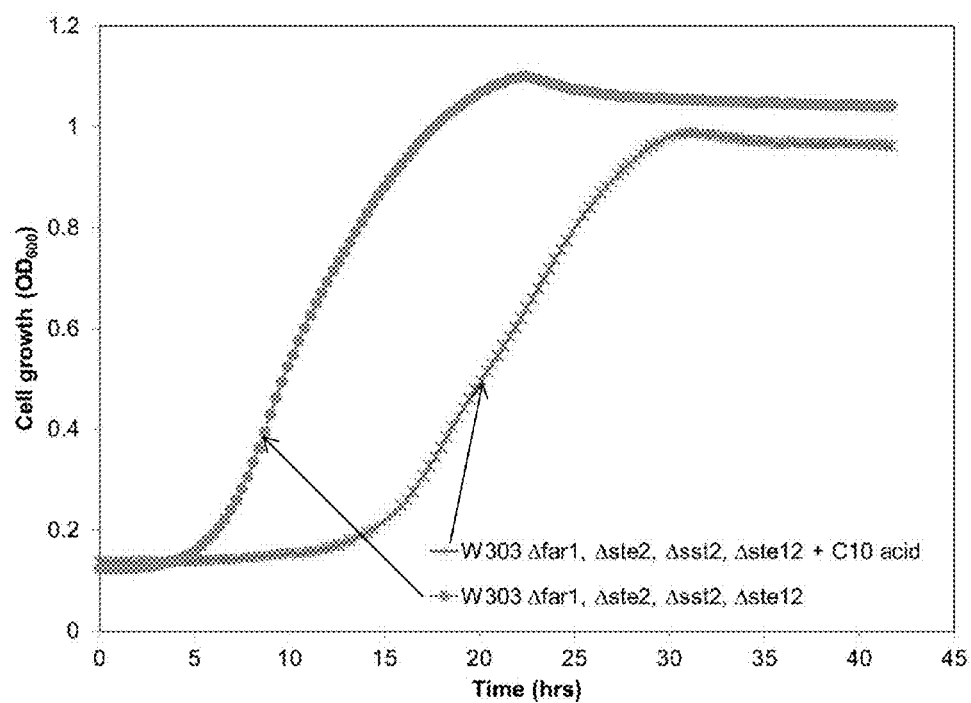
Figure 29A:
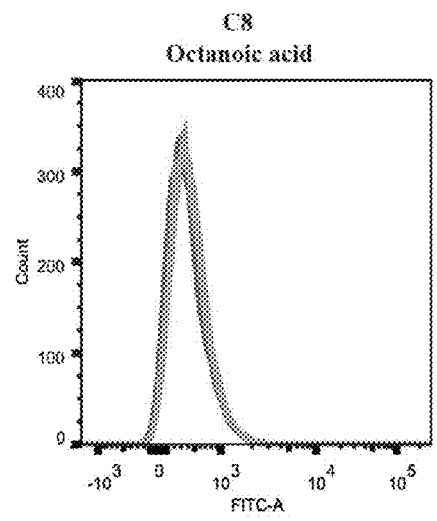
Figure 29B:
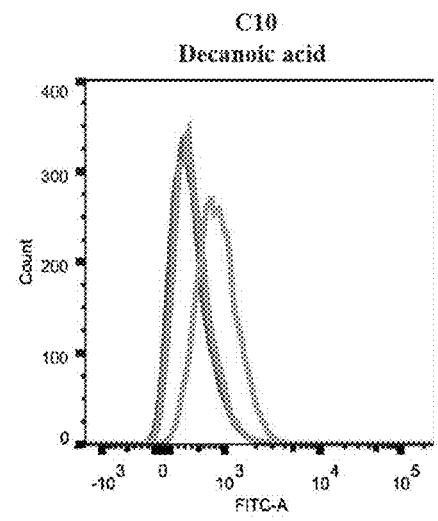
Figure 29C:
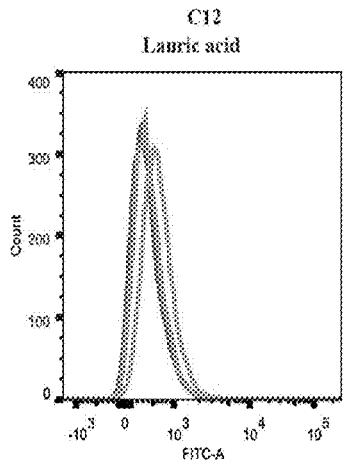
Figure 29D:
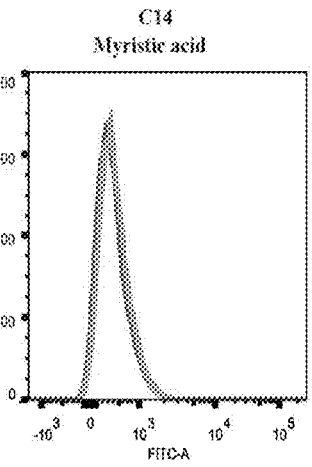
Figure 29E:
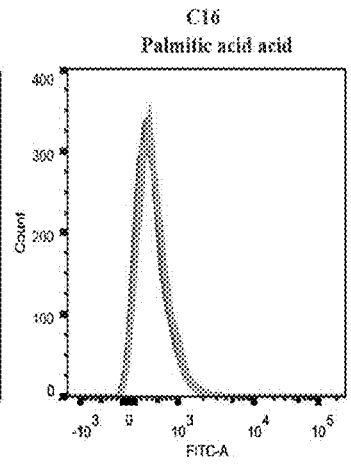
Figures 30A, 30B:
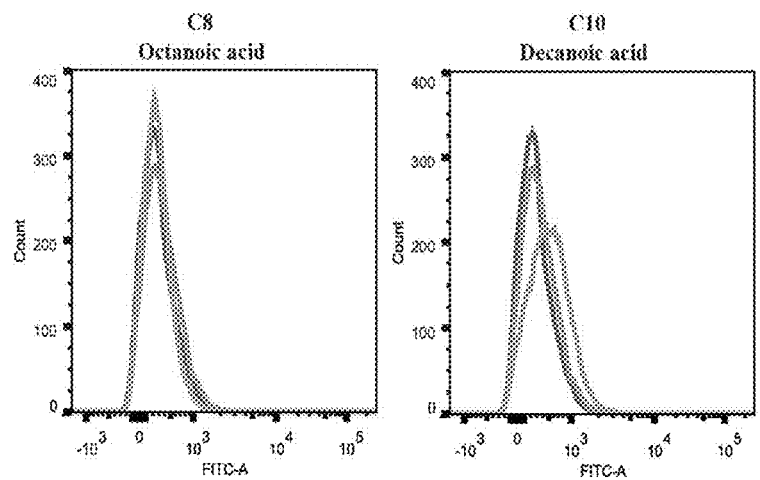
Figures 30C, 30D, 30E:
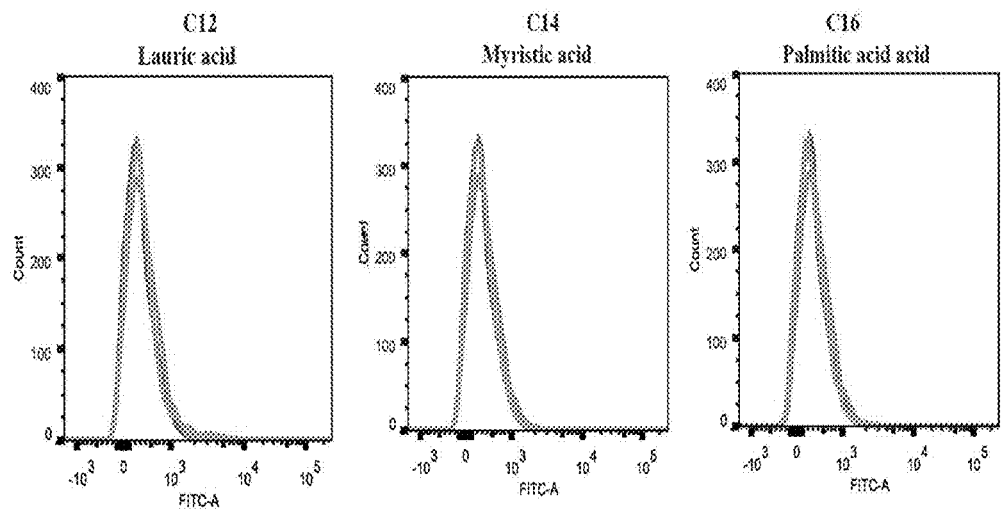

FIGS. 28A-28C show cell growth of the sensor strain (28A). Fatty acid toxicity to the sensor strains (28B-28C). Importantly, the growth rate of the sensor is similar to the wild type strain.

FIGS. 29A-29E show sample flow cytometry histograms of the biosensor strain when incubated with different compounds when using GPCR-based sensor OR1G1. A shift in the population when incubating with C8-C12 (orange line) was observed. Blue lines indicate the sensor when no compound is added. Red line indicates cell autofluorescence.

FIGS. 30A-30E show flow cytometry histograms of the biosensor strain when incubated with different compounds when using GPCR-based sensor GPR40. A shift of the population when incubating with decanoic acid (orange line) was observed. Blue lines are sensor when no compound is added. Red line represents cell autofluorescence.

Figure 31:
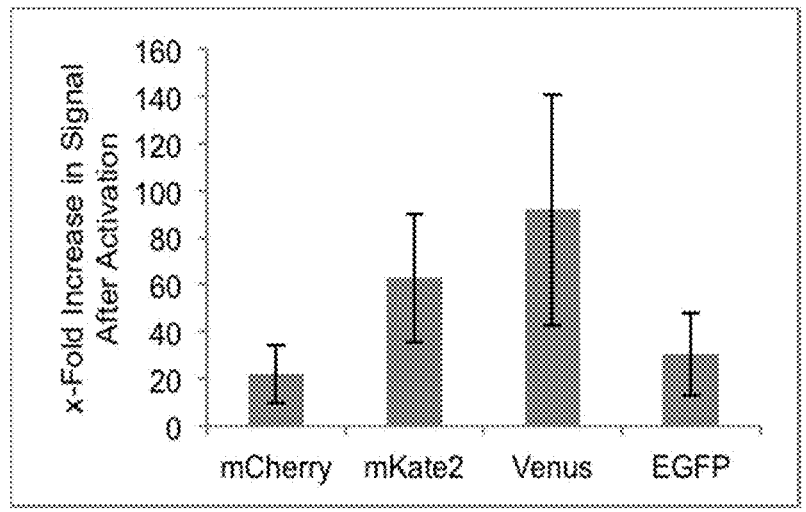

FIG. 31 shows a graph demonstrating endogenous GPCR (Ste2/alpha-factor) x-fold increase in signal after activation 4 hours after addition of 100 nM of α-factor.

Figure 32:
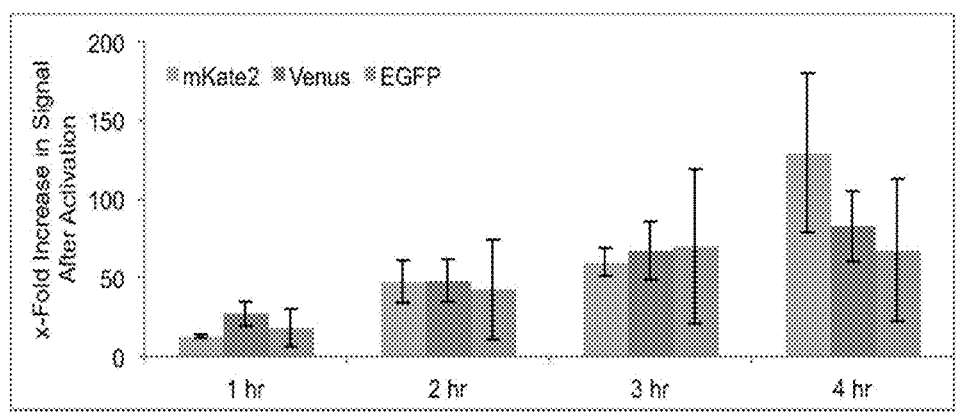

FIG. 32 shows a graph demonstrating endogenous GPCR (Ste2/alpha-factor) x-fold increase in signal with 100 nM of α-factor at different time points. The fluorescence was measured after 1, 2, 3, and 4 hours.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, nanotechnology, organic chemistry, synthetic biology, chemistry, biochemistry, botany and the like, which are within the skill of the art. Such techniques are explained fully in the literature.

Definitions

As used herein, "about," "approximately," and the like, when used in connection with a numerical variable, generally refers to the value of the variable and to all values of the variable that are within the experimental error (e.g., within the 95% confidence interval for the mean) or within ±10% of the indicated value, whichever is greater.

As used herein, "control" is an alternative subject or sample used in an experiment for comparison purposes and included to minimize or distinguish the effect of variables other than an independent variable.

As used herein, "specifically binds" or "specific binding" refers to binding that occurs between such paired species such as enzyme/substrate, receptor/agonist or antagonist, antibody/antigen, lectin/carbohydrate, oligo DNA primers/DNA, enzyme or protein/DNA, and/or RNA molecule to other nucleic acid (DNA or RNA) or amino acid, which may be mediated by covalent or non-covalent interactions or a combination of covalent and non-covalent interactions. When the interaction of the two species produces a non-covalently bound complex, the binding that occurs is typically electrostatic, hydrogen-bonding, or the result of lipophilic interactions. Accordingly, "specific binding" occurs between a paired species where there is interaction between the two which produces a bound complex having the characteristics of an antibody/antigen, enzyme/substrate, DNA/DNA, DNA/RNA, DNA/protein, RNA/protein, RNA/amino acid, receptor/substrate interaction. In particular, the specific binding is characterized by the binding of one member of a pair to a particular species and to no other species within the family of compounds to which the corresponding member of the binding member belongs. Thus, for example, an antibody preferably binds to a single epitope and to no other epitope within the family of proteins.

As used herein, "overexpressed" or "overexpression" refers to an increased expression level of an RNA or protein product encoded by a gene as compared to the level of expression of the RNA or protein product in a normal or control cell.

As used herein, "underexpressed" or "underexpression" refers to decreased expression level of an RNA or protein product encoded by a gene as compared to the level of expression of the RNA or protein product in a normal or control cell.

As used herein, "expression" refers to the process by which polynucleotides are transcribed into RNA transcripts. In the context of mRNA and other translated RNA species, "expression" also refers to the process or processes by which the transcribed RNA is subsequently translated into peptides, polypeptides, or proteins.

As used herein, gene deletion refers to a mutation introduced into the genome of an organism that completely or partially removes a physical portion of the nucleotide sequence for the gene to disrupt the production of a gene product generated from that gene or otherwise disrupts and/or ablates the production of the product of that gene. Deletions can be said to result in gene knockout or knockdown. Deletions can be homozygous (both or all copies deleted), heterozygous (only one or less than all copies deleted), or hemizygous.

As used herein, "nucleic acid" and "polynucleotide" generally refer to a string of at least two base-sugar-phosphate combinations and refers to, among others, single- and double-stranded DNA, DNA that is a mixture of single- and double-stranded regions, single- and double-stranded RNA, and RNA that is mixture of single- and double-stranded regions, as well as hybrid molecules comprising DNA and RNA that may be single-stranded or, more typically, double-stranded or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. "Polynucleotide" and "nucleic acids" also encompasses such chemically, enzymatically or metabolically modified forms of polynucleotides, as well as the chemical forms of DNA and RNA characteristic of viruses and cells, including simple and complex cells, inter alia. For instance, the term polynucleotide includes DNAs or RNAs as described above that contain one or more modified bases. Thus, DNAs or RNAs comprising unusual bases, such as inosine, or modified bases, such as tritylated bases, to name just two examples, are polynucleotides as the term is used herein. "Polynucleotide" and "nucleic acids" also includes PNAs (peptide nucleic acids), phosphorothioates, and other variants of the phosphate backbone of native nucleic acids. Natural nucleic acids have a phosphate backbone, and artificial nucleic acids may contain other types of backbones, but contain the same bases. Thus, DNAs or RNAs with backbones modified for stability or for other reasons are "nucleic acids" or "polynucleotide" as that term is intended herein.

As used herein, "deoxyribonucleic acid (DNA)" and "ribonucleic acid (RNA)" generally refer to any polyribonucleotide or polydeoxribonucleotide, which may be unmodified RNA or DNA or modified RNA or DNA. RNA may be in the form of a tRNA (transfer RNA), snRNA (small nuclear RNA), rRNA (ribosomal RNA), mRNA (messenger RNA), anti-sense RNA, RNAi (RNA interference construct), siRNA (short interfering RNA), or ribozymes.

As used herein, "nucleic acid sequence" and "oligonucleotide" also encompasses a nucleic acid and polynucleotide as defined above.

As used herein, "DNA molecule" includes nucleic acids/polynucleotides that are made of DNA.

As used herein, "wild-type" is the typical form of an organism, variety, strain, gene, protein, or characteristic as it occurs in nature, as distinguished from mutant forms that may result from selective breeding or transformation with a transgene.

As used herein, "identity" is a relationship between two or more polypeptide or polynucleotide sequences, as determined by comparing the sequences. In the art, "identity" also refers to the degree of sequence relatedness between polypeptide as determined by the match between strings of such sequences. "Identity" can be readily calculated by known methods, including, but not limited to, those described in Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J. Applied Math. 1988, 48: 1073. Preferred methods to determine identity are designed to give the largest match between the sequences tested. Methods to determine identity are codified in publicly available computer programs. The percent identity between two sequences can be determined by using analysis software (e.g., Sequence Analysis Software Package of the Genetics Computer Group, Madison Wis.) that incorporates the Needelman and Wunsch (J. Mol. Biol., 1970, 48: 443-453) algorithm (e.g., NBLAST, and XBLAST). The default parameters are used to determine the identity for the polypeptides or polynucleotides of the present disclosure.

As used herein, "heterologous" refers to compounds, molecules, nucleotide sequences (including genes), and polypeptide sequences (including peptides and proteins) that are different in both activity (function) and sequence or chemical structure. As used herein, "heterologous" can also refer to a gene or gene product that is from a different organism. For example, a human GPCR can be said to be heterologous when expressed in yeast.

As used herein, "homologue" refers to a polypeptide sequence that shares a threshold level of similarity and/or identity as determined by alignment of matching amino acids. Two or more polypeptides determined to be homologues are said to be homologues. Homology is a qualitative term that describes the relationship between polypeptide sequences that is based upon the quantitative similarity.

As used herein, "paralog" refers to a homologue produced via gene duplication of a gene. In other words, paralogs are homologues that result from divergent evolution from a common ancestral gene.

As used herein, "orthologues" refers to homologues produced by speciation followed by divergence of sequence but not activity in separate species. When speciation follows duplication and one homologue sorts with one species and the other copy sorts with the other species, subsequent divergence of the duplicated sequence is associated with one or the other species. Such species specific homologues are referred to herein as orthologues.

As used herein, "xenologs" are homologues resulting from horizontal gene transfer.

As used herein, "similarity" is a quantitative term that defines the degree of sequence match between two compared polypeptide sequences.

As used herein, "cell," "cell line," and "cell culture" include progeny. It is also understood that all progeny may not be precisely identical in DNA content, due to deliberate or inadvertent mutations. Variant progeny that have the same function or biological property, as screened for in the originally transformed cell, are included.

As used herein, "culturing" refers to maintaining cells under conditions in which they can proliferate and avoid senescence as a group of cells. "Culturing" can also include conditions in which the cells also or alternatively differentiate.

As used herein, "organism," "host," and "subject" refers to any living entity comprised of at least one cell. A living organism can be as simple as, for example, a single isolated eukaryotic cell or cultured cell or cell line, or as complex as a mammal, including a human being, and animals (e.g., vertebrates, amphibians, fish, mammals, e.g., cats, dogs, horses, pigs, cows, sheep, rodents, rabbits, squirrels, bears, primates (e.g., chimpanzees, gorillas, and humans). "Subject" may also be a cell, a population of cells, a tissue, an organ, or an organism, preferably to human and constituents thereof.

As used herein, "gene" refers to a hereditary unit corresponding to a sequence of DNA that occupies a specific location on a chromosome and that contains the genetic instruction for a characteristic(s) or trait(s) in an organism.

As used herein, the term "recombinant" generally refers to a non-naturally occurring nucleic acid, nucleic acid construct, or polypeptide. Such non-naturally occurring nucleic acids may include natural nucleic acids that have been modified, for example that have deletions, substitutions, inversions, insertions, etc., and/or combinations of nucleic acid sequences of different origin that are joined using molecular biology technologies (e.g., a nucleic acid sequences encoding a fusion protein (e.g., a protein or polypeptide formed from the combination of two different proteins or protein fragments), the combination of a nucleic acid encoding a polypeptide to a promoter sequence, where the coding sequence and promoter sequence are from different sources or otherwise do not typically occur together naturally (e.g., a nucleic acid and a constitutive promoter), etc.). Recombinant also refers to the polypeptide encoded by the recombinant nucleic acid. Non-naturally occurring nucleic acids or polypeptides include nucleic acids and polypeptides modified by man.

As used herein, "plasmid" refers to a non-chromosomal double-stranded DNA sequence including an intact "replicon" such that the plasmid is replicated in a host cell.

As used herein, the term "vector" is used in reference to a vehicle used to introduce an exogenous nucleic acid sequence into a cell. A vector may include a DNA molecule, linear or circular (e.g. plasmids), which includes a segment encoding a polypeptide of interest operatively linked to additional segments that provide for its transcription and translation upon introduction into a host cell or host cell organelles. Such additional segments may include promoter and terminator sequences, and may also include one or more origins of replication, one or more selectable markers, an enhancer, a polyadenylation signal, etc. Expression vectors are generally derived from yeast or bacterial genomic or plasmid DNA, or viral DNA, or may contain elements of both.

As used herein, "operatively linked" indicates that the regulatory sequences useful for expression of the coding sequences of a nucleic acid are placed in the nucleic acid molecule in the appropriate positions relative to the coding sequence so as to effect expression of the coding sequence. This same definition is sometimes applied to the arrangement of coding sequences and transcription control elements (e.g. promoters, enhancers, and termination elements), and/or selectable markers in an expression vector.

As used herein, "cDNA" refers to a DNA sequence that is complementary to a RNA transcript in a cell. It is a man-made molecule. Typically, cDNA is made in vitro by an enzyme called reverse-transcriptase using RNA transcripts as templates.

As used herein, the term "transfection" refers to the introduction of an exogenous and/or recombinant nucleic acid sequence into the interior of a membrane enclosed space of a living cell, including introduction of the nucleic acid sequence into the cytosol of a cell as well as the interior space of a mitochondria, nucleus, or chloroplast. The nucleic acid may be in the form of naked DNA or RNA, it may be associated with various proteins or regulatory elements (e.g., a promoter and/or signal element), or the nucleic acid may be incorporated into a vector or a chromosome.

As used herein, "transformation" or "transformed" refers to the introduction of a nucleic acid (e.g., DNA or RNA) into cells in such a way as to allow expression of the coding portions of the introduced nucleic acid.

As used herein, "stable expression," "stable incorporation," "stable transfection" and the like refer to the integration of an exogenous gene into the genome of a host cell, which can allow for long term expression of the exogenous gene.

As used herein, "transient expression," "transient transfection," and the like refer to the introduction of an exogenous gene into a host cell that does not result in stable incorporation of the gene into the host cell.

As used herein "chemical" refers to any molecule, compound, particle, or other substance that can be a substrate for a G-protein coupled receptor. As such, "chemical" can refer to nucleic acids, proteins, organic compounds, inorganic compounds, etc.

As used herein "biologically coupled" refers to the association of or interaction between two or more physically distinct molecules, groups of molecules compounds, organisms, or particles where the association is directly or indirectly mediated between the two or more physically distinct molecules, groups of molecules compounds, organisms or particles via a biologic molecule or compound. This can include direct binding between two biologic molecules and signal transduction pathways.

As used herein, "biological communication" refers to the communication between two or more molecules, compounds, or objects that is mediated by a biologic molecule or biologic interaction.

As used herein, "biologic molecule," "biomolecule," and the like refer to any molecule that is present in a living organism and includes without limitation, macromolecules (e.g. proteins, polysaccharides, lipids, and nucleic acids) as well as small molecules (e.g. metabolites and other products produced by a living organism).

As used herein, a "biologic interaction" refers to the interaction between two biomolecules.

As used herein, "regulation" refers to the control of gene or protein expression or function.

As used herein, "signaling molecule" refers to a molecule, such as a biomolecule, capable of producing a measurable signal when expressed. The signal can be qualitative or quantitative. The signal can be measured by any suitable techniques, which will be instantly appreciated by those of skill in the art.

As used herein, "promoter" refers to the DNA sequence(s) that control or otherwise modify transcription of a gene and can include binding sites for transcription factors, RNA polymerases, and other biomolecules and substances (e.g. inorganic compounds) that can influence transcription of a gene by interaction with the promoter. Typically these sequences are located at the 5' end of the sense strand of the gene, but can be located anywhere in the genome.

As used herein, "native" refers to the endogenous version of a molecule or compound relative to the host cell or population being described.

As used herein, "non-naturally occurring" refers to a non-native version of a molecule or compound or non-native expression or presence of a molecule or compound within a host cell or other composition. This can include where a native molecule or compound is influenced to be expressed or present at a different location within a host, at a non-native period of time within a host, or is otherwise in an altered environment, even when considered within the host. Non-limiting examples include where a protein that is expressed only in the nucleus of a cell is expressed in the cytoplasm of the cell or when a protein that is only normally expressed during the embryonic stage of development is expressed during the adult stage.

As used herein, "encode" refers to the biologic phenomena of transcribing DNA into an RNA that, in some cases, can be translated into a protein product. As such, when a protein is said herein to be encoded by a particular nucleotide sequence, it is to be understood that this refers to this biologic relationship between DNA and protein. It is well established that RNA can be translated into protein based on the triplet code where 3 nucleotides represent an amino acid. This term also includes the idea that DNA can be transcribed into RNA molecules with biologic functions, such as ribozymes and interfering RNA species. As such, when a RNA molecule is said to be encoded by a particular nucleotide sequence it is to be understood that this is referring to the transcriptional relationship between the DNA and RNA species in question. As such "encoding nucleotide" refers to herein as the nucleotide which can give rise through transcription, and in the case of proteins, translation a functional RNA or protein.

As used herein, "fast maturing" refers to a signal molecule (e.g. a fluorescent protein) that can be measured, preferably within the linear range of the signal molecule, within about 0 to about 4 hours of initial contact of the signal molecule, a sensor system containing the signal molecule (such as those described herein), or sensor organism containing the signal molecule (such as those described herein), with a sample, substrate of the signaling molecule, aforementioned system or organism.

Discussion

Production of chemicals by microbial bioreactors can provide a sustainable, cost-effective, and environmentally friendly alternative to the synthesis of fuels and other chemicals from petroleum and other natural products. Identification of most microbially-produced chemicals, including biofuels, currently relies on low-throughput ($10^2$ samples per day) chromatography-based screens due to the lack of a chemical handle that can be exploited for rapid colorimetric detection. Colorimetric microbially-produced chemicals, such as lycopene and indigo, are amenable to high-throughput ($10^7$ samples per day) screening and have been successfully linked to genome engineering strategies for improved microbial production. However, the number chemicals for which a colorimetric assay exists are extremely limited and far eclipsed by the number of chemicals for which no such assay exists. Further, many of the colorimetric assays have limited sensitivity and can only detect a type of chemical (e.g. fatty acid) as opposed to a specific chemical (e.g. decanoic acid).

To make non-colorimetric chemicals similarly amenable to high-throughput screening and specific for a particular chemical, improved chemical sensors are needed. Given the number of microbially-produced chemicals of interest, these sensors should be capable of rapid assembly from existing biological parts. Most chemical biosensors, often encoded by RNA or protein, are composed of a single biological part with two distinct functional units physically and directly linked to one another. These biosensors typically have a sensing unit to detect the chemical and an actuator unit to trigger a cellular process, such as protein fluorescence. An example of this type of biosensor is a fluorescent protein engineered to bind a chemical and binding of the chemical causes a conformational change in the fluorescent protein, which results in a change in the fluorescence produced by the fluorescent protein.

While single-part RNA- and transcription factor-based sensors have been applied to improve the microbial production of chemicals, none rely on allosteric regulation to generate a response to a chemical or the absence thereof. Efficiently transmitting chemical sensing information from the sensing unit to the actuator unit in single-part sensors is challenging, as the conformational change between these units must be extensively fine-tuned to effectively and efficiently transition between the on- and off states. This fine-tuning often requires a combination of in vitro and in vivo screening to engineer a single-part sensor for each chemical of interest.

With that said, described herein are chemical biosensors that can use two different biological parts: one part that is specialized in chemical sensing and another part this is specialized in actuating the signal, where information is transmitted from the sensing unit to the actuating unit not via a physical linkage, but via a physically independent processing unit. In short, the chemical biosensors described herein can be rapidly changed in a modular fashion to quickly generate a desired chemical biosensor. The multi-part chemical biosensors described herein can overcome the need for extensive fine-tuning of each chemical sensor and allow for the rapid development of chemical biosensors that can be used to screen for chemicals in high-throughput systems.

Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

GPCR-Based Chemical Biosensors

Described herein are GPCR-based chemical biosensors that can contain physically distinct components that are operatively coupled to each other and can detect a chemical and generate a signal indicating the presence or absence of a chemical. With the general description in mind, attention is directed to FIG. 1 which shows one embodiment of a GPCR-based chemical sensor described herein. The GPCR-based chemical sensors 1000 described herein can contain a sensing unit 1100, a processing unit 1200, and a response unit 1300, where the sensing unit 1100 can be biologically coupled to and/or in biologic communication with the processing unit 1200 and the processing unit can be biologically coupled to and/or in biologic communication with the response unit 1300.

The sensing unit 1100 can contain a GPCR that can bind to or otherwise interact with a chemical 1400. The sensing unit 1100 can biologically interact with processing unit 1200, which in turn can biologically interact with the response unit 1300. The biologic interaction between the different units of the GPCR-based chemical biosensors 1000 can be direct (i.e. no intermediate molecules, processes, and/or pathways involved in the biological interaction between one or more components of the interacting units) or indirect (i.e. involve one or more intermediate molecules, processes, and/or pathways in the biological interaction between one or more components of the interacting units, where the additional molecules, process and/or pathways are not part of the sensing unit, processing unit, or response unit).

In operation, a chemical 1400 can bind, unbind, or otherwise interact with the GPCR of the sensing unit 1100. Upon chemical interaction with the GPCR of the sensing unit 1100, the GPCR can biologically interact with the processing unit 1200. In some embodiments, chemical binding (or other interaction) with the GPCR of the sensing unit 1100 can stimulate, either directly or indirectly, a signal transduction pathway that is part of the processing unit 1200. The signal transduction pathway of the processing unit 1200 can then biologically interact with the response unit 1300, which can then generate or extinguish a signal. In some embodiments, the biological interaction between the processing unit 1200 and the response unit 1300 can be direct or indirect regulation of a signaling molecule gene promoter. In this way the processing unit 1200 can transmit a biological signal indicating the interaction of a chemical with the sensing unit 1100 to the response unit 1300, which can signal the presence (or absence) of a chemical 1400.

Figure 2A:
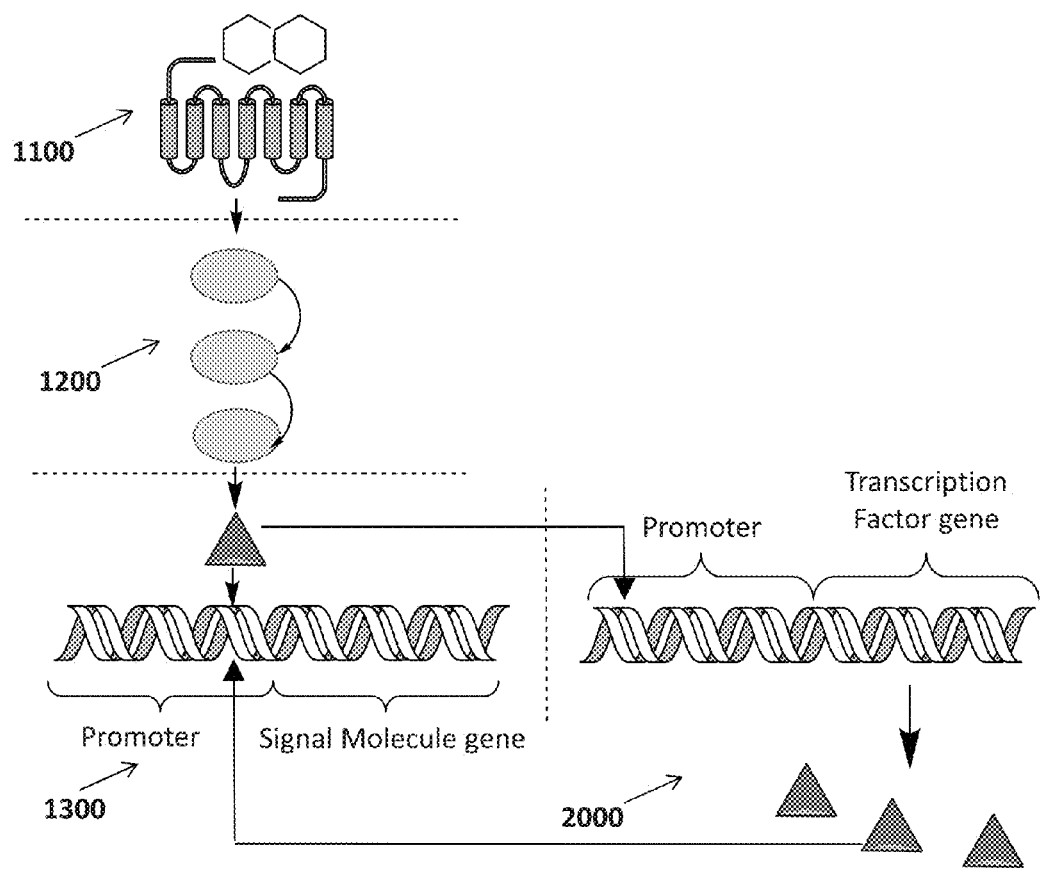
FIGS. 2A and 2B show embodiments of a GPCR-based chemical biosensor having an optional amplification unit that can directly (FIG. 2A) or indirectly (FIG. 2B) amplify a signal generated by a sensing unit of the GPCR-based chemical sensor.
Figure 2B:
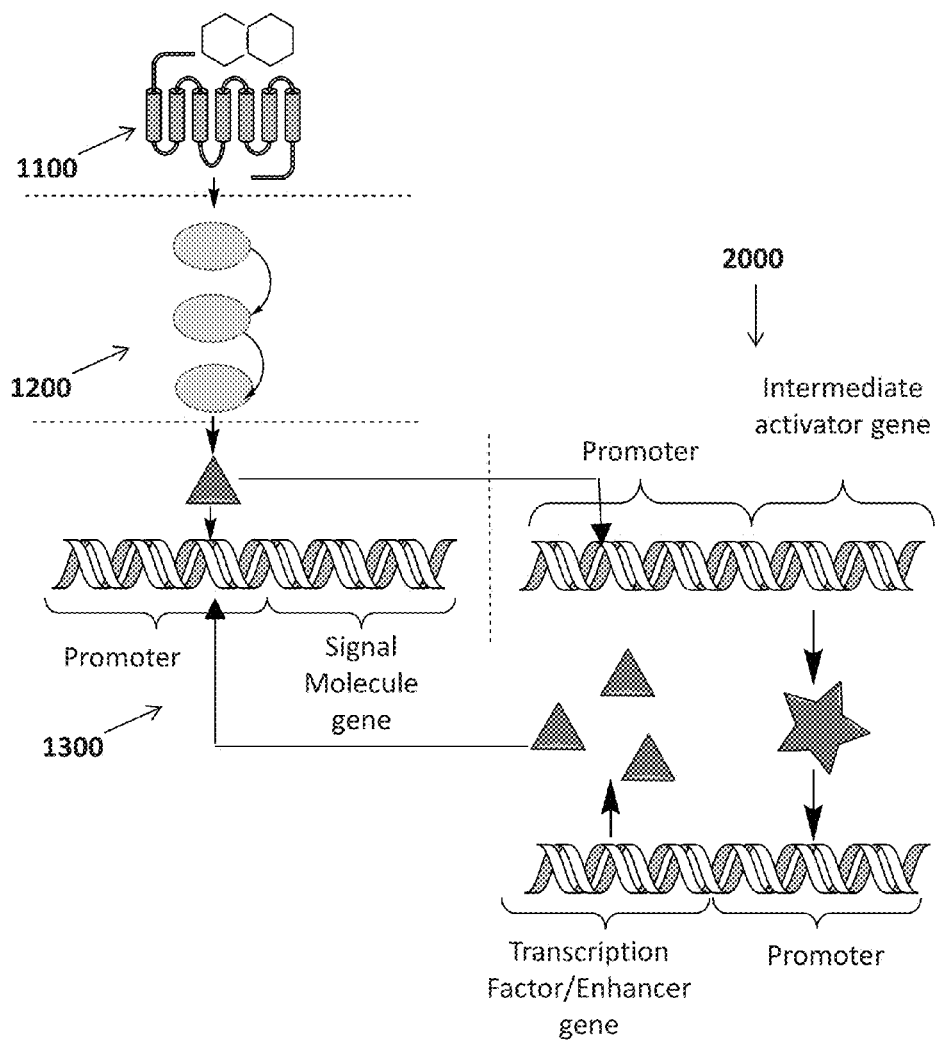

As shown in FIGS. 2A and 2B, the GPCR-based chemical biosensor 1000 can optionally contain an amplification unit 2000. The amplification unit 2000 can be configured to directly (FIG. 2A) or indirectly (FIG. 2B) amplify the signal generated by the response unit 1300. Generally, the amplification unit 2000 can act as a feed forward loop that stimulates increased signal production from the response unit 1300 when the response unit is biologically acted upon, either directly or indirectly, by the processing unit 1200. In short, the amplification unit can autoamplify the signal from the response unit 1300 in response to a chemical 1400 binding, unbinding, or otherwise interacting with the GPCR of the sensing unit 1100. The mechanism by which amplification can occur is described in greater detail elsewhere herein.

The physically distinct components can be expressed within a whole cell, such as a yeast cell. In other embodiments, the physically distinct components can be expressed in a synthetic in vitro system. The physically distinct components can be considered modular components where each one can be independently manipulated and changed without alteration of the other components. This modular configuration can allow for efficient and rapid tuning and customization of system based on the desired sensing and signaling capabilities of the GPCR-based chemical biosensor. The individual modular components are discussed in further detail below.

Sensing Unit

As shown in FIG. 1, the sensing unit 1100 can contain a GPCR. The GPCR can be a native GPCR. In some embodiments, the GPCR can be a non-naturally occurring GPCR, which includes but is not limited to, recombinant and other engineered GPCRs. In some embodiments, the GPCR can be a heterologous GPCR, a homologous GPCR, an orthologous GPCR, or a paralogous GPCR. The GPCR can be a GPCR in the family of Rhodopsin-like GPCRs, secretin receptor GPCRs, metabotropic glutamate/pheromone GPCRs, fungal mating pheromone GPCRs, cyclic AMP GPRCs, or Frizzled, Smoothened GPCRs. In some embodiments, the GPCR is codon optimized for the organism in which the GPCR-based biosensor is to be expressed in. In some embodiments, the GPCR can be GPCR40 (also referred to herein as GPR40). In other embodiments, the GPCR can be OR1G1 or any other olfactory receptor GPCR. In other embodiments, the GPCR can be M3 muscarinic receptor, D2S Dopamine receptor, Beta2 Adrenergic receptor, Beta Alanine receptor, Nicotinamide receptor, OR56, Geosmin GPCR, melatonin receptor (mel1a), or AT1R. In further embodiments, the GPCR can be STE2 GPCR or STE3 GPCR. In some embodiments, the GPCR can have an encoding nucleotide sequence according to any of SEQ ID NOs: 59-75.

The sensing unit 1100 and/or the GPCR of the sensing unit 1100 can be configured to biologically interact with the processing unit 1200. The GPCR can be configured to interact with one or more signal transduction pathways within the host cell (i.e. the cell in which the GPCR is expressed in). GPCRs contain three subunits (typically denoted Gα, Gβ/Gλ) that interact with each other either by the subunits associating with one another upon binding/unbinding a substrate (e.g. chemical) or one or more subunits disassociating from the other subunit(s) upon binding/unbinding a substrate. The disassociation or association of one or more subunits of the GPCR can stimulate or inactivate a downstream signal transduction pathway present in a host cell or in vitro environment. In some embodiments, the signal transduction pathway can be part of the processing unit of the GPCR-based chemical biosensor. In other embodiments, this signal transduction pathway is an intermediate between the sensing unit 1100 and the processing unit 1200. It will be appreciated by those of ordinary skill in the art that the signal transduction pathway will vary based on the GPCR employed in the sensing unit 1100 and the host cell. The signal transduction pathway can be a MAPK pathway, adenylyl cyclase pathway, phospholipase C pathway, arachidonic acid pathway, cyclic AMP (cAMP) pathway, RhoGEF signaling pathways, ion channels (e.g. G-protein-regulated rectifying K+ channels, P/Q- and N-type voltage gated channels, and posphoinositide-3-kinase pathways). In some embodiments, the GPCR can directly signal the processing unit through signaling β-arrestin, G protein-coupled receptor kinases, and tyrosine kinases (e.g. proto-oncogene tyrosine-protein kinase Src).

The GPRC of the sensing unit 1100 can be configured to bind any desired chemical. The GPCR can naturally bind a chemical of interest or can be modified to have improved or otherwise altered binding characteristics (e.g. bind a substrate that would not naturally bind to the GPCR). In some embodiments, the GPCR can bind a medium chain (i.e. a C8-C14) fatty acid. In some embodiments, the chemical can be C10 fatty acid.

Processing Unit

The GPCR-based chemical biosensor 1000 described herein can contain a processing unit 1200. The processing unit 1200 can include one or more endogenous, synthetic, or otherwise modified signal transduction pathways. In synthetic or otherwise modified signal transduction pathways, at least one molecule involved in the signal transduction pathway can be recombinant, or otherwise non-natural. The signal transduction pathway can be a MAPK pathway, adenylyl cyclase pathway, phospholipase C mediated pathway (e.g. inositol 1,4,5-triposphate ($IP_3$)/Diacyl glycerol (DAG) pathway), arachidonic acid pathway, cyclic AMP (cAMP) pathway, RhoGEF signaling pathways, ion channels (e.g. G-protein-regulated rectifying K+ channels, P/Q- and N-type voltage gated channels, posphoinositide-3-kinase pathways, 6-arrestin, G protein-coupled receptor kinases, histidine-specific protein kinase mediated pathways, tyrosine kinase mediate pathways, AKT pathways FAK mediated pathways, GSK3β pathways. In some embodiments, the processing unit 1200 can contain molecules within the mating pathway of yeast. In other words, the GPCR of the sensing unit 1100 can be configured to stimulate molecules in the mating pathway of yeast (e.g. Ste4, GPA1, Ste20, Ste5, Ste11, Ste7, and/or Fus3).

The signal transduction pathway of the processing unit 1200 can regulate one or more transcription factors. Regulation of transcription factors can include, but is not limited to, activation or suppression of transcription factors. One of ordinary skill in the art will appreciate the myriad of ways activation or suppression of a transcription factor(s) can occur and all are within the spirit and scope of this description. The transcription factor can be native to the host cell. In other embodiments, the transcription factor is a synthetic transcription factor that is not native to the host cell or the signaling pathway employed by the processing unit 1200. In some embodiments, the transcription factor is Ste12. In other embodiments, the transcription factor is a synthetic transcription factor including, but not limited to, STF1 (a transcription factor composed of the STE12 phosphorylation domain and the Gal4 activation and DNA binding domains (Pi, H. W., Chien, C. T., and Fields, S. (1997)). Transcriptional activation upon pheromone stimulation can be mediated by a small domain of *Saccharomyces cerevisiae* Ste12p, *Mol Cell Biol* 17, 6410-6418.)), STF2 (a transcription factor composed of the STE12 phosphorylation domain, the synthetic B42 activation domain and the bacterial LexA DNA binding domain (Golemis, E. A., and Brent, R. (1992) Fused Protein Domains Inhibit DNA-Binding by Lexa, *Mol Cell Biol* 12, 3006-3014 and Peralta-Yahya, P., Carter, B. T., Lin, H. N., Tao, H. Y., and Comish, V. W. (2008) High-Throughput Selection for Cellulase Catalysts Using Chemical Complementation, *J Am Chem Soc* 130, 17446-17452)), STF3 (a transcription factor composed of the CRE protein activation and phosphorylation domain with the Gal4 DNA binding domain), STF4 (a transcription factor composed of the CRE protein activation and phosphorylation domain and the LexA DNA binding domain). The synthetic transcription factor can be configured to interact with an endogenous or a synthetic promoter.

Response Unit

The GPCR-based chemical biosensor 1000 can contain a response unit 1300. The response unit can contain a signal molecule promoter operatively coupled to a signal molecule gene, where the signal molecule gene encodes or otherwise (e.g. by activating other pathways in the cell that results in the production of a gene product, such as a protein that can be measured) generates a signal molecule. The promoter can be configured to stimulate or extinguish transcription of the signal molecule gene (and subsequent production of the signal molecule) upon binding or unbinding of a transcription factor (such as one stimulated by the processing unit 1200). In this way, a signal (either appearance or disappearance of the signal molecule) can be generated by the GPCR-based chemical biosensor 1000 in response to binding, unbinding, or other interaction of a chemical 1400 with the GPCR of the sensing unit 1100.

The transcription factor can be native to the host cell or synthetic. In other embodiments, the transcription factor is a synthetic transcription factor that is not native to the host cell or the signaling pathway employed by the processing unit 1200. In some embodiments, the transcription factor is Ste12. In other embodiments, the transcription factor is a synthetic transcription factor including, but not limited to, STF1 (a transcription factor composed of the STE12 phosphorylation domain and the Gal4 activation and DNA binding domains) (Pi, H. W., Chien, C. T., and Fields, S. (1997)). Transcriptional activation upon pheromone stimulation can be mediated by a small domain of *Saccharomyces cerevisiae* Ste12p, *Mol Cell Biol* 17, 6410-6418.)), STF2 (a transcription factor composed of the STE12 phosphorylation domain, the synthetic B42 activation domain and the bacterial LexA DNA binding domain) (Golemis, E. A., and Brent, R. (1992) Fused Protein Domains Inhibit DNA-Binding by Lexa, *Mol Cell Biol* 12, 3006-3014 and Peralta-Yahya, P., Carter, B. T., Lin, H. N., Tao, H. Y., and Comish, V. W. (2008) High-Throughput Selection for Cellulase Catalysts Using Chemical Complementation, *J Am Chem Soc* 130, 17446-17452)), STF3 (a transcription factor composed of the CRE protein activation and phosphorylation domain with the Gal4 DNA binding domain), STF4 (a transcription factor composed of the CRE protein activation and phosphorylation domain and the LexA DNA binding domain). The transcription factor can be directly stimulated by the processing unit or can be the product of another signal transduction pathway stimulated by the processing unit (via a transcription factor or other mode of pathway stimulation).

In some embodiments the transcription factor can have a sequence about 90% to 100% identical to SEQ ID NOS: 51-53.

```
(STF1 sequence)
                                                    SEQ ID NO: 51
ATGAAGCTACTGTCTTCTATCGAACAAGCATGCGATATTTGCCGACTTAAAAAGCTCAAGTG

CTCCAAAGAAAAACCGAAGTGCGCCAAGTGTCTGAAGAACAACTGGGAGTGTCGCTACTC

TCCCAAAACCAAAAGGTCTCCGCTGACTAGGGCACATCTGACAGAAGTGGAATCAAGGCT

AGAAAGACTGGAACAGCTATTTCTACTGATTTTTCCTCGCGAAGACCTTGACATGATTTTGA

AAATGGATTCTTTACAGGATATAAAAGCATTGTTAACAGGATTATTTGTACAAGATAATGTGA

ATAAAGATGCCGTCACAGATAGATTGGCTTCAGTGGAGACTGATATGCCTCTAACATTGAG

ACAGCATAGAATAAGTGCGACATCATCATCGGAAGAGAGTAGTAACAAAGGTCAAAGACAG

TTGACTGTATCTAGACCATCTAGTACAACAAAATCAGATAATTCGCCTCCAAAATTAGAAAG

CGAGAATTTTAAGGATAATGAGTTGGTAACAGTAACTAATCAGCCGCTTTTAGGCGTTGGC

CTCATGGATGACGATGCGCCAGAATCCCCCTCTCAAATTAATGATTTTATTCCTCAGAAATT

GATTATAGAACCCAATACTCTCGAATTGAATGGTCTCACAGAAGAAACGCCTCATGACTTAC

CCAAGAATACCGCTAAGGGCAGAGACGAAGAAGATTTTCCTCTCGACTATTTTCCTGTATC

TGTTGAATACCCTACGGAGGAAAATGCGTTTGATCCGTTCCCTCCACAGGCTTTTACGCCA

GCTGCCCCTTCCATGCCTATTTCCTATGATAACGTGAATGAAAGGGATTCTATGCCCGTTAA

TTCTCTTCTTAATAGATACCCCTATCAGTTATCAGTGGCACCCACTTTCCCAGTGCCACCAT

CATCATCGAGGCAACATTTTATGTATCCTTACGACGTTCCAGATTATGCTATTGACTCTGCA

GCTCATCATGATAACTCCACAATTCCGTTGGATTTTATGCCCAGGGATGCTCTTCATGGATT

TGATTGGTCTGAAGAGGATGACATGTCGGATGGCTTGCCCTTCCTGAAAACGGACCCCAA

CAATAATGGGTTCTAA (STF2 sequence)
                                                    SEQ ID NO: 52
ATGGGTGCTCCACCTAAGAAGAAAAGAAAGGTTGCCAAAGCTTTGACTGCCAGACAACAAG

AAGTCTTCGATTTGATTAGAGATCATATTTCTCAAACTGGTATGCCACCAACTAGAGCTGAA

ATTGCTCAAAGATTGGGTTTCAGATCTCCAAACGCCGCTGAAGAACACTTGAAAGCTTTGG

CTAGAAAGGGTGTCATTGAAATTGTTTCTGGTGCTTCTAGAGGTATTAGATTGTTGCAAGAA
```

-continued

```
GAAGAAGAAGGTTTGCCATTGGTTGGTAGAGTCGGTAGACCATCTTCTACTACTAAATCTG

ATAACTCTCCACCAAAGTTGGAATCTGAAAACTTCAAAGATAACGAATTGGTTACTGTTACA

AATCAACCATTGTTAGGTGTCGGTTTGATGGATGACGATGCTCCAGAATCTCCTTCTCAAAT

TAACGATTTCATTCCACAAAAGTTGATTATTGAACCAAACACTTTGGAATTGAACGGTTTGA

CTGAAGAAACTCCACACGATTTGCCAAAGAATACTGCCAAAGGTAGAGATGAGGAAGACTT

CCCATTGGATTACTTTCCAGTTTCTGTCGAATATCCAACTGAAGAAAACGCTTTCGATCCAT

TTCCACCACAAGCCTTTACTCCAGCTGCACCATCTATGCCAATTTCTTACGATAACGTTAAT

GAAAGAGATTCTATGCCAGTCAACTCATTGTTGAATAGATACCCATATCAATTGTCTGTTGC

TCCAACTTTCCCAGTTCCTCCATCTTCTTCAAGACAACACTTTATGGGTATTAACAAGGATA

TTGAGGAATGTAATGCCATCATTGAACAATTCATCGATTACTTGAGAACTGGTCAAGAAATG

CCAATGGAAATGGCCGATCAAGCCATTAACGTTGTCCCAGGTATGACTCCAAAGACTATTT

TGCACGCTGGTCCACCAATTCAACCAGATTGGTTGAAATCTAACGGTTTCCACGAAATTGA

AGCTGATGTCAATGACACATCTTTGTTATTGTCTGGTGATGCCTCTTAA
```

(STF3 sequence)

SEQ ID NO: 53

```
ATGACTATGGATTCTGGTGCTGATAATCAACAATCTTCTTGTAAAGATTTGAAAAGATTGTTT

TCTGGTACTCAAATTTCTACTATTGCTGAATCTGAAGATTCTCAAGAATCTGTTGATTCTGTT

ACTGATTCTCAAAAAAGAAGAGAAATTTTGTCTAGAAGACCATCTTATAGAAAAATTTTGAAT

GATTTGTCTTCTATTGAACAAGCTTGTGATATTTGTAGATTGAAAAAATTGAAATGTTCTAAA

GAAAAACCAAAATGTGCTAAATGTTTGAAAATAATTGGGAATGTAGATATTCTCCAAAAAC

TAAAAGATCTCCATTGACTAGAGCTCATTTGACTGAAGTTGAATCTAGATTGGAAAGATTGG

AACAATTGTTTTGTTGATTTTTCCAAGAGAAGATTTGGATATGATTTTGAAAATGGATTCTT

TGCAAGATATTAAAGCTTTGTTGACTGGTTTGTTTGTTCAAGATAATGTTAATAAAGATGCTG

TTACTGATAGATTGGCTTCTGTTGAAACTGATATGCCATTGACTTTGAGACAACATAGAATT

TCTGCTACTTCTTCTTCTGAAGAATCTTCTAATAAAGGTCAAAGACAATTGACTGTTTCTATT

GATTCTGCTGCTCATCATGATAATTCTACTATTCCATTGGATTTTATGCCAAGAGATGCTTTG

CATGGTTTTGATTGGTAA
```

The signal molecule promoter can be a native promoter in the host cell. Suitable native promoters include without limitation those involved in the yeast mating pathway (e.g. FIG. 1 and Fus 1, Fig 3, Fig2, Fig4). The signal molecule promoter can be a synthetic promoter. Suitable synthetic promoters include without limitation PGal4(5x), which is described in greater detail elsewhere herein, and contains five Gal4 binding sites and PLexA(4x), which is described in greater detail elsewhere herein, and contains 4 LexA binding sites. In some embodiments, the synthetic promoter can have a nucleotide sequence about 90% to 100% identical to any one of SEQ ID Nos: 54-56

PGal4(5x): (The underlined ATG is the start codon)

SEQ ID: NO: 54

```
CCGAGCTCTTACGCGGGTCGAAGCGGAGTACTGTCCTCCGAGTGGAGTACTGTCCTCCGA

GCGGAGTACTGTCCTCCGAGTCGAGGGTCGAAGCGGAGTACTGTCCTCCGAGTGGAGTA

CTGTCCTCCGAGCGGAGTACTGTCCTCCGAGTCGACTCTAGAGGGTATATAATG
```

PLexA(4x): (The underlined ATG is the start codon)

SEQ ID: NO: 55

```
CCGAGCTCTTACGCGGGTCGAAGTGCTGTATATACTCACAGCAAGTGGAGTACTGTCCTC

CGAGAACTGTATATACACCCAGGGAGTCGAGGGTCGAAGTACTGTATGAGCATACAGTAA
```

-continued

```
GTGGAGTACTGTCCTCCGAGAACTGTATATAAATACAGTTAGTCGACTCTAGAGGGTATAT

AATG
```

(PCRE)

SEQ ID NO: 56
```
TCCTGGAAGTCTCATGGAGATTATACTTTATGCACCAGACAGTGACGTCAGCTGCCAGATC

CCATGGCCGTCATACTGTGACGTCTTTCAGACACCCCATTGACGTCAATGGGAGAACTTTA

GTATCCGTTTAGCTAGTTAGTACCTTTGCACGGAAATGTATTAATTAGGAGTATATTGAGAA

ATAGCCGCCGACAAAAAGGAAGTCTCATAAAAGTGTCTAACAGACAATTAGCGCAATAAGA

AGAAAGAAAACGGATTGAAGTTGAGTCGAGAATAATATGGCACCCAGAAAACGCTTTAGGC

TACTCGAATTAGGGTCACCAATG
```

In some embodiments, the promoter can be or include a repressor element. In some embodiments the repressor can consist of or include a sequence about 90% to about 100% identical to SEQ ID NO: 57 and/or SEQ ID NO: 58.

(pGal4(5x) repressor)

SEQ ID NO: 57
```
TCGACTCTAGAGGGTATATACCGAGCTCTTACGCGGGTCGAAGCGGAGTACTGTCCTCCG

AGTGGAGTACTGTCCTCCGAGCGGAGTACTGTCCTCCGAGTCGAGGGTCGAAGCGGAGT

ACTGTCCTCCGAGTGGAGTACTGTCCTCCGAGCGGAGTACTGTCCTCCGAGGGATCCATG
```

(pLexA(4x) repressor)

SEQ ID NO: 58
```
CCGAGCTCTTACGCGGGTCGAAGTGCTGTATATACTCACAGCAAGTGGAGTACTGTCCTC

CGAGAACTGTATATACACCCAGGGAGTCGAGGGTCGAAGTACTGTATGAGCATACAGTAA

GTGGAGTACTGTCCTCCGAGAACTGTATATAAATACAGTTAGTCGACTCTAGAGGGTATAT

AATGATG
```

The signal molecule promoter can be operatively coupled to a signal molecule gene, which can encode a suitable signal molecule. Suitable signal molecules include without limitation, a fluorescent protein, β-galactosidase protein, a luciferase protein, and chloramphenicol acetyltransferase, antibiotic resistance markers such as KanMX4, auxotrophic genes such as His3, Ura3, TRp1, Leu2 which enable selections and counter selections, a biosynthetic gene or pathway that results in the production of a colorimetric or fluorescent compound, such as lycopene, indigo or violacein, a synthetic RNA, a synthetic DNA or a ribozyme Suitable fluorescent proteins include without limitations, green fluorescent proteins and enhanced green fluorescent proteins, yellow fluorescent proteins and enhanced yellow fluorescent proteins, blue fluorescent proteins and enhanced blue fluorescent proteins, cyan fluorescent proteins and enhanced cyan fluorescent proteins, orange fluorescent proteins and enhanced orange fluorescent proteins, and red fluorescent proteins and enhanced red fluorescent proteins. Fluorescent proteins are generally known in the art and are commercially available. All of these are within the scope and spirit of the present disclosure. The signal molecule gene can be codon optimized for expression within the particular host cell. In some embodiments, the signal molecule is a fast maturing signal molecule.

Amplification Unit

As shown in FIGS. 2A and 2B, the GPCR-based chemical biosensor 1000 can optionally contain an amplification unit 2000. The amplification unit 2000 can be configured to directly (FIG. 2A) or indirectly (FIG. 2B) amplify the signal generated by the response unit 1300. Generally, the amplification unit 2000 can act as a feed forward loop that stimulates increased signal production from the response unit 1300 when the response unit is biologically acted upon, either directly or indirectly, by the processing unit 1200. In short, the amplification unit can autoamplify the signal from the response unit 1300 in response to a chemical 1400 binding, unbinding, or otherwise interacting with the GPCR of the sensing unit 1100.

As shown in FIG. 2A the amplification unit 2000 can be configured to directly amplify the signal generated by the response unit 1300. The amplification unit can contain an amplification unit promoter that can be operatively coupled to a transcription factor gene. The product(s) of the transcription factor gene can be a suitable transcription factor. In operation, the transcription factor stimulated by the processing unit 1200 can bind the signal molecule gene promoter of the sensing unit 1300 and the promoter of the amplification unit 2000. The promoter of the amplification unit 2000 can drive gene expression of a transcription factor that can bind also bind or otherwise interact with the signal molecule promoter of the response unit 1300 to drive gene expression of the signal molecule and generate additional signal molecules in a feed forward fashion. Insofar as additional signal molecules can be generated without additional input stimulation from the sensing unit 1100, the signal from the GPCR-based chemical biosensor can be amplified.

Suitable transcription factors produced by the amplification unit 2000 can be any transcription factor configured to bind or otherwise active the signal molecule gene promoter of the response unit 1300 and generate an upregulation in gene expression of the signal molecule gene. In some embodiments, the transcription factor produced by the amplification unit 2000 can be the same transcription factor produced or stimulated by the processing unit 1200. In some embodiments, the transcription factor produced by the amplification unit 2000 can be Ste12, STF1, or STF2.

Suitable promoters for the amplification unit 2000 can include native and synthetic promoters. The amplification unit promoter can be a native promoter in the host cell. Suitable native promoters include without limitation those involved in the yeast mating pathway (e.g. FIG. 1 and Fus 1, Fig3, Fig4, Fig2). The amplification unit promoter can be a synthetic promoter.

Suitable synthetic promoters include without limitation PGal4(5×), which is described in greater detail elsewhere herein, and contains five Gal4 binding sites and PLexA(4×), which is described in greater detail elsewhere herein, and contains 4 LexA binding sites. In some embodiments, the synthetic promoter can have a nucleotide sequence identical to any one of SEQ ID Nos: 54-56.

As shown in FIG. 2B, the optional amplification unit 2000 can indirectly amplify the signal generated by the GPCR-based chemical biosensor. In these embodiments, the amplification unit 2000 can contain a first amplification unit promoter operatively coupled to an intermediate activator gene. The intermediate activator gene can encode for a suitable intermediate molecule that is capable of binding a second amplification unit promoter that is operatively coupled to a transcription factor gene. Any promoter described herein or any other native promoter can be used as a promoter in the amplification unit. The promoter can be operatively coupled to the transcription factor gene. The second amplification unit promoter and the transcription factor gene can be as described with respect to the amplification unit promoter and transcription factor gene and gene product(s). Any promoter described herein or any other native promoter can be used as a promoter in the amplification unit. The promoter can be operatively coupled to the transcription factor gene or intermediate activator gene.

In operation, the transcription factor produced by the processing unit 1200 can bind or otherwise activate both the signal molecule promoter of the response unit 1300 and the first amplification unit promoter. When the first amplification unit promoter is activated, it can drive expression of the intermediate activator gene and thus production of a suitable intermediate activator molecule (e.g. another transcription factor or other protein involved in up-regulation of genes, particularly those that are part of the amplification unit). The intermediate activator molecule can then bind or otherwise activate the second amplification unit promoter and thus stimulate production of a transcription factor that can bind or otherwise interact with the signal molecule promoter of the response unit 1300 to drive gene expression of the signal molecule and generate additional signal molecules in a feed forward fashion. Insofar as additional signal molecules can be generated without additional input stimulation from the sensing unit 1100, the signal from the GPCR-based chemical biosensor can be amplified.

Host Cells

The sensing unit, processing unit, and/or the response unit can be expressed or otherwise contained within a single host cell. The host cell can be eukaryotic or prokaryotic. In some embodiments, the host cell can be a mammalian cell, a fungal cell, or a bacterial cell. In some embodiments the host cell is a yeast cell. Suitable yeast species for the host cell include but are not limited to *S. cerevisiae, Pichia Pastoris, Saccharomyces Pombe*. Suitable strains of *S. cerevisiae* include, but are not limited to the W303 strain (ATCC), PPY62, PPY58, PPY140, and PPY161. The GPCR-based chemical biosensors can be introduced into the host cell via a single or multiple plasmid system or integrated into the genome. The GPCR-based chemical biosensor or can be stably or transiently expressed within the host cell. In some embodiments, the host cell is different from a producer cell (i.e., a cell that produces a chemical to be detected by the GPCR-based chemical biosensor). The GPCR-based chemical sensors can be used to evolutionary engineer or high-throughput engineering chemical-producing microbes using medium-throughput methods (e.g. 96-well plate), or high-throughput methods (e.g. microfluidic chip).

Systems and Methods of Using the GPCR-Based Chemical Biosensors

Also described herein are systems and methods of using the GPCR-based chemical biosensors. As described above, the modular components of the GPCR-based chemical biosensors can be expressed within a host cell (also referred to herein as a sensor cell or sensor strain). The host cell can then be used in a method to sense a chemical (which includes proteins) of interest. The method can include incubating a host cell containing a GPCR-based chemical biosensor as described herein in a solution or environment containing a sample, a cell, or other composition to be analyzed for a period of time. After the period of time, a suitable assay or other suitable measurement technique can be performed to measure the amount of signal molecule produced by the GPCR-based chemical biosensor. One of skill in the art will appreciate that the particular assays or measurement technique used will depend on the type of signaling molecule produced. Suitable assays and measurement techniques include, but are not limited to, flow cytometry, FACS, luciferase assays (single and dual), β-galactosidase assays, microtiter plate reader, and CAT assays, antibiotic selection, auxotrophic forward and counter selection. Other assays and techniques will be readily appreciated by those of ordinary skill in the art.

Figure 3:
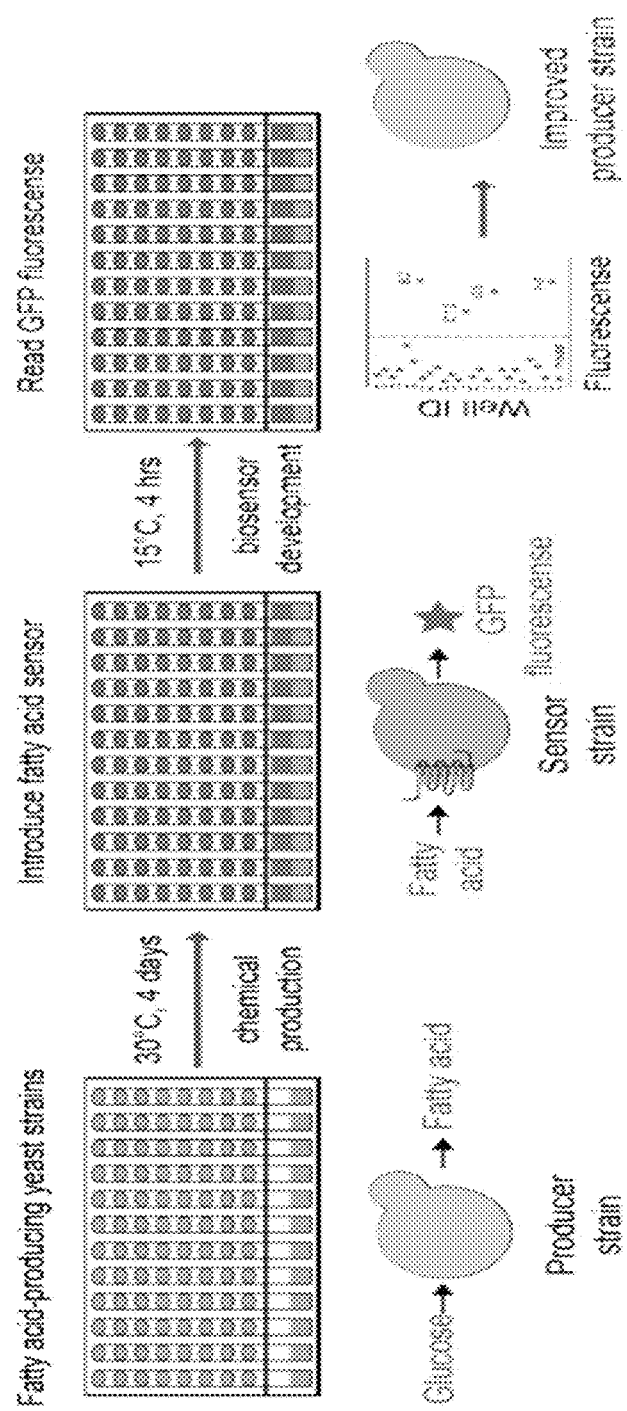
FIG. 3 shows one embodiment of a medium throughput system for screening chemical producing cells using a GPCR-based chemical sensor as described herein.

In some embodiments, the sensor cell or strain can be used to detect a medium chain fatty acid in a sample. In other embodiments, the sensor strain can be used to detect production of a desired chemical (which includes proteins) such as a medium chain fatty acid, from a producer cell. These can be accomplished in a low-throughput or medium through-put fashion. As shown in FIG. 3, producing strains can be analyzed in a medium through put fashion by arraying different producing strains in a multi-well plate, incubating the producing strains for a first period of time to allow for generation of a chemical product from the producing strain(s).

After the first period of time, a sensor cell(s) can be added to the wells as desired and incubated for a second period of time to allow for interaction, such as binding, between the chemical produced by the producer cell in each well and the GPRC of sensor cell present in the same well. The second period of time can be an amount of time sufficient for biosensor production. The second period of time can range from about 0 to about 96 hours, about 96 to about 72 hours, about 72 to about 60 hours, about 60 hours to about 48 hours, about 48 hours to about 36 hours, about 36 hours to about 24 hours, about 24 hours to about 12 hours, about 12 hours to about 6 hours, about 4 hours to about 6 hours, about 2 hours to 4 hours, and about 0 to about 2 hours. In some embodiments, particularly those when a fast maturing signaling molecule is used, the second period of time can range from about 0 hours to about 3 hours. In other embodiments, the second period of time can be about 4 hours. In further embodiments, the second period of time can be about 1 hour.

After the second period of time, a suitable assay or measurement technique can be performed to measure the amount of signal molecule produced from each well. This can allow for determining which producing cells produced the chemical of interest. In embodiments, where the signal measurement assay/technique can allow for quantification of the amount of signal produced, it can be determined which producing cells produced the most chemical. Such techniques that can allow for quantification include flow cytometry, FACS, luciferase assays, 62-galactosidase assays, microtiter plate reader, antibiotic selection, auxotrophic forward and counter selection and CAT assays. Others will be appreciated by those of skill in the art. In this way, one can select which producing strain is desired based on the determination of their ability to produce (or not produce) a particular chemical.

In some embodiments, the sensor cells as described herein can be used in any of the methods previously described to detect a fatty acid. In some embodiments, the fatty acid is a medium chain fatty acid. In some embodiments, the medium chain fatty acid is a C10 fatty acid. In some embodiments, the GPCR-based chemical biosensor or assay using the GPCR-based chemical biosensor can have a linear range of detection of up to about 250 µM. The GPCR-based chemical biosensor can have a linear detection range of about 500 µM or greater. In some embodiments, the linear detection range can be from about 0 to 1M or any range within that. In some embodiments, the GPCR-based chemical biosensor or assay using the GPCR-based chemical biosensor can have a linear range of detection of up to about 500 µM. In some embodiments, the GPCR-based chemical biosensor or assay using the GPCR-based chemical biosensor can have a linear detection range of about 34 µM to about 250 µM. The GPCR-based chemical biosensor or assay using the GPCR-based chemical biosensor can have a linear detection range of about 110 µM to about 500 µM. The dynamic range of the GPCR-based chemical biosensor or assay using the GPCR-based chemical biosensor can range from about 4 to about 68. The dynamic range is the ratio of the highest fluorescence obtained by the sensor in the presence vs. the absence of the chemical. It will be appreciated that the linear and dynamic range can be customized based on the configuration sensor unit, response unit, processing unit, and amplification unit, both individually and collectively as a system.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

GPCR-Based Biosensors to Detect Medium Chain Fatty Acids

To rapidly construct chemical biosensors, GPCRs were exploited as the sensing unit. GPCRs can bind a large variety of chemicals from biogenic amines and carbohydrates to lipids and odors. GPCR-based chemical sensors have been previously engineered in the yeast *Saccharomyces cerevisiae*, as this organism is amenable to heterologous GPCR expression. Although in the 1990s and 2000s GPCRs were commonly coupled to the yeast mating pathway to discover new ligands for known GPCRs, since then GPCR-based chemical sensing in yeast has been limited. Four main obstacles have hindered GPCR-based sensing in yeast: 1) the unsystematic expression of functional heterologous GPCRs on the yeast cell surface; 2) the unreliable coupling of heterologous GPCRs to the yeast mating pathway; 3) the poor functional expression of mammalian GPCRs; particularly olfactory GPCRs, such that only two olfactory receptors (rat ORI7 and human OR17-40) have been functionally expressed in yeast and have been used as the scaffold to express the ligand binding domain of other olfactory receptors (ORL829, ORL451, MOR226-1); and 4) the weak signal strength of the biosensor.

Here, GPCR codon optimization and the use of a wide array of yeast promoters and plasmids were used overcome these obstacles and enable the rapid construction of GPCR-based chemical sensors in yeast. Specifically, using a plug-and-play strategy, sensing (GPCR), processing (signaling pathway), and response units (transcription factor/promoter/reporter gene) can be mixed and matched to predictably generate chemical sensors (see e.g. FIGS. 1, 2, 7, 12, and 18).

In this Example, the rapid construction of GPCR-based yeast sensors to detect saturated medium-chain fatty acids is demonstrated. Fatty acids are the immediate precursors to the advanced biofuels fatty acid methyl esters (FAMEs), which can serve as a "drop in" replacement for D2 diesel. FAMEs derived from medium-chain fatty acids (C8-C12) have better cold properties than traditional canola oil-derived (C16-C22) FAMEs. Microbial production of medium-chain fatty acids is a challenging problem both in *S. cerevisiae* and *Escherichia coli*, with titers reaching less than 100 mg/L, a stark contrast to the titers reached for C16-C18 in *E. coli* (5 g/L) and *S. cerevisiae* (400 mg/L).

A medium-chain fatty acid sensor could be used for the engineering of microbes with improved medium-chain fatty acid production or the detection of medium-chain fatty acids in a sample. In this Example, the signal after activation of the endogenous Ste2/α-factor was measured to determine the upper limit for future GPCR-based chemical sensors that would rely on heterologous GPCR sensing units coupling to the yeast mating pathway. Then, two GPCRs known to bind fatty acids in mammalian cells were each coupled to the yeast mating pathway to form two separate systems. One of the GPCR-based sensors reliably detects C8-C12 fatty acids with a 13- to 17-fold increase in signal after activation. The sensor is specific to medium-chain fatty acids, not being able to detect long-chain fatty acids or medium-chain aldehydes, alcohols or C10 esters.

Figure 4:
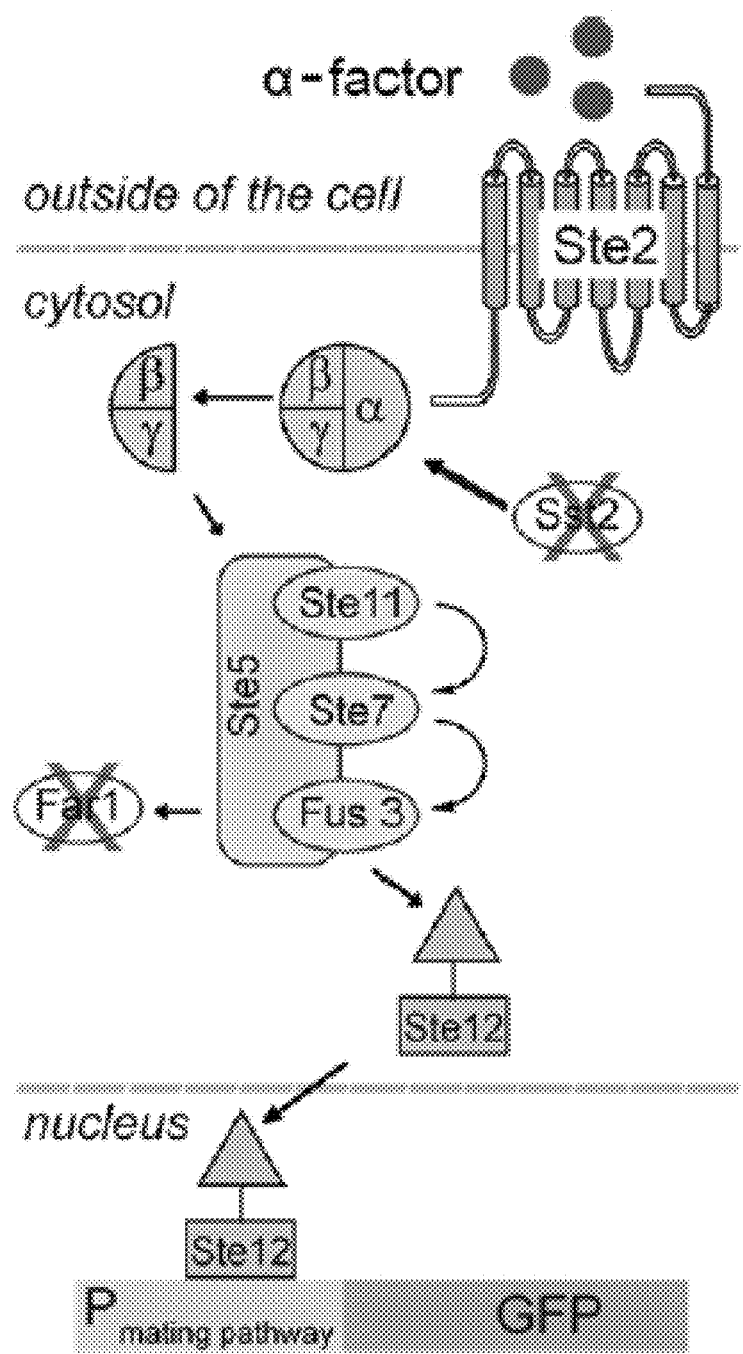
FIG. 4 shows one embodiment of an engineered yeast strain containing deletions of Sst2 and Far1 and one embodiment of a GPCR-based chemical biosensor containing a Ste2/α-factor sensing unit schematic. The Ste2 GPCR can detect α-factor in the culture medium, the chemical signal can be transmitted via the yeast mating pathway to the mating pathway transcription factor Ste12. Ste12 can activate transcription of green fluorescent protein (GFP) under control of a mating pathway promoter (Pmating pathway). The GPCR-based chemical sensor strain has the far1 and sst2 genes deleted to avoid cell cycle arrest and to reduce the spontaneous rate of GPCR inactivation upon chemical sensing, respectively.
Figure 5:
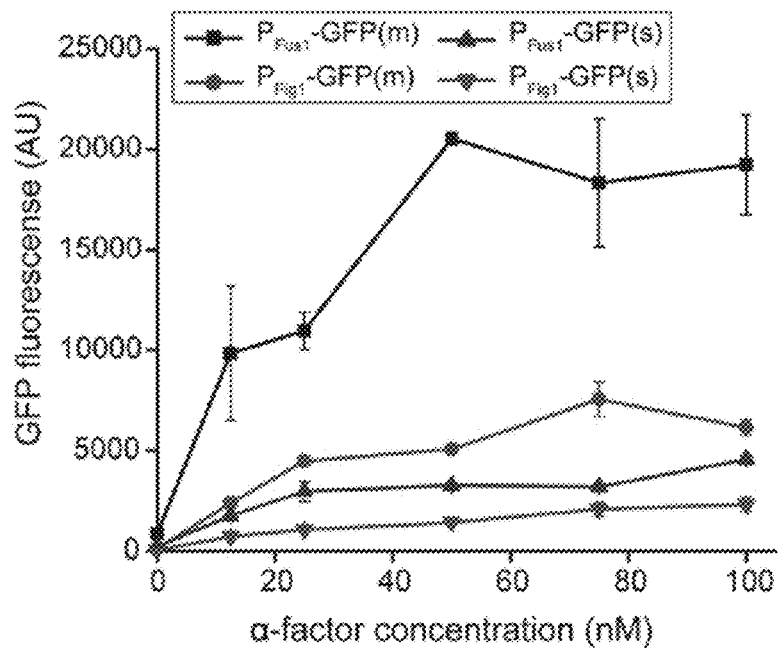
FIG. 5 shows a graph demonstrating Ste2/α-factor sensor dose response curves carrying GFP under control of two mating pathway promoters (PFus1 and PFig1) from either a single-copy (s) or a multicopy (m) reporter plasmids. All experiments were done in triplicate and the error bars represent the standard deviation from the mean.
Figure 6:
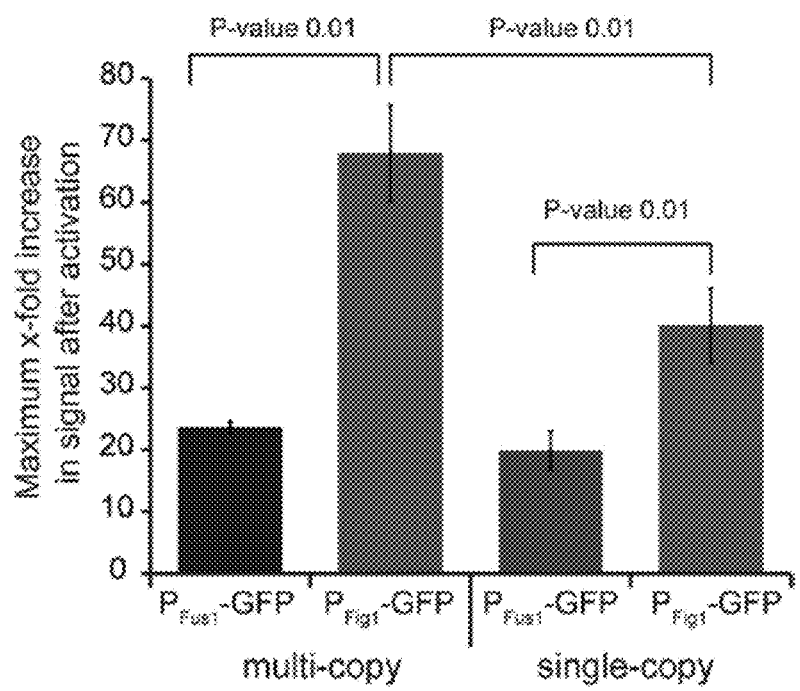
FIG. 6 shows a graph demonstrating maximum x-fold increase in signal after activation: PFus1-GFP(m): 50 nM α-factor, PFig1-GFP(m): 75 nM α-factor, PFus1-GFP(s) and PFig1-GFP(s): 100 nM α-factor. P-values, obtained from a two-tailed t test, shown for statistically different samples. All experiments were done in triplicate and the error bars represent the standard deviation from the mean.

To engineer a GPCR-based chemical sensor strain, two genes in the yeast mating pathway were deleted to avoid cell cycle arrest (far1) and reduce the spontaneous rate of GPCR inactivation upon chemical sensing (sst2). Next, the dynamic range of the endogenous GPCR-based sensor (Ste2/α-factor) was determined using the mating pathway-dependent transcription factor Ste12, which upregulates mating pathway genes (FIG. 4). The response of the Ste2/α-factor sensor using GFP under control of two mating pathway promoters ($P_{FUS1}$ and $P_{FIG1}$) from either a single-copy (s) or a multi-copy (m) reporter plasmids (FIG. 5) was observed. The maximum x-fold increase in signal after activation, defined as the maximal GFP fluorescence in the presence of chemical over the signal in the absence of chemical, for $P_{FUS1}$ and $P_{FIG1}$ from a multi-copy plasmid was observed to be 24- and 68-fold, respectively (P-value 0.009) (FIG. 6). The maximum x-fold increase in signal after activation for $P_{FUS1}$ and $P_{FIG1}$ from a single-copy plasmid was 20- and 40-fold, respectively, (P-value 0.014). The maximum x-fold increase in signal activation from $P_{Fig1}$-GFP (s) and $P_{Fig1}$-GFP (m) was statistically significant (P-value 0.009).

Figure 7:
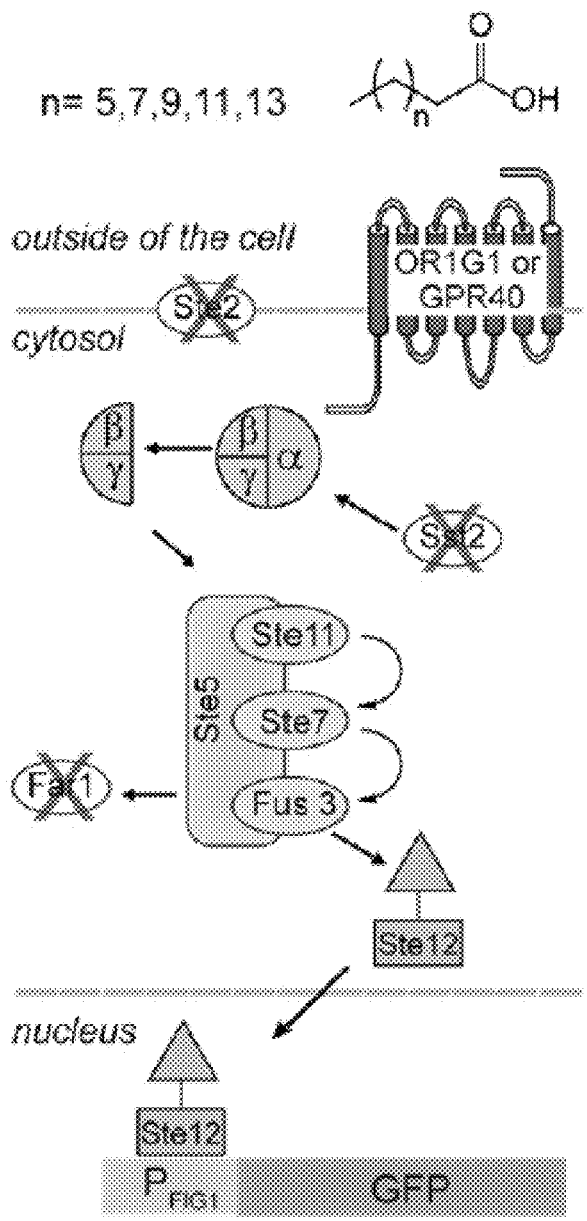
FIG. 7 is a cartoon depicting one embodiment of a GPCR-based chemical biosensor. Either the OR1 G1 or GPR40 GPCR can detect medium-chain fatty acids in the culture medium, the chemical signal is transmitted via the yeast mating pathway to the mating pathway transcription factor Ste12. Ste12 activates transcription of GFP under control of the PFig1 promoter. In addition to deletion of the far1 and sst2 genes, the medium-chain fatty acid sensor strain has the endogenous GPCR Ste2 deleted (W303 Δfar1, Δsst2, Δste2).
Figure 8:
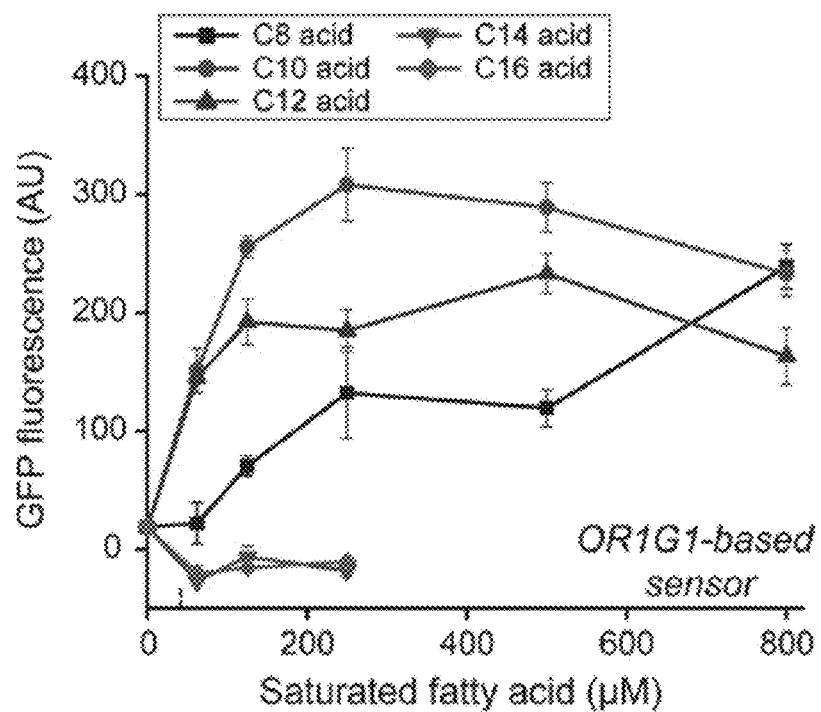
FIG. 8 shows a graph demonstrating dose response curves for the OR1 G1-based sensor (PPY643) with C8, C10, C12, C14 and C16 acids. All experiments were done in triplicate and the error bars represent the standard deviation from the mean.
Figure 9:
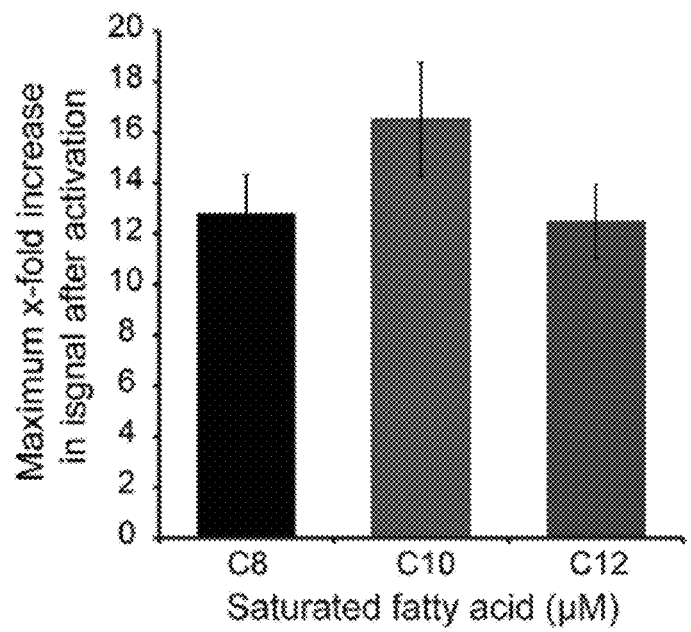
FIG. 9 shows a graph demonstrating OR1G1-based sensor maximum x-fold increase in signal after activation with C8 (800 µM), C10 (250 µM) and C12 (500 µM) acids. All experiments were done in triplicate and the error bars represent the standard deviation from the mean. None of the samples shows a statistical difference using a two-tailed t test.
Figure 10:
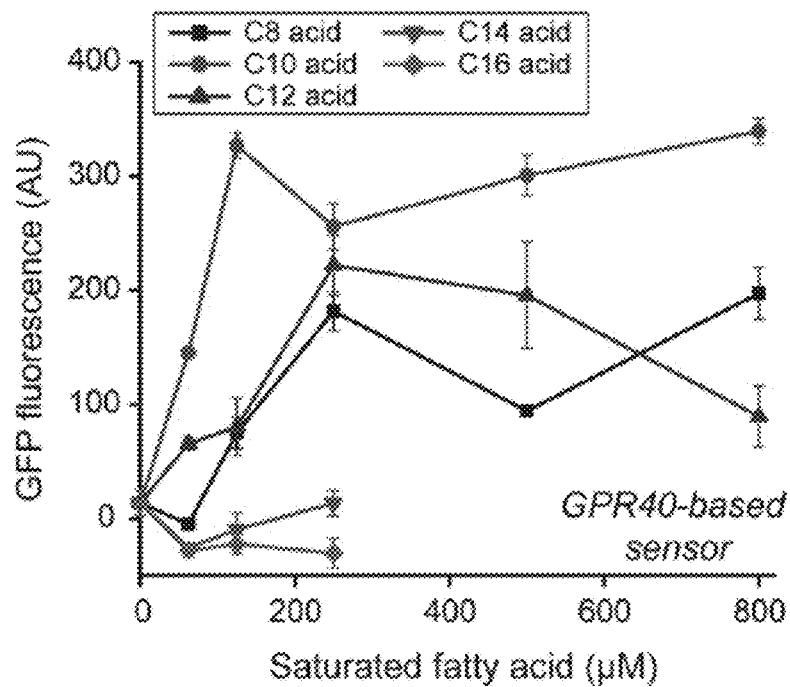
FIG. 10 shows a graph demonstrating dose response curves for the GPR40-based sensor (PPY644) with C8, C10, C12, C14 and C16 acids. All experiments were done in triplicate and the error bars represent the standard deviation from the mean.
Figure 11:
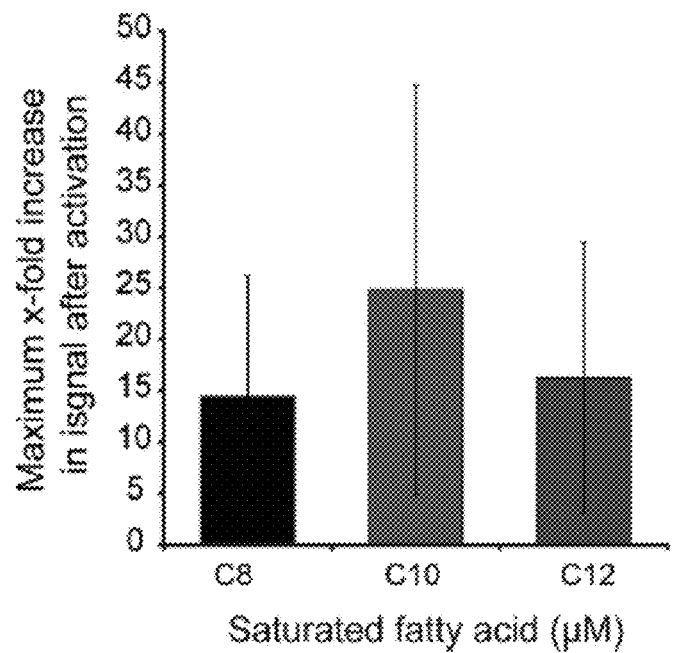
FIG. 11 shows a graph demonstrating GPR40-based sensor maximum x-fold increase in signal after activation with C8 (800 µM), C10 (800 µM) and C12 (250 µM) acids. All experiments were done in triplicate and the error bars represent the standard deviation from the mean. None of the samples shows a statistical difference using a two-tailed t test.

To generate a sensor to detect medium-chain fatty acids Ste2 in the modified yeast strain having deletion of Far1 and Sst2 was replaced with a GPCR known to bind medium-chain fatty acids in mammalian cells and coupled it to the yeast mating pathway with $P_{FIG1}$-GFP as the reporter plasmid, which resulted in GFP fluorescence upon medium-chain fatty acid addition (FIG. 7). The GPCRs tested were the olfactory receptor OR1G1 (Sanz, G., Schlegel, C., Pernollet, J. C., and Briand, L. (2005) Comparison of odorant specificity of two human olfactory receptors from different phylogenetic classes and evidence for antagonism, *Chemical Senses* 30, 69-80) and the free fatty acid receptor GPR40 (Itoh, Y., et al. (2003) Free fatty acids regulate insulin secretion from pancreatic beta cells through GPR40, *Nature* 422, 173-176). First, OR1G1 and GPR40 sensing of even, medium-chain saturated fatty acids (C8-C16) using $P_{FIG1}$-GFP(m) was tested. A reliable signal after fatty acid addition was not observed (FIGS. 23 and 24). Hypothesizing that the large standard deviation of $P_{FIG1}$-GFP(m) contributed to the inability to detect medium-chain fatty acids, $P_{FIG1}$-GFP(s) was tested as the reporter plasmid. Using $P_{FIG1}$-GFP(s) enabled the OR1G1 based-sensor to detect C8, C10 and C12 fatty acids with 13-, 17-, and 13-fold increases in signal after activation, respectively (FIGS. 8-9). Using $P_{FIG1}$-GFP(s) also enabled the GPR40 based-sensor to detect C8, C10 and C12 saturated fatty acids, with 14-, 25-, and 16-fold increases in signal after activation, respectively (FIGS. 10-11). It was also explored whether the OR1G1-based sensor signal could be improved by expressing the OR1G1 from a single-copy (s) rather than a multi-copy (m) plasmid. Results are demonstrated in FIG. 25. OR1G1(m) and OR1G1(s) were observed to have similar increases in signal after activation with 500 µM decanoic acid.

The OR1G1-based sensor signal modification was carried out by using i) the mammalian olfactory $G_\alpha$ subunit ($G_{olf}$) that normally couples to OR1G1 instead of the yeast $G_\alpha$ (GPA1) and ii) a hybrid $G_\alpha$ subunit composed of GPA1 carrying the five C-terminal amino acids from $G_{olf}$—both strategies having been previously successful to link GPCR sensing to the yeast mating pathway. Results are demonstrated in FIG. 26. $G_\alpha$ subunit engineering did not significantly alter the OR1G1-based sensor signal. Using the chromosomal GPA1 resulted in the greatest increase in signal after activation above 250 µM decanoic acid.

Figure 12:
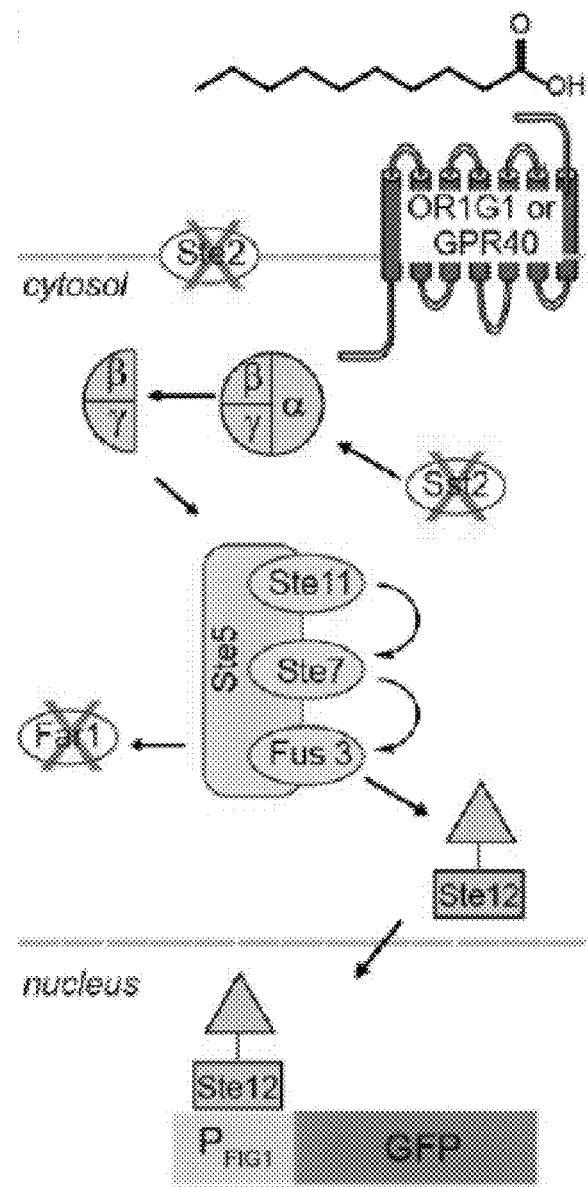
FIG. 12 shows a cartoon of one embodiment of a GPCR-based chemical biosensor having a sensor unit schematic of: chemical sensor strain (W303 Δfar1, Δsst2, Δste2) expressing either OR1G1 or GPR40 carrying PFig1-GFP(s) as the reporter plasmid.
Figure 13:
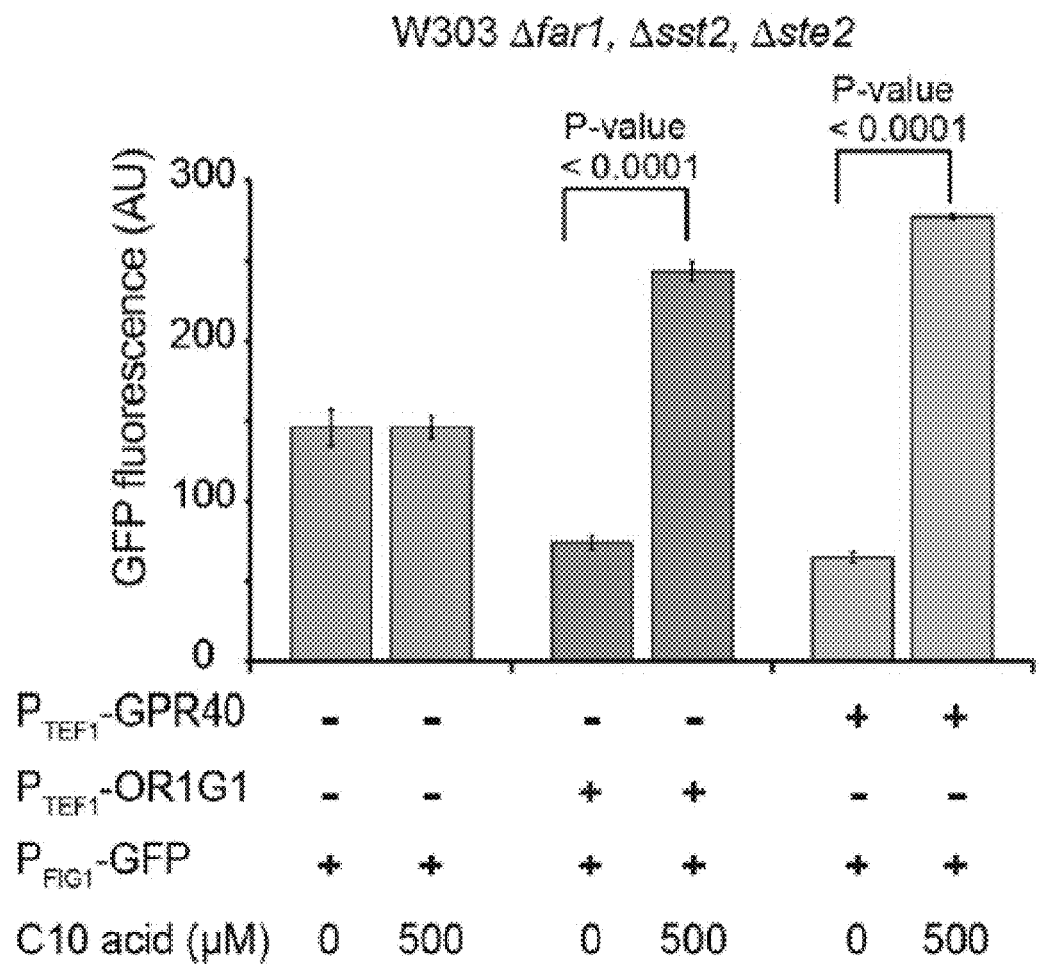
FIG. 13 shows a graph demonstrating that a GPCR-based sensor signal requires a sensing unit (GPCR) for chemical sensing. The chemical sensor strain expresses no GPCR, OR1G1 or GPR40 in the presence of 0 or 500 µM decanoic (C10) acid using PFig1-GFP(s) as the reporter plasmid. All experiments were done in triplicate and the error bars represent the standard deviation from the mean.

To confirm that the medium-chain fatty acids were signalling via the GPCR sensing unit and not through a different cellular mechanism, the chemical sensor strain in the presence and absence of the GPCRs and either 0 or 500 µM decanoic acid was tested (FIG. 12). An increase in GFP fluorescence was only observed in the presence of both 500 µM decanoic acid and either OR1G1 (P-value <0.001) or GPR40 (P-value <0.001) (FIG. 13).

Figure 14:
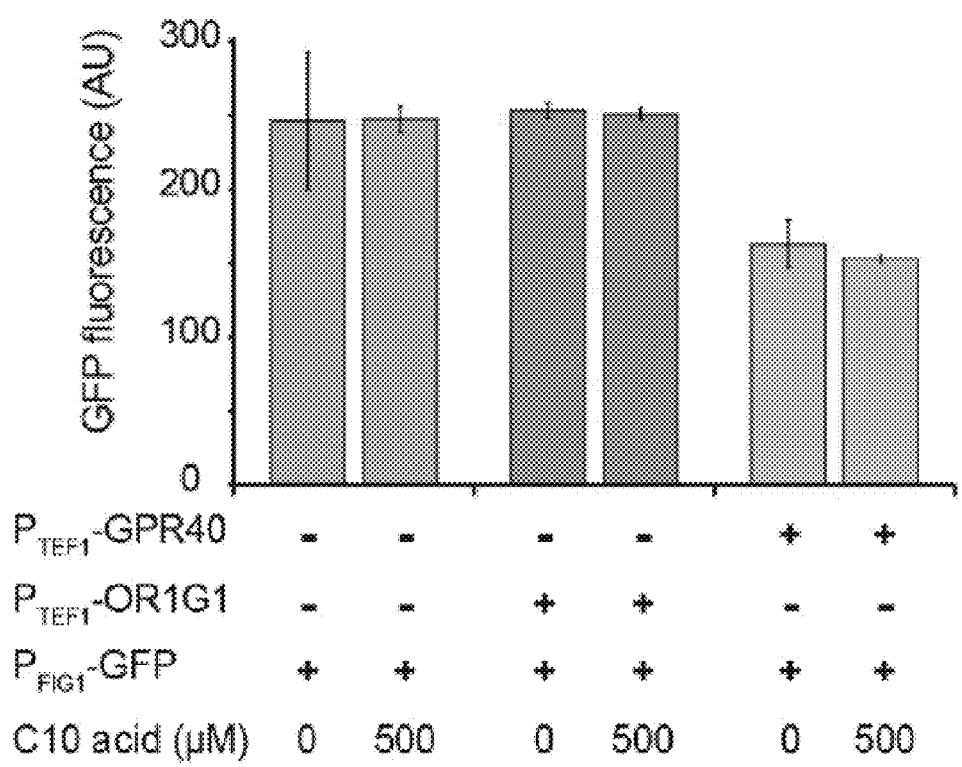
FIG. 14 shows a graph demonstrating that a GPCR-based sensor signal requires response unit (Ste12) for chemical sensing. A chemical sensor strain with endogenous yeast mating pathway transcription factor Ste12 deleted (W303 Δfar1, Δsst2, Δste2, Δste12) expressing no GPCR, OR1G1 or GPR40 in the presence of 0 or 500 μM decanoic (C10) acid using PFig1-GFP(s) as the reporter plasmid. P-values, obtained from a two-tailed t test, are shown for statistically different samples. All experiments were done in triplicate and the error bars represent the standard deviation from the mean.

To demonstrate that the chemical signal was transmitted via the yeast mating pathway, the mating pathway transcription factor Ste12 was deleted. The sensor strain having the three deletions (Far 1, Sst2, and Ste12) was then tested in the presence and absence of the GPCRs and either 0 or 500 µM decanoic acid. There was no observable increase in GFP fluorescence in the absence of Ste12 and the presence of both GPCR and 500 µM decanoic acid (FIG. 14). Interestingly, deletion of Ste12 was observed to produce greater overall GFP background fluorescence, which can be attributed to transcription factors other than Ste12, such as the TATA box binding protein, binding to the pheromone response elements in $P_{Fig1}$-GFP(s). Taken together, these data demonstrate that decanoic acid is sensed by the heterologous GPCR, which uses the yeast mating pathway as the processing unit and not a different cellular mechanism.

To determine the specificity of the OR1G1- and the GPR40-based sensors, we tested the ability of the sensors to detect saturated C8, C10 and C12 fatty aldehydes, important targets for the perfume industry, saturated C8, C10 and C12 fatty alcohols, important targets for the detergent industry, as well as C10 fatty acid methyl- and ethyl-esters, which are advanced biofuels that can serve as replacements for D2 diesel was tested. Results for OR1G1-based sensors are demonstrated in FIGS. 15A-15C. Results for GPR40-sensors are demonstrated in FIGS. 16A-16C. Except for C10 aldehyde, the OR1G1 based-sensor was unable to detect aldehydes, alcohols or esters with more than a 3-fold increase in signal after activation. The GPR40 based-sensor detected the C10 aldehyde at 125 µM and C12 aldehyde at 250 µM, both with a 3-fold increase in signal after activation, but was unable to detect the C8 aldehyde. Similarly to the OR1G1 based-sensor, the GPR40 based-sensor was unable to detect alcohols or esters with more than a 3-fold increase in signal after activation. These data demonstrate that the OR1G1- and GPR40-based sensors are specific to medium chain fatty acids.

Example 2

GPCR-Based Biosensors Containing a Synthetic Response Unit

The biosensors of Example 1 were modified by introducing a synthetic response unit capable of taking information from the yeast mating pathway and exclusively activating green fluorescent protein (GFP) expression, resulting in a decanoic acid sensor with a 30-fold increase in signal after activation. Introduction of the synthetic response unit also altered the linear range of the sensor. To improve the biosensor response to medium-chain fatty acids, the endogenous mating pathway transcription factor Ste12, which activates more than 100 mating pathway genes, was bypassed.

To engineer a system in which medium-chain fatty acid sensing would trigger only GFP transcription, Ste12 was replaced in the yeast strain carrying deletions of Ste2, Sst2, and Far1 with one of two synthetic transcription factors (STFs): 1) STF1, which is composed of the Ste12 phosphorylation domain and the Gal4 activation and DNA binding domains (Pi, H. W., Chien, C. T., and Fields, S. (1997) Transcriptional activation upon pheromone stimulation mediated by a small domain of *Saccharomyces cerevisiae* Ste12p, *Mol Cell Biol* 17, 6410-6418) and 2) STF2, which is composed of the Ste12 phosphorylation domain, the synthetic B42 activation domain and the bacterial LexA DNA binding domain (Golemis, E. A., and Brent, R. (1992) Fused Protein Domains Inhibit DNA-Binding by Lexa, *Mol Cell Biol* 12, 3006-3014 and Peralta-Yahya, P., Carter, B. T., Lin, H. N., Tao, H. Y., and Cornish, V. W. (2008) High-Throughput Selection for Cellulase Catalysts Using Chemical Complementation, *J Am Chem Soc* 130, 17446-17452). STF1 can activate transcription of GFP placed under control of a synthetic minimal promoter carrying five Gal4 DNA binding sites ($P_{Gal4(5\times)}$). STF2 activates transcription of GFP placed under control of a synthetic minimal promoter carrying four lexA DNA binding sites ($P_{LexA(4\times)}$) (FIGS. 17 and 18).

Under glucose conditions, STF1 triggers only $P_{Gal4(5\times)}$-GFP expression as endogenous galactose promoters are repressed by Mig1. STF2 triggers only expression of $P_{LexA(4x)}$-GFP as lexA binding sites are of prokaryotic origin and orthogonal to the yeast machinery. Coupling of the STF1/$P_{Gal4(5\times)}$-GFP response unit to the OR1G1 based-sensor resulted in a 30-fold increase in signal after activation in the presence of 800 µM decanoic acid (FIGS. 19 and 20), which is almost a 200% improvement over the Ste12/$P_{FIG1}$-GFP(s) response unit (Example 1). Further, the OR1G1 based-sensor coupled to the STF1/$P_{Gal4(5\times)}$-GFP response unit also was observed to have an improved linear range, reaching to 500 µM decanoic acid when compared to the OR1G1 based-sensor coupled to the Ste12/$P_{FIG1}$-GFP(s) response unit, in which linear range plateaued at 250 µM decanoic acid. Coupling of the STF2/$P_{LexA(4\times)}$-GFP response unit to the OR1G1 based-sensor resulted in only a 7-fold increase in signal after activation in the presence of 800 µM decanoic acid. Coupling of the STF1/$P_{Gal4(5\times)}$-GFP response unit to the GPR40 based-sensor unit resulted in a 28-fold increase in signal after activation in the presence of 500 µM decanoic acid (FIGS. 21-22), though this increase was not statistically significant when compared to coupling the Ste12/$P_{FIG1}$-GFP(s) response unit to the GPR40-based sensor (25-fold increase). Coupling the GPR40 based-sensor to STF2/$P_{LexA(4x)}$ showed only a 4-fold increase in GFP expression upon decanoic acid exposure.

Example 3

Determining the Dynamic Range of GPCRs of Examples 1 and 2

The linear and dynamic range and linear range, binding affinity and sensitivity of the sensors was evaluated to determine their utility in chemical screening applications. This is believed to be the first report of a whole-cell biosensor for medium-chain fatty acids and the first coupling of a synthetic response unit to a GPCR-based yeast sensor for the sensing of non-endogenous chemicals. The rapid generation of non-invasive chemical sensors such as the ones presented in this work will be important to the future engineering of chemical-producing microbes.

Dose response curves of the GPCR-based sensors in the presence of fatty acids were fitted to the Hill equation (Table 1). Response curves for the OR1G1- and GPR40-based sensors could be fitted to transfer functions for all saturated fatty acids. For the detection of decanoic acid with the OR1G1-based sensor, changing the response unit from Ste12/$P_{FIG1}$-GFP(s) to STF1/$P_{Gal4(5\times)}$-GFP was observed to improve the dynamic range from a 17- to a 30-fold increase, change the linear range from 34-250 µM to 110-500 µM, and increase the $K_M$ from 65 µM to 248 µM. Further, the sensitivity of the response to decanoic acid was also observed to increase from n=2.3 to n=3.2. For the detection of decanoic acid with the GPR40-based sensor, changing the response unit from Ste12/$P_{FIG1}$-GFP(s) to STF1/$P_{Gal4(5x)}$-GFP did not result in a statistically significant change in dynamic range, but was observed to change the linear range from 36-100 µM to 47-250 µM and increase the $K_M$ from 69 µM to 114 µM. Therefore, by simply changing the response unit, the dynamic and linear range of GPCR-based sensors can be altered without the need for using a GPCR with a different binding affinity for the compound of interest. This can be a significant advantage over the modular GPCR system described herein over currently available single component sensor. Sensors with different dynamic and linear ranges may be useful to different applications. For example, when the engineering of a chemical producing microbe is optimized, it can be desirable to have a sensor for different production levels, i.e. one sensor with a linear range from 10-100 uM, another one from 100 to 500 uM, etc.

TABLE 1

| Strain | Reporter plasmid | GPCR | TF | Chemical | GFP max (AU) | Dynamic range | Linear range | $K_M$ (µM) | Hill coeff. (n) |
|---|---|---|---|---|---|---|---|---|---|
| W303 Δfar1, Δsst2 | $P_{Fig1}$-GFP(s) | Ste2 | Ste12 | α factor | 2314 | 40 | 8-50 nM | 0.03 | 1.7 |
| | $P_{Fus1}$-GFP(s) | Ste2 | Ste12 | α factor | 4565 | 20 | 2-25 nM | 0.02 | 1.1 |
| | $P_{Fus1}$-GFP(m) | Ste2 | Ste12 | α factor | 20525 | 24 | 5-25 nM | 0.02 | 1.8 |
| | $P_{Fig1}$-GFP(m) | Ste2 | Ste12 | α factor | 7566 | 68 | 4-25 nM | 0.02 | 1.4 |
| W303 Δfar1, Δsst2 Δste2 | $P_{Fig1}$-GFP(s) | OR1G1 | Ste12 | C8 acid | 239 | 13 | 19-250 µM | 230 | 1.5 |
| | | OR1G1 | Ste12 | C10 acid | 308 | 17 | 34-250 µM | 65 | 2.25 |
| | | OR1G1 | Ste12 | C12 acid | 233 | 13 | 1-250 µM | 50 | 0.85 |
| | $P_{Fig1}$-GFP(s) | GPR40 | Ste12 | C8 acid | 197 | 14 | 36-250 µM | 162 | 2.25 |
| | | GPR40 | Ste12 | C10 acid | 339 | 25 | 36-100 µM | 69 | 4.1 |
| | | GPR40 | Ste12 | C12 acid | 222 | 16 | 2-250 µM | 148 | 0.7 |
| W303 Δfar1, Δsst2, Δste2, Δste12 | $P_{Gal4(5x)}$-GFP(m) | OR1G1 | STF1 | C10 acid | 1126 | 30 | 110-500 µM | 248 | 3.2 |
| | | GPR40 | STF1 | C10 acid | 573 | 28 | 47-250 µM | 114 | 3 |
| | $P_{LexA(4x)}$-GFP(m) | OR1G1 | STF2 | C10 acid | 405 | 7 | 2-100 µM | 69 | 0.62 |
| | | GPR40 | STF2 | C10 acid | 501 | 4 | 4-100 µM | 62 | 0.77 |

In Table 1: $^a$Dose response curves were fitted to the Hill equation to derive the biosensor transfer functions from which the performance features were obtained. TF: transcription factor. GFPmax is the highest fluorescence obtained by the sensor in the presence vs the absence of the chemical. Dynamic range is the ratio of the highest fluorescence obtained by the sensor in the presence vs the absence of the chemical. Linear range is the series of chemical concentrations for which a change in signal can be detected by the sensor. The minimum limit of the linear range is estimated as the chemical concentration corresponding to 10% signal saturation from the fitted model. KM is the chemical concentration at half maximal signal, estimated by linear interpolation from experimental data. Hill coefficient (n) is the sensitivity of the system.

The ability of the OR1G1-GPRC-based biosensors to detect medium-chain fatty acids, such as decanoic acid, contain within a mixture of other fatty acids was evaluated. The results are shown in FIG. 27. The inability for the OR1G1-GPRC-based biosensor to detect decanoic acid in a mixture with C14 and C16 acids may be due to the toxicity of fatty acids to cell growth (see FIGS. 28A-28C). Transforming decanoic acid concentration to titers, the OR1G1-sensor coupled to the Ste12/$P_{FIG1}$-GFP(s) response unit can detect decanoic acid titers from about 6 to about 43 mg/L. The OR1G1-based sensor coupled to the STF1/$P_{Gal4(5\times)}$-GFP response unit to detect decanoic acid titers from about 19 to about 86 mg/L. Since extracellular decanoic acid production in *E. coli* is about 80 mg/L (Choi, Y. J., and Lee, S. Y. (2013) Microbial production of short-chain alkanes, *Nature* 502, 571-574) and *S. cerevisiae*'s is about 3 mg/L (Leber, C., and Da Silva, N. A. (2014) Engineering of *Saccharomyces cerevisiae* for the Synthesis of Short Chain Fatty Acids, *Biotechnol Bioeng* 111, 347-358) the OR1G1 sensor has the appropriate linear range to screen for decanoic acid-producing for microbes with increased titers. In another application, the sensors can be used as a systems biology tools to interrogate less engineered strains for alternative routes to increase fatty acid production in a medium-throughput fashion ($10^3$ samples/day). Such a throughput would allow the screening of entire transposon libraries, or simply existing microbial deletion collections, such as those from *S. cerevisiae* or *E. coli* for the discovery of novel regulatory elements that affect the decanoic acid production.

Example 4

Experimental Methods for Examples 1-3

Yeast Strain Construction.

The yeast haploid strain W303 (MATa, leu2-3, 112 trp1-1 can1-100 ura3-1 ade2-1 his3-11,15) was used in this study. The open reading frames (ORF) of Far1 Sst2, Ste2, and Ste12 were deleted using Delitto perfetto (Storici, F., Lewis, L. K. & Resnick, M. A. In vivo site-directed mutagenesis using oligonucleotides. *Nature biotechnology* 19, 773-776, (2001) and Stuckey, S. & Storici, F. Gene Knockouts, in vivo Site-Directed Mutagenesis and Other Modifications Using the Delitto Perfetto System in *Saccharomyces cerevisiae*. *Method Enzymol* 533, 103-131, (2013)). For all deletions the core cassette CORE-I-SceI containing the I-SceI gene under control of the inducible $P_{GAL1}$ promoter, as well as the hygromycin resistant maker and a counter selectable *K. lactis* URA3 marker gene were used. For W303 Δfar1 the core cassette was amplified from pGSHU with primers KM1/KM2 and used to delete the Far1 ORF. The cassette was subsequently popped out using primers KM7/KM8 to create strain PPY62. For W303 Δfar1, Δsst2, the core cassette was amplified from pGSHU with primers KM9/KM10 and used to delete the Sst2 ORF in PPY62. The cassette was subsequently popped out using primers KM13/KM14 to create strain PPY58. For W303 Δfar1, Δsst2, Δste2, the core cassette was amplified from pGSHU with primers KM59/KM60 and used to delete the Ste2 ORF in PPY58. The cassette was subsequently popped out using primers KM61/KM62 to create strain PPY140. For W303 Δfar1, Δsst2, Δste2, Δste12, KanMX4 was amplified from pFA6a-KanMX4 with primers KM49/KM50 and used to delete the Ste12 ORF in PPY140 to create strain PPY161. Some yeast strains and plasmids used are listed in Table 2. Note-I combined Table 1 from the ACS Synthetic biology 2014 paper with the Table provided in the Supplement of the ACS Synthetic biology 2014 paper in Table 2 below.

TABLE 2

Plasmids and Yeast Strains

| Strain # | Plasmid/base strain where applicable | Description | Reference where applicable |
|---|---|---|---|
| PPY39 | pESC-Leu2 | pESC-Leu2, $P_{Gal1}$, $P_{Gal10}$ | Agilent |
| PPY34 | pESC-His3 | pESC-His3, $P_{Gal1}$, $P_{Gal10}$ | Agilent |
| PPY15 | pRS415-Leu2 | YE-type (episomal) shuttle vector | ATCC |
| PPY13 | pRS413-His3 | YE-type (episomal) shuttle vector | ATCC |
| PPY38 | pGFP | Enhanced GFP | Storici's Lab |
| PPY43 | pKM43 | pESC-Leu2-$P_{Gal1}$-GFP | This study |
| PPY96 | pKM96 | pESC-Leu2-$P_{Fus1}$-GFP | This study |
| PPY97 | pKM97 | pESC-Leu2-$P_{Fig1}$-GFP | This study |
| PPY111 | pKM111 | pESC-His3-$P_{TEF1}$-$P_{ADH1}$ | This study |
| PPY144 | pKM144 | pESC-His3-$P_{TEF1}$-$P_{ADH1}$-STF1 | This study |
| PPY150 | pSTF1 | Commercially synthesized Gal4$_{AD}$-Ste12(P)-Gal4$_{DBD}$ | Pi et al.[4] |
| PPY185 | pOR1G1 | Commercially synthesized GPCR OR1G1 codon optimized for *S. cerevisiae* | This study |
| PPY194 | pSTF2 | Commercially synthesized B42$_{AD}$-Ste12(P)-LexA$_{DBD}$ | This study |
| PPY269 | pKM269 | pESC-His3-$P_{TEF1}$-OR1G1-$P_{ADH1}$ | This study |
| PPY282 | pGPR40 | commercially synthesized GPCR GPR40 codon optimized for *S. cerevisiae* | This study |
| PPY389 | pKM389 | pRS415-Leu2-$P_{Fus1}$-GFP | This study |
| PPY469 | pKM469 | pESC-His3-$P_{TEF1}$-GPR40-$P_{ADH1}$ | This study |

TABLE 2-continued

Plasmids and Yeast Strains

| Strain # | Plasmid/base strain where applicable | Description | Reference where applicable |
|---|---|---|---|
| PPY470 | pG$_{olf}$ | commercially synthesized G$_{olf}$ sequence | This study |
| PPY513 | pKM513 | pESC-His3-P$_{TEF1}$-OR1G1-P$_{ADH1}$-G$_{olf}$ | This study |
| PPY528 | pKM528 | pESC-Leu2-P$_{Gal4(5x)}$-GFP | This study |
| PPY566 | pFA6a-KanMX4 | G418 resistant gene (KanMx4) | Storici's Lab |
| PPY571 | pGSHU | CORE-I-SceI cassette including the I-SceI gene under the inducible GAL1 promoter, the hygromycin resistant gene and counter selectable KlURA3 marker gene | Storici's Lab |
| PPY586 | pKM586 | pRS415-Leu2-P$_{Fig1}$-GFP (s) | This study |
| PPY595 | pKM595 | pESC-His3-P$_{TEF1}$-OR1G1-P$_{ADH1}$-STF1 | This study |
| PPY637 | pGAL4(5x) | Commercially synthesized minimal promoter with five GAL4 DNA binding sites | This study |
| PPY651 | pKM651 | pESC-His3-P$_{TEF1}$-OR1G1-P$_{ADH1}$-Gpa1-G$_{olf}$ | This study |
| PPY684 | pKM684 | pRS413-His3-P$_{Tef1}$-OR1G1 | This study |
| PPY685 | pKM685 | pESC-His3-P$_{TEF1}$-GPR40-P$_{ADH1}$-STF1 | This study |
| PPY686 | pKM686 | pRS413-His3-P$_{TEF1}$-OR1G1-P$_{ADH1}$-Gpa1-G$_{olf}$ | This study |
| PPY690 | pLexA | Commercially synthesized LexA DNA binding sites | This study |
| PPY712 | pKM712 | pESC-Leu2-P$_{LexA(4x)}$-GFP | This study |
| PPY727 | pKM727 | pESC-His3-P$_{TEF1}$-OR1G1-P$_{ADH1}$-STF2 | This study |
| PPY728 | pKM728 | pESC-His3-P$_{TEF1}$-GPR40-P$_{ADH1}$-STF2 | This study |
| PPY11 | W303 | MATa, leu2-3, trp1-1, can1-100, ura3-1, ade2-1, his3-11 | ATCC |
| PPY62 | PPY11 | Δfar1 | This study |
| PPY58 | PPY11 | Δfar1, Δsst2 | This study |
| PPY140 | PPY11 | Δfar1, Δsst2, Δste2 | This study |
| PPY161 | PPY11 | Δfar1, Δsst2, Δste2, Δste12 | This study |
| PPY638 | PPY 58 | pESC-Leu2-PFus1-GFP | This study |
| PPY639 | PPY58 | pESC-Leu2-PFig1-GFP | This study |
| PPY640 | PPY 58 | pRS415-Leu2-PFus1-GFP | This study |
| PPY641 | PPY 58 | pRS415-Leu2-PFig1-GFP | This study |
| PPY653 | PPY 58 | pESC-Leu2 | This study |
| PPY654 | PPY 58 | pRS415-Leu2 | This study |
| PPY643 | PPY140 | pESC-His3-PTEF1-OR1G1, pRS415-Leu2-PFig1-GFP | This study |
| PPY644 | PPY140 | pESC-His3-PTEF1-GPR40, pRS415-Leu2-PFig1-GFP | This study |
| PPY912 | PPY140 | pRS13-His3-PTEF1-OR1G1, pRS415-Leu2-PFig1-GFP | This study |
| PPY913 | PPY140 | pESC-His3-PTEF1-OR1G1-PADH1-Golf, pRS415-Leu2-PFig1-GFP | This study |
| PPY914 | PPY140 | pESC-His3-PTEF1-OR1G1-PADH1-GPA1-Golf, pRS415-Leu2-PFig1-GFP | This study |
| PPY915 | PPY140 | pRS13-His3-PTEF1-OR1G1-PADH1-GPA1-Golf, pRS415-Leu2-PFig1-GFP | This study |
| PPY656 | PPY140 | pESC-His3, pRS415-Leu2 | This study |
| PPY916 | PPY140 | pRS13-His3, pRS415-Leu2 | This study |
| PPY794 | PPY140 | pESC-His3, pRS415-Leu2-PFig1-GFP | This study |
| PPY795 | PPY161 | pESC-His3-PTEF1-OR1G1, pRS415-Leu2-PFig1-GFP | This study |
| PPY832 | PPY161 | pESC-His3-PTEF1-GPR40, pRS415-Leu2-PFig1-GFP | This study |
| PPY657 | PPY161 | pESC-His3, pESC-Leu2 | This study |
| PPY833 | PPY161 | pESC-His3, pRS415-Leu2-PFig1-GFP | This study |
| PPY661 | PPY161 | pESC-His3-PTEF1-OR1G1-PADH1-STF1, pESC-Leu2-PGal4(5x)-GFP | This study |
| PPY818 | PPY161 | pESC-His3-PTEF1-OR1G1-PADH1-STF2, pESC-Leu2-PLexA(4x)-GFP | This study |
| PPY796 | PPY161 | pESC-His3-PTEF1-GPR40-PADH1-STF1, pESC-Leu2, PGal4(5x)-GFP | This study |
| PPY819 | PPY161 | pESC-His3-PTEF1-GPR40-PADH1-STF2, pESC-Leu2-PLexA(4x)-GFP | This study |

Vector Construction.

Enhanced GFP was amplified from pEGFP using primers KM19/KM20 and cloned under $P_{Gal1}$ in pESC-Leu2 at BamHI/HindIII to create pESC-Leu2-$P_{Gal1}$-GFP (pKM43). To construct pESC-Leu2-$P_{Fus1}$-GFP (pKM96) and pESC-Leu2-$P_{Fig1}$-GFP (pKM97), the Fus1 and FIG. 1 promoters were amplified from the W303 genome using primers KM15/KM56 and KM54/KM55, respectively. The Fus1 and Fig1 promoters were cloned into pKM43 at NotI/BamHI. To construct pRS415-Leu2-$P_{Fus1}$-GFP (pKM389) and pRS415-Leu2-$P_{Fig1}$-GFP (pKM586), $P_{Fus1}$-GFP and $P_{Fig1}$-GFP were amplified from the pKM96 or pKM97 using primers KM159/KM160 or KM185/KM186 and cloned into pRS415-Leu2 at HindIII/BamHI. To construct pESC-His3-$P_{Tef1}$-$P_{Adh1}$ (pKM111), the Tef1 and Adh1 promoters were amplified from the W303 yeast genome using primers KM27/KM28 and KM23/24, respectively, and cloned into pESC-His3 at BamHI/NotI using SLIC (Li, M. Z. & Elledge, S. J. Harnessing homologous recombination in vitro to generate recombinant DNA via SLIC. *Nature methods* 4, 251-256, (2007)). To construct pESC-His3-$P_{Tef1}$-GPR40-$P_{Adh1}$ (pKM469), GPR40 was amplified from pGPR40 using primers SB89/SB90 and cloned into pKM111 at BamHI/SacII. To construct pESC-His3-$P_{Tef1}$-OR1G1-$P_{Adh1}$ (pKM269), OR1G1 was amplified from pOR1G1 using primers SB3/SB4 and cloned into pKM111 at BamHI/SacII. To construct pRS413-His3-$P_{Tef1}$-OR1G1 (pKM684) $P_{Tef1}$-OR1G1 was amplified from pKM269 using primers KM251/KM252 and cloned in pRS413-His3 between NotI/BamHI. To construct pESC-His3-$P_{Tef1}$-OR1G1-$P_{Adh1}$-Golf (pKM513) $G_{olf}$ was amplified from p$G_{olf}$ using primers KM245/KM246 and cloned in pKM269 at NotI/SpeI. To construct pESC-His3-$P_{Tef1}$-OR1G1-$P_{Adh1}$-Gpa1-Golf (pKM651) GPA1 was amplified from W303 genomic DNA using primers KM191/KM192 and cloned in pKM269 at NotI/SpeI. To construct pRS413-His3-$P_{Tef1}$-OR1G1-$P_{Adh1}$-Gpa1-Golf (pKM686) $P_{Tef1}$-OR1G1-$P_{Adh1}$-Gpa1-$G_{olf}$ was amplified from pKM651 using primers KM193/KM194 and cloned in pRS413 at NotI/BamHI. To construct pESC-His3-$P_{Tef1}$-$P_{Adh1}$-STF1 (pKM144), STF1 was amplified from pSTF1 using primers KM43/KM44 and cloned into pKM111 at NotI/SpeI. To construct pESC-His3-$P_{Tef1}$-OR1G1-$P_{Adh1}$-STF1 (pKM595) STF1 was amplified from pKM144 using primers KM189/KM190 and cloned in pKM269 at NotI/SpeI. To construct pESC-Leu2-$P_{Gal4(5x)}$-GFP (PPY528), five Gal4 binding sites were amplified from pGal4(5×) using primers KM187/KM188 and cloned into pESC-Leu2 at BamHI/NotI. To construct pESC-His3-$P_{Tef1}$-GPR40-$P_{Adh1}$-STF1 (pKM685) STF1 was amplified from pKM144 using primers KM189/190 and cloned in pKM469 at NotI/SpeI. To construct pESC-His3-$P_{Tef1}$-OR1G1-$P_{Adh1}$-STF2 (pKM727) STF2 was amplified from pSTF2 using primers KM197/KM198 and cloned in pKM269 at NotI/SpeI. To construct pESC-His3-$P_{Tef1}$-GPR40-$P_{Adh1}$-STF2 (pKM728) STF2 was amplified from pSTF2 using primers KM197/KM198 and cloned in pKM269 at NotI/SpeI. To construct pESC-Leu2-$P_{LexA(4x)}$-GFP (pKM712) pLexA was amplified from pLexA using primers KM195/KM196 and cloned in pKM43 at NotI/BamHI. A list of primers and their sequences are shown in Table 3.

TABLE 3

| SEQ ID NO: | Name | Sequence |
|---|---|---|
| 1 | KM1 | GTCTATAGATCCACTGGAAAGCTTCGTGGGCGTAAGAAGGCAAT CTATTATAGGGATAACAGGGTAAT TTCGTACGCTGCAGGTCGAC |
| 2 | KM2 | AAAAAAGGAAAAGCAAAAGCCTCGAAATACGGGCCTCGATTCCC GAACTACCGCGCGTTGGCCGATTCAT |
| 3 | KM7 | CCACTGGAAAGCTTCGTGGGCGTAAGAAGGCAATCTATTATAGT TCGGGAATCGAGGCCCGTATTTCGAGGCTTTTGCTT |
| 4 | KM8 | AAGCAAAAGCCTCGAAATACGGGCCTCGATTCCCGAACTATAAT AGATTGCCTTCTTACGCCCACGAAGCTTTCCAGTGG |
| 5 | KM9 | TATCTGAGGCGTTATAGGTTCAATTTGGTAATTAAAGATAGAGTT GTAAGTAGGGATAACAGGGTAAT TTCGTACGCTGCAGGTCGAC |
| 6 | KM10 | AGGACTGTTTGTGCAATTGTACCTGAAGATGAGTAAGACTCTCAA TGAAACCGCGCGTTGGCCGATTCAT |
| 7 | KM13 | GTTATAGGTTCAATTTGGTAATTAAAGATAGAGTTGTAAGTTTCAT TGAGAGTCTTACTCATCTTCAGGTACAATTGCAC |
| 8 | KM14 | GTGCAATTGTACCTGAAGATGAGTAAGACTCTCAATGAAACTTAC AACTCTATCTTTAATTACCAAATTGAACCTATAAC |
| 9 | KM19 | CGTCAAGGAGAAAAAACCCCGGATCCATGGTGAGCAAGGGCGA GGA |
| 10 | KM20 | TCTTAGCTAGCCGCGGTACCAAGCTTTTACTTGTACAGCTCGTC CA |
| 11 | KM15 | TGTAATCCATCGATACTAGTGCGGCCGCACGATGATTCAGTTCG CCTT |
| 12 | KM23 | TGTAATCCATCGATACTAGTGCGGCCGCTGTATATGAGATAGTT GATT |
| 13 | KM24 | TTTTGAAGCTATGGTGTGTGATCCTTTTGTTGTTTCCGGG |

TABLE 3-continued

| SEQ ID NO: | Name | Sequence |
|---|---|---|
| 14 | KM27 | CCTATAGTGAGTCGTATTACGGATCCTTTGTAATTAAAACTTAGAT |
| 15 | KM28 | AGCTAGCCGCGGTACCAAGC |
| 16 | KM43 | AATCAACTATCTCATATACAGCGGCCGCATGAAGCTACTGTCTTCTAT |
| 17 | KM44 | CATCCTTGTAATCCATCGATACTAGTTTAGAACCCATTATTGTTG |
| 18 | KM49 | CTTTTATAGCGGAACCGCTTTCTTTATTTGAATTGTCTTGTTCACCAAGGATGGGTAAGGAAAAGACTCA |
| 19 | KM50 | CTGGCCCGCATTTTTAATTCTTGTATCATAAATTCAAAAATTATATTATATTAGAAAAACTCATCGAGCA |
| 20 | KM54 | TGTAATCCATCGATACTAGTGCGGCCGCATCACCCTGCATTGCCTCTT |
| 21 | KM55 | TCCTCGCCCTTGCTCACCATGGATCCTTTTTTTTTTTTTTTTGT |
| 22 | KM56 | TCCTCGCCCTTGCTCACCATGGATCCTTTGATTTTCAGAAACTTGA |
| 23 | KM59 | AATTGGTTACTTAAAAATGCACCGTTAAGAACCATATCCAAGAATCAAAATAGGGATAACAGGGTAATTTCGTACGCTGCAGGTCGAC |
| 24 | KM60 | ACCTTATACCGAAGGTCACGAAATTACTTTTTCAAAGCCGTAAATTTTGACCGCGCGTTGGCCGATTCAT |
| 25 | KM61 | TTAAAAATGCACCGTTAAGAACCATATCCAAGAATCAAAATCAAAATTTACGGCTTTGAAAAAGTAATTTCGTGACCTTC |
| 26 | KM62 | GAAGGTCACGAAATTACTTTTTCAAAGCCGTAAATTTTGATTTTGATTCTTGGATATGGTTCTTAACGGTGCATTTTTAA |
| 27 | KM159 | TCGAGGTCGACGGTATCGATAAGCTTACGATGATTCAGTTCGCCTT |
| 28 | KM160 | GCGGCCGCTCTAGAACTAGTGGATCCCTTCGAGCGTCCCAAAACCT |
| 29 | KM185 | CCCCCCTCGAGGTCGACGGTATCGATAAGCTTATCACCCTGCATTG |
| 30 | KM186 | CGCGGTGGCGGCCGCTCTAGAACTAGTGGATCCCTTCGAGCGTCCC |
| 31 | KM187 | TAATCCATCGATACTAGTGCGGCCGCCCGAGCTCTTACGCGGGTCG |
| 32 | KM188 | TCCTCGCCCTTGCTCACCATGGATCCTATATACCCTCTAGAGTCGA |
| 33 | KM189 | CATCCTTGTAATCCATCGATACTAGTTTAGAACCCATTATTGTTGG |
| 34 | KM190 | TCAACTATCTCATATACAGCGGCCGCATGAAGCTACTGTCTTCTAT |
| 35 | KM191 | CATCCTTGTAATCCATCGATACTAGTTCACAACAATTCGTACTGTA |
| 36 | KM192 | TCAACTATCTCATATACAGCGGCCGCATGGGTGTACAGTGAGTAC |
| 37 | KM193 | TCGAATTCCTGCAGCCCGGGGGATCCGAGCGACCTCATGCTATACC |
| 38 | KM194 | TGGAGCTCCACCGCGGTGGCGGCCGCCTTCGAGCGTCCCAAAACCT |
| 39 | KM195 | TAATCCATCGATACTAGTGCGGCCGCCCGAGCTCTTACGCGGGTCG |

TABLE 3-continued

| SEQ ID NO: | Name | Sequence |
|---|---|---|
| 40 | KM196 | TCCTCGCCCTTGCTCACCATGGATCCCATTATATACCCTCTAGAGT |
| 41 | KM197 | CATCCTTGTAATCCATCGATACTAGTTTAAGAGGCATCACCAGACA |
| 42 | KM198 | TCAACTATCTCATATACAGCGGCCGCATGGGTGCTCCACCTAAGAA |
| 43 | KM245 | CATCCTTGTAATCCATCGATACTAGTTTACAACAATTCGTACTGTT |
| 44 | KM246 | TCAACTATCTCATATACAGCGGCCGCATGGGTTGCCTGGGTAATTC |
| 45 | KM251 | TCGAATTCCTGCAGCCCGGGGGATCCCACACACCATAGCTTCAAAA |
| 46 | KM252 | TGGAGCTCCACCGCGGTGGCGGCCGCCTTCGAGCGTCCCAAAACCT |
| 47 | SB3 | ATCTAAGTTTTAATTACAAAGGATCCATGCATCACCATCACCATC |
| 48 | SB4 | TTAGAGCGGATCTTAGCTAGCCGCGGTTATGGGGAATGAATCTTTC |
| 49 | SB89 | TTAGAGCGGATCTTAGCTAGCCGCGGTTACTTTTGAGATTTACCACC |
| 50 | SB90 | TAAGTTTTAATTACAAAGGATCCAAAACAATGGATTTGCCACCACAATT |

Autofluorescense Strains.

For the Ste2p/α-factor sensor, W303 Marl, Asst2 carrying a blank plasmid (pRS15-Leu2) with the same marker and copy number as the reporter plasmid (pRS15-Leu2-$P_{FIG1}$-GFP) was used to measure cell autofluorescence. For the OR1G1- and GPR40-sensors, W303 far1Δ sst2Δ ste2Δ carrying pRS15-Leu2 and a blank plasmid (pESC-His3) with the same marker and copy number as the GPCR plasmid (pESC-His3-$P_{TEF1}$-GPCR) was used. For the synthetic response unit experiments, W303 far1Δ sst2Δ ste12Δ carrying pRS15-Leu2 and pESC-His3 was used.

Biosensing Protocol.

For the Ste2/α-factor sensor, strains PPY638, PPY639, PPY640, PPY641 were grown overnight in synthetic complete media with 2% glucose and lacking leucine (SD glu (L⁻)). The next day, the cells were used to inoculate a 20 mL of SD glu (L⁻) to an $OD_{600}$=0.06 and incubated for 18 hrs at 30° C. (150 r.p.m.). The cells were centrifuged, re-suspended in 5 mL SD glu (L⁻), used to innoculate 5 ml of fresh SD glu (L⁻) to $OD_{600}$=0.6. α-factor (0-100 nM, Zymo Y1001) was added to the medium and incubated for 4 hrs at 30° C. (150 r.p.m.) before reading for cell fluorescence using a flow cytometer. For the OR1G1- and GPR40-based sensors using Ste12/$P_{FIG1}$-GFP response unit, strains PPY643, PPY644 were grown overnight in SD glu and lacking histidine and leucine (SD glu (HL⁻)). The next day, the cells were used to inoculate a 20 mL of SD glu (HL⁻) to an $OD_{600}$=0.06 and incubated for 18 hrs at 15° C. (150 r.p.m.). The cells were centrifuged, re-suspended in 2 ml SD glu (HL⁻) to $OD_{600}$=0.6. C8, C10, C12, C14 and C16 saturated fatty acids (0-800 μM) were added to the medium and incubated for 4 hrs at 30° C. (150 r.p.m.) before reading for cell fluorescence using a flow cytometer. For the OR1G1-based sensor expressed from a single copy plasmid, and when coupled to $G_{olf}$ and GPA1-Golf, strains PPY912, PPY913, PPY914, and PPY915 were processed using the same protocol as the OR1G1-based sensor using Ste12/$P_{FIG1}$-GFP response unit. For the OR1G1- and GPR40 based-sensors with synthetic response units, PPY661, PPY796, PPY818, and PPY819, were processed using the same protocol as the OR1G1- and GPR40 based-sensors using the Ste12/$P_{FIG1}$-GFP response unit. All fatty acids were dissolved in DMSO and the final concentration of DMSO in the cultures was 1%. GFP fluorescence was measured using BD LSRII flow cytometers with the following settings: 488 nM laser line, 515-545 nm filter, FSC: 178 volts, SSC: 122 volts, FITC: 600 volts. Fluorescence data was collected from 10,000 viable cells for each experiment. Flow cytometry histogram analysis was done using FlowJo software.

Statistical Analysis.

For all experiments, cell autofluorescence, measured using the biosensor strain with empty plasmids, was subtracted from the fluorescence of the biosensor at all chemical concentrations to obtain GFP fluorescence attributable to the sensor. Maximum x-fold increase in signal after activation is defined as the quotient of GFP fluorescence in the presence and absence (0 μM) of the chemical. Standard deviation for the X-fold increase in GFP fluorescence was calculated using:

$$\Delta z = z \text{ SQRT } [(\Delta x/x)^2 + (\Delta y/y)^2]$$

where x and Δx are the average fluorescence and standard deviation in the absence of the chemical, respectively, and y and Δy are the average fluorescence and standard deviation in the presence of the chemical, respectively. Z and Δz are x-fold increase in signal activation and its standard deviation, respectively.

Biosensor Performance Calculations.

The Hill equation was used to fit the transfer function to derive the biosensor performance features:

$$GFP = GFP_0 + (GFP_{chemical} - GFP_0)(x^n / K_M^n + x^n)$$

where $GFP_0$ is the fluorescence in the absence of chemical, $GFP_{chemical}$ is the fluorescence in the presence of the chemical, x is the ligand concentration, $K_M$ is the ligand concentration that results in half-maximal signal, and n is a measure of the biosensor sensitivity (Hill coefficient). The $K_M$ value was determined directly from the experimental data while the n value is the best fit to the experimental data using Matlab Curve-Fitting Toolbox and the Hill equation. It was estimated from the fitted model that the substrate concentration corresponded to 10% of signal saturation as the lower bound of the linear range of the sensor.

Example 6

GPCR-Based Biosensors Using a Fast Maturing Fluorescent Reporter Protein

To increase the speed and signal strength of the sensor, a number of different fluorescent proteins that have a faster maturation time and higher intrinsic fluorescence was tested. Five different fluorescent proteins were tested and their activity was measured and in the sensor context and compared it to enhanced GFP (EGFP), which was used previously. Specifically, the superfolder GFP, GFPγ, mCherry, mKate2, and Venus were tested.

Biosensing Protocol

The Ste2/α-factor sensor strain (PPY58) transformed with either plasmids pRP973, pRP974, pRP975, pRP976, pRP977, pRP984, pRP985, or pRP986 were grown overnight in synthetic complete media with 2% glucose and lacking leucine (SD glu (L⁻)). The next day, the cells were used to inoculate a 20 mL of SD glu (L⁻) to an $OD_{600}$=0.06 and incubated for 18 hrs at 30° C. (150 r.p.m.). The cells were centrifuged, re-suspended in 5 mL SD glu (L), and used to innoculate 5 ml of fresh SD glu (L⁻) to $OD_{600}$=0.6. α-factor (100 nM, Zymo Y1001) was added to the medium and incubated for 4 hrs at 30° C. (150 r.p.m.) before reading for cell fluorescence using a flow cytometer.

Vector Construction.

Super folder GFP was amplified from pPPY875 (pFA6-Link-yoSuperfolderGFP-caURA3) using primers RP1/RP2 and cloned under $P_{Fig1}$ in KM97 (pESC-Leu2-$P_{Fig1}$-GFP, multi copy plasmid) at BamHI/HindIII to create pESC-Leu2-$P_{Fig1}$-Superfolder GFP (pRP973). To construct pESC-Leu2-$P_{Fig1}$-Gamma GFP (pRP974), gammaGFP was amplified from pPPY874 (pFA6-Link-yoGammarGFP-spHis5) using primers RP3/RP4 and cloned under and $P_{Fig1}$ in pKM97 at BamHI/HindIII to cerate pESC-Leu2-$P_{Fig1}$-gammaGFP (pRP974). mCherry was amplified from pKM945 using primers RP5/RP6 and cloned under $P_{Fig1}$ in KM97 at BamHI/HindIII to create pESC-Leu2-$P_{Fig1}$-mCherry (pRP975). mKate2 was amplified from pPPY889(pDONR P4-P1R-mKate2) using primers RP7/RP8 and cloned under $P_{Fig1}$ in KM97 at BamHI/HindIII to create pESC-Leu2-$P_{Fig1}$-mKate2 (pRP976). Venus was amplified from pPPY873(pKT0090) using primers RP9/RP10 and cloned under $P_{Fig1}$ in KM97 at BamHI/HindIII to create pESC-Leu2-$P_{Fig1}$-Venus (pRP977).

To clone into pRS415 (single copy plasmid) $P_{Fig1}$-Superfolder GFP was amplified from pRP973 using primers KM296/297 and cloned at BamHI and NotI to create pRS415-Leu2 $P_{Fig1}$-superfolder GFP (pRP984). $P_{Fig1}$-Gamma GFP was amplified from pRP974 using primers KM296/297 and cloned at BamHI and NotI to create pRS415-Leu2-$P_{Fig1}$-gamma GFP (pRP985). $P_{Fig1}$-mKate2 was amplified from pRP976 using primers KM296/297 and cloned at BamHI and NotI to create pRS415-Leu2-$P_{Fig1}$-mKate2 (pRP 986).

TABLE 4

Primers used in example 4

| Primer | SEQ ID NO | Sequence |
| --- | --- | --- |
| RP1 | 76 | ACAAACAAAAAAAAAAAAAAAAAAGGATCCATGACAGTCAACACTAAGAC |
| RP2 | 77 | CGGATCTTAGCTAGCCGCGGTACCAAGCTTTTATAATTGGCCAGTCTTTTTC |
| RP3 | 78 | ACAAACAAAAAAAAAAAAAAAAAAGGATCCATGGGTAGGAGGGCTTTTG |
| RP4 | 79 | CGGATCTTAGCTAGCCGCGGTACCAAGCTTTTACAACACTCCCTTCGTG |
| RP5 | 80 | ACAAACAAAAAAAAAAAAAAAAAAGGATCCATGGTGAGCAAGGGCGAG |
| RP6 | 81 | CGGATCTTAGCTAGCCGCGGTACCAAGCTTTTATAATTTGGACTTGTACAGC |
| RP7 | 82 | ACAAACAAAAAAAAAAAAAAAAAAGGATCCATGGTGAGCGAGCTGATTA |
| RP8 | 83 | CGGATCTTAGCTAGCCGCGGTACCAAGCTTTTATCTGTGCCCCAGTTTG |
| RP9 | 84 | ACAAACAAAAAAAAAAAAAAAAAAGGATCCATGTCTAAAGGTGAAGAATTAT |
| RP10 | 85 | CGGATCTTAGCTAGCCGCGGTACCAAGCTTTTATTTGTACAATTCATCCATAC |
| KM296 | 86 | TCGAATTCCTGCAGCCCGGGGATCCATCACCCTGCATTGCCTCTT |
| KM297 | 87 | TGGAGCTCCACCGCGGTGGCGGCCGCCTTCGAGCGTCCCAAAACCT |
| KM304 | 88 | ACAAAAAAAAAAAAAAAAAGGATCCATGAAAGTCCAAATAACCAA |
| KM305 | 89 | TCTTAGCTAGCCGCGGTACCAAGCTTTCAGGTTGCATCTGGAAGGT |

TABLE 5

Plasmids used in Example 4

| Strains number | Plasmid Name | Copy | Fluorescent Protein | Reference where applicable |
|---|---|---|---|---|
| PPY973 | pRP973 | pESC-Leu2-P$_{Fig1}$-sGFP | Superfolder GFP | This study |
| PPY974 | pRP974 | pESC-Leu2-P$_{Fig1}$-GFPγ | GFPγ | This study |
| PPY975 | pRP975 | pESC-Leu2-P$_{Fig1}$-mCherry | mCherry | This study |
| PPY976 | pRP976 | pESC-Leu2-P$_{Fig1}$-mKate2 | mKate2 | This study |
| PPY977 | pRP977 | pESC-Leu2-P$_{Fig1}$-Venus | Venus | This study |
| PPY984 | pRP984 | pRS-Leu2-P$_{Fig1}$-sGFP | Superfolder GFP | This study |
| PPY985 | pRP985 | pRS-Leu2-P$_{Fig1}$-GFPγ | GFPγ | This study |
| PPY986 | pRP986 | pRS-Leu2-P$_{Fig1}$-mKate2 | mKate2 | This study |

Results are shown in Tables 6 and 7 and FIGS. 31 and 32.

TABLE 6

Brightness of different fluorescent proteins relative to EGFP. The brightness of each fluorescent protein was measured in *S. cerevisiae*.

| Class | Protein | Brightness (% relative to EGFP) | Reference |
|---|---|---|---|
| Far-red | mKate2 | 74 | Shcherbo D., et al. *Biochem. J.* 2009, 418, 567-574. |
| Red | mCherry | 47 | Shaner N C, et al. *Nat. Biotechnol.* 2004, 22, 1567-72. |
| Yellow-green | Venus | | |
| Green | EGFP | 100 | |
| Green | Superfolder GFP | 50 | Lee S, et al. *PloS one* 2013, 8. |
| Green | GFPγ | 155 | Lee S, et al. *PloS one* 2013, 8. |

TABLE 7

Maturation half-time for different fluorescent proteins. The method to measuring maturation time is different for each fluorescent protein.

| Protein | Maturation t$_{0.5}$ (min) | Organism (measured) | Reference |
|---|---|---|---|
| mKate2 | <20 | *E. coli* | Shcherbo D., et al. *Biochem. J.* 2009, 418, 567-574. |
| mCherry | 16.9-30.3 | *S. cerevisiae* | Khmelinskii A, et al. *Nat. Biotechnol.* 2012, 30, 708-14. |
| Venus | 11.2 ± 1.6 | *S. cerevisiae* | Ball, David A., et al. *PloS ONE* 2014, 9, e107087. |
| EGFP | 60 | *E. coli* | Sniegowski, J. A. et al. *Biochem. Biophys. Res. Commun.* 2005, 332, 657-663. |

TABLE 7-continued

Maturation half-time for different fluorescent proteins. The method to measuring maturation time is different for each fluorescent protein.

| Protein | Maturation t$_{0.5}$ (min) | Organism (measured) | Reference |
|---|---|---|---|
| Superfolder GFP GFPγ | 5.63 ± 0.82 | *S. cerevisiae* | Khmelinskii A, et al. *Nat. Biotechnol.* 2012, 30, 708-14. |

Example 7

GPCR-Based Biosensors Having Amplified Signals

To increase the signal by the sensor upon chemical (e.g. decanoic acid) addition, the transcription factor (e.g. Ste12) that gets activated by the signaling cascade (e.g. yeast mating pathway) and results in the transcription activation of a fluorescent protein (e.g. GFP) and fluorescence, also drives the expression of the transcription activation (e.g. Ste12) itself, resulting in a feed forward loop and signal amplification. The plasmid for this feed forward set up (PESC-P$_{Fig1}$-Ste12) was constructed. Ste12 was amplified from W303 genomic DNA using primers KM304/KM305 and cloned under P$_{Fig1}$ in pKM97 at BamHI and HindIII to create pESC-Leu2-P$_{Fig1}$-Ste12 (pKM1000).

Example 8

Repression of Response Unit Signaling in Response to Chemical Stimulus

Briefly, the yeast biosensor was configured to contain a PlexA(4x) repressor and STF2 utilizing the MAPK signaling cascade. The signaling molecule was a GFP and signal in response to exposing the biosensor to varying concentrations of decanoic acid was evaluated.

Example 9

Screening of Olfactory GPCRs for Use in GPCR-Based Biosensors

The OR1G1 GPCR that has been used to demonstrate sensing of decanoic acid was used to generate seven saturation mutagenesis libraries around the active site with the goal of engineering this sensor to bind different biofuel molecules. The GPCR libraries are being screened with different GPCR-based biosensors configured to detect biofuel and/or components thereof. Below is a sequence obtained when one of the libraries was tested against ethyl decanoate.

Below are the sequence modifications in the 7 saturation mutagenesis libraries using the GPCR OR1 G1 as the starting GPCR scaffold:

Library 1: Met 81, Pro 183, Asp 259, and Val 276
Library 2: Phe 104, Leu 110, Pro 183, Val 276
Library 3: Lys 80, Phe 104, Leu 184, Phe 256
Library 4: Met 105, Val 108, Phe 256, Val 276
Library 5: Met 105, Ser 255, Phe 256, Val 276
Library 6: Lys 80, Met 81, Asn 84, Gln 100
Library 7: Asp 191, Ser 255, Phe 256, Asp 259

OR1G1 wild type sequence

SEQ ID NO: 59

ATGCATCACCATCACCATCACGAAGGTAAGAATTTGACCTCTATTTCCGAGTGTTTCTTACT

TGGTTTCTCCGAACAATTGGAAGAACAGAAGCCATTGTTCGGTTCCTTCCTGTTTATGTACT

```
TGGTCACCGTCGCTGGTAACTTGTTAATCATATTAGTCATTATTACCGATACCCAGTTACAT

ACCCCAATGTATTTCTTCTTGGCTAACTTATCCCTAGCTGACGCTTGTTTCGTTTCCACTAC

CGTCCCAAAGATGTTGGCTAACATTCAAATTCAATCCCAAGCTATTTCCTACTCCGGTTGTT

TATTGCAATTGTACTTCTTTATGTTGTTCGTTATGTTGGAGGCTTTCTTGTTGGCTGTTATGG

CTTACGATTGCTACGTCGCTATTTGTCATCCATTGCATTACATCTTGATTATGTCCCCAGGT

TTGTGTATCTTCTTAGTCTCCGCCTCCTGGATTATGAACGCTTTGCATTCCTTGTTGCATAC

CTTGTTAATGAACTCTTTATCCTTCTGTGCTAACCACGAAATTCCACATTTCTTTTGTGATAT

TAACCCATTGTTGTCCTTGTCCTGTACCGATCCATTCACCAACGAATTGGTTATCTTCATTA

CCGGTGGTTTGACTGGTTTGATTTGTGTCTTGTGTTTGATTATCTCCTACACTAACGTCTTC

TCCACCATTTTGAAAATTCCATCCGCTCAAGGTAAAAGAAAAGCATTCTCCACCTGTTCCTC

CCATTTGTCCGTTGTCTCCTTGTTCTTTGGTACCTCATTCTGTGTCGATTTCTCTTCCCCATC

CACTCATTCCGCTCAAAAGGATACCGTTGCTTCCGTTATGTACACCGTCGTCACTCCAATG

TTGAATCCATTTATTTATTCCTTAAGAAATCAAGAAATTAAGTCCTCCTTGAGAAAGTTGATT

TGGGTTAGAAAGATTCATTCCCCATAA

>A2 hit (nucleotide sequence)
                                                           SEQ ID NO: 60
ATGCATCACCATCACCATCACGAAGGTAAGAATTTGACCTCTATTTCCGAGTGTTTCTTACT

TGGTTTCTCCGAACAATTGGAAGAACAGAAGCCATTGTTCGGTTCCTTCCTGTTTATGTACT

TGGTCACCGTCGCTGGTAACTTGTTAATCATATTAGTCATTATTACCGATACCCAGTTACAT

ACCCCAATGTATTTCTTCTTGGCTAACTTATCCCTAGCTGACGCTTGTTTCGTTTCCACTAC

CGTCCCAAAGTCTTTGGCTAACATTCAAATTCAATCCCAAGCTATTTCCTACTCCGGTTGTT

TATTGCAATTGTACTTCTTTATGTTGTTCGTTATGTTGGAGGCTTTCTTGTTGGCTGTTATGG

CTTACGATTGCTACGTCGCTATTTGTCATCCATTGCATTACATCTTGATTATGTCCCCAGGT

TTGTGTATCTTCTTAGTCTCCGCCTCCTGGATTATGAACGCTTTGCATTCCTTGTTGCATAC

CTTGTTAATGAACTCTTTATCCTTCTGTGCTAACCACGAAATTCCACATTTCTTTTGTGATAT

TAACGTGTTGTTGTCCTTGTCCTGTACCGATCCATTCACCAACGAATTGGTTATCTTCATTA

CCGGTGGTTTGACTGGTTTGATTTGTGTCTTGTGTTTGATTATCTCCTACACTAACGTCTTC

TCCACCATTTTGAAAATTCCATCCGCTCAAGGTAAAAGAAAAGCATTCTCCACCTGTTCCTC

CCATTTGTCCGTTGTCTCCTTGTTCTTTGGTACCTCATTCTGTGTCGGCTTCTCTTCCCCAT

CCACTCATTCCGCTCAAAAGGATACCGTTGCTTCCACTATGTACACCGTCGTCACTCCAAT

GTTGAATCCATTTATTTATTCCTTAAGAAATCAAGAAATTAAGTCCTCCTTGAGAAAGTTGAT

TTGGGTTAGAAAGATTCATTCCCCATAA

>A2 hit (amino acid sequence)
                                                           SEQ ID NO: 61
MHHHHHHEGKNLTSISECFLLGFSEQLEEQKPLFGSFLFMYLVTVAGNLLIILVIITDTQ

LHTPMYFFLANLSLADACFVSTTVPKSLANIQIQSQAISYSGCLLQLYFFMLFVMLEAFL

LAVMAYDCYVAICHPLHYILIMSPGLCIFLVSASWIMNALHSLLHTLLMNSLSFCANHEI

PHFFCDINVLLSLSCTDPFTNELVIFITGGLTGLICVLCLIISYTNVFSTILKIPSAQGK

RKAFSTCSSHLSVVSLFFGTSFCVGFSSPSTHSAQKDTVASTMYTVVTPMLNPFIYSLRN

QEIKSSLRKLIWVRKIHSP
```

-continued

J6 (no mutations)
SEQ ID NO: 62
ATGCATCACCATCACCATCACGAAGGTAAGAATTTGACCTCTATTTCCGAGTGTTTCTTACT

TGGTTTCTCCGAACAATTGGAAGAACAGAAGCCATTGTTCGGTTCCTTCCTGTTTATGTACT

TGGTCACCGTCGCTGGTAACTTGTTAATCATATTAGTCATTATTACCGATACCCAGTTACAT

ACCCCAATGTATTTCTTCTTGGCTAACTTATCCCTAGCTGACGCTTGTTTCGTTTCCACTAC

CGTCCCAAAGATGTTGGCTAACATTCAAATTCAATCCCAAGCTATTTCCTACTCCGGTTGTT

TATTGCAATTGTACTTCTTTATGTTGTTCGTTATGTTGGAGGCTTTCTTGTTGGCTGTTATGG

CTTACGATTGCTACGTCGCTATTTGTCATCCATTGCATTACATCTTGATTATGTCCCCAGGT

TTGTGTATCTTCTTAGTCTCCGCCTCCTGGATTATGAACGCTTTGCATTCCTTGTTGCATAC

CTTGTTAATGAACTCTTTATCCTTCTGTGCTAACCACGAAATTCCACATTTCTTTTGTGATAT

TAACCCATTGTTGTCCTTGTCCTGTACCGATCCATTCACCAACGAATTGGTTATCTTCATTA

CCGGTGGTTTGACTGGTTTGATTTGTGTCTTGTGTTTGATTATCTCCTACACTAACGTCTTC

TCCACCATTTTGAAAATTCCATCCGCTCAAGGTAAAAGAAAAGCATTCTCCACCTGTTCCTC

CCATTTGTCCGTTGTCTCCTTGTTCTTTGGTACCTCATTCTGTGTCGATTTCTCTTCCCCATC

CACTCATTCCGCTCAAAAGGATACCGTTGCTTCCGTTATGTACACCGTCGTCACTCCAATG

TTGAATCCATTTATTTATTCCTTAAGAAATCAAGAAATTAAGTCCTCCTTGAGAAAGTTGATT

TGGGTTAGAAAGATTCATTCCCCATAA

J8 (no mutations)
SEQ ID NO: 63
ATGCATCACCATCACCATCACGAAGGTAAGAATTTGACCTCTATTTCCGAGTGTTTCTTACT

TGGTTTCTCCGAACAATTGGAAGAACAGAAGCCATTGTTCGGTTCCTTCCTGTTTATGTACT

TGGTCACCGTCGCTGGTAACTTGTTAATCATATTAGTCATTATTACCGATACCCAGTTACAT

ACCCCAATGTATTTCTTCTTGGCTAACTTATCCCTAGCTGACGCTTGTTTCGTTTCCACTAC

CGTCCCAAAGATGTTGGCTAACATTCAAATTCAATCCCAAGCTATTTCCTACTCCGGTTGTT

TATTGCAATTGTACTTCTTTATGTTGTTCGTTATGTTGGAGGCTTTCTTGTTGGCTGTTATGG

CTTACGATTGCTACGTCGCTATTTGTCATCCATTGCATTACATCTTGATTATGTCCCCAGGT

TTGTGTATCTTCTTAGTCTCCGCCTCCTGGATTATGAACGCTTTGCATTCCTTGTTGCATAC

CTTGTTAATGAACTCTTTATCCTTCTGTGCTAACCACGAAATTCCACATTTCTTTTGTGATAT

TAACCCATTGTTGTCCTTGTCCTGTACCGATCCATTCACCAACGAATTGGTTATCTTCATTA

CCGGTGGTTTGACTGGTTTGATTTGTGTCTTGTGTTTGATTATCTCCTACACTAACGTCTTC

TCCACCATTTTGAAAATTCCATCCGCTCAAGGTAAAAGAAAAGCATTCTCCACCTGTTCCTC

CCATTTGTCCGTTGTCTCCTTGTTCTTTGGTACCTCATTCTGTGTCGATTTCTCTTCCCCATC

CACTCATTCCGCTCAAAAGGATACCGTTGCTTCCGTTATGTACACCGTCGTCACTCCAATG

TTGAATCCATTTATTTATTCCTTAAGAAATCAAGAAATTAAGTCCTCCTTGAGAAAGTTGATT

TGGGTTAGAAAGATTCATTCCCCATAA

L3 C10EE 4
SEQ ID NO: 64
ATGCATCACCATCACCATCACGAAGGTAAGAATTTGACCTCTATTTCCGAGTGTTTCTTACT

TGGTTTCTCCGAACAATTGGAAGAACAGAAGCCATTGTTCGGTTCCTTCCTGTTTATGTACT

TGGTCACCGTCGCTGGTAACTTGTTAATCATATTAGTCATTATTACCGATACCCAGTTACAT

ACCCCAATGTATTTCTTCTTGGCTAACTTATCCCTAGCTGACGCTTGTTTCGTTTCCACTAC

CGTCCCAAAGATGTTGGCTAACATTCAAATTCAATCCCAAGCTATTTCCTACTCCGGTTGTT

-continued

TATTGCAATTGTACTTCTTTTGCTTGTTCGTTATGTTGGAGGCTTTCTTGTTGGCTGTTATGG

CTTACGATTGCTACGTCGCTATTTGTCATCCATTGCATTACATCTTGATTATGTCCCCAGGT

TTGTGTATCTTCTTAGTCTCCGCCTCCTGGATTATGAACGCTTTGCATTCCTTGTTGCATAC

CTTGTTAATGAACTCTTTATCCTTCTGTGCTAACCACGAAATTCCACATTTCTTTTGTGATAT

TAACCCATTGTTGTCCTTGTCCTGTACCGATCCATTCACCAACGAATTGGTTATCTTCATTA

CCGGTGGTTTGACTGGTTTGATTTGTGTCTTGTGTTTGATTATCTCCTACACTAACGTCTTC

TCCACCATTTTGAAAATTCCATCCGCTCAAGGTAAAAGAAAAGCATTCTCCACCTGTTCCTC

CCATTTGTCCGTTGTCTCCTTGTTCTTTGGTACCCTCACTTGTGTCGATTTCTCTTCCCCAT

CCACTCATTCCGCTCAAAAGGATACCGTTGCTTCCTATATGTACACCGTCGTCACTCCAAT

GTTGAATCCATTTATTTATTCCTTAAGAAATCAAGAAATTAAGTCCTCCTTGAGAAAGTTGAT

TTGGGTTAGAAAGATTCATTCCCCATAA

L3 C12EE 5 (97 by insertion)

SEQ ID NO: 65

ATGCATCACCATCACCATCACGAAGGTAAGAATTTGACCTCTATTTCCGAGTGTTTCTTACT

TGGTTTCTCCGAACAATTGGAAGAACAGAAGCCATTGTTCGGTTCCTTCCTGTTTATGTACT

TGGTCACCGTCGCTGGTAACTTGTTAATCATATTAGTCATTATTACCGATACCCAGTTACAT

ACCCCAATGTATTTCTTCTTGGCTAACTTATCCCTAGCTGACGCTTGTTTCGTTTCCACTAC

CGTCCCAAAGATGTTGGCTAACATTCAAATTCAATCCCAAGCTATTTCCTACTCCGGTTGTT

TATTGCAATGTACTTCAACATGTTGTTCGTTATGTTGGAGGCTTTCTTGTTGGCTGTTATGG

CTTACGATTGCTACGTCGCTATTTGTCATCCATTGCATTACATCTTGATTATGTCCCCAGGT

TTGTGTATCTTCTTAGTCTCCGCCTCCTGGATTATGAACGCTTTGCATTCCTTGTTGCATAC

CTTGTTAATGAACTCTTTATCCTTCTGTGCTAACCACGAAATTCCACATTTCTTTTGTGATAT

TAACCCATAGTTGTCCTTGTCCTGTACCGATCCATTCACCAACGAATTGGTTATCTTCATTA

CCGGTGGTTTGACTGGTTTGATTTGTGTCTTGTGTTTGATTATCTCCTACACTAACGTCTTC

TCCACCATTTTGAAAATTCCATCCGCTCAAGGTAAAAGAAAAGCATTCTCCACCTGTTCCTC

CCATTTGTCCGTTGTCTCCTTGTTCTTTGGTACCTCAGACTGTGTCGATTTCTCTTCCCCAT

CCACTCATTCCGCTAAAGGATACCGTTGCTTCCCCATTTGTCCGTTGTCTCCTTGTTCTTTG

GTACCTCACGCTGTGTCGATTTCTCTTCCCCATCCACTCATTCCGCTCAAAAGGATACCGTT

GCTTCCGTTATGTACACCGTCGTCACTCCAATGTTGAATCCATTTATTTATTCCTTAAGAAAT

CAAGAAATTAAGTCCTCCTTGAGAAAGTTGATTTGGGTTAGAAAGATTCATTCCCCATAA

L3 C12EE 6 (97bp insertion)

SEQ ID NO: 66

ATGCATCACCATCACCATCACGAAGGTAAGAATTTGACCTCTATTTCCGAGTGTTTCTTACT

TGGTTTCTCCGAACAATTGGAAGAACAGAAGCCATTGTTCGGTTCCTTCCTGTTTATGTACT

TGGTCACCGTCGCTGGTAACTTGTTAATCATATTAGTCATTATTACCGATACCCAGTTACAT

ACCCCAATGTATTTCTTCTTGGCTAACTTATCCCTAGCTGACGCTTGTTTCGTTTCCACTAC

CGTCCCAAAGATGTTGGCTAACATTCAAATTCAATCCCAAGCTATTTCCTACTCCGGTTGTT

TATTGCAATGTACTTCAACATGTTGTTCGTTATGTTGGAGGCTTTCTTGTTGGCTGTTATGG

CTTACGATTGCTACGTCGCTATTTGTCATCCATTGCATTACATCTTGATTATGTCCCCAGGT

TTGTGTATCTTCTTAGTCTCCGCCTCCTGGATTATGAACGCTTTGCATTCCTTGTTGCATAC

CTTGTTAATGAACTCTTTATCCTTCTGTGCTAACCACGAAATTCCACATTTCTTTTGTGATAT

TAACCCATAGTTGTCCTTGTCCTGTACCGATCCATTCACCAACGAATTGGTTATCTTCATTA

CCGGTGGTTTGACTGGTTTGATTTGTGTCTTGTGTTTGATTATCTCCTACACTAACGTCTTC

-continued

TCCACCATTTTGAAAATTCCATCCGCTCAAGGTAAAAGAAAAGCATTCTCCACCTGTTCCTC

CCATTTGTCCGTTGTCTCCTTGTTCTTTGGTACCTCAGACTGTGTCGATTTCTCTTCCCCAT

CCACTCATTCCGCTAAAGGATACCGTTGCTTCCCCATTTGTCCGTTGTCTCCTTGTTCTTTG

GTACCTCACGCTGTGTCGATTTCTCTTCCCCATCCACTCATTCCGCTCAAAAGGATACCGTT

GCTTCCGTTATGTACACCGTCGTCACTCCAATGTTGAATCCATTTATTTATTCCTTAAGAAAT

CAAGAAATTAAGTCCTCCTTGAGAAAGTTGATTTGGGTTAGAAAGATTCATTCCCCATAA

L5 C10ME 2

SEQ ID NO: 67

ATGCATCACCATCACCATCACGAAGGTAAGAATTTGACCTCTATTTCCGAGTGTTTCTTACT

TGGTTTCTCCGAACAATTGGAAGAACAGAAGCCATTGTTCGGTTCCTTCCTGTTTATGTACT

TGGTCACCGTCGCTGGTAACTTGTTAATCATATTAGTCATTATTACCGATACCCAGTTACAT

ACCCCAATGTATTTCTTCTTGGCTAACTTATCCCTAGCTGACGCTTGTTTCGTTTCCACTAC

CGTCCCAAAGATGTTGGCTAACATTCAAATTCAATCCCAAGCTATTTCCTACTCCGGTTGTT

TATTGCAATTGTACTTCTTTCCCTTGTTCGTTATGTTGGAGGCTTTCTTGTTGGCTGTTATGG

CTTACGATTGCTACGTCGCTATTTGTCATCCATTGCATTACATCTTGATTATGTCCCCAGGT

TTGTGTATCTTCTTAGTCTCCGCCTCCTGGATTATGAACGCTTTGCATTCCTTGTTGCATAC

CTTGTTAATGAACTCTTTATCCTTCTGTGCTAACCACGAAATTCCACATTTCTTTTGTGATAT

TAACCCATTGTTGTCCTTGTCCTGTACCGATCCATTCACCAACGAATTGGTTATCTTCATTA

CCGGTGGTTTGACTGGTTTGATTTGTGTCTTGTGTTTGATTATCTCCTACACTAACGTCTTC

TCCACCATTTTGAAAATTCCATCCGCTCAAGGTAAAAGAAAAGCATTCTCCACCTGTTCCTC

CCATTTGTCCGTTGTCTCCTTGTTCTTTGGTACCCACCTTTGTGTCGATTTCTCTTCCCCAT

CCACTCATTCCGCTCAAAAGGATACCGTTGCTTCCTAGATGTACACCGTCGTCACTCCAAT

GTTGAATCCATTTATTTATTCCTTAAGAAATCAAGAAATTAAGTCCTCCTTGAGAAAGTTGAT

TTGGGTTAGAAAGATTCATTCCCCATAA

L5 C10ME 3

SEQ ID NO: 68

ATGCATCACCATCACCATCACGAAGGTAAGAATTTGACCTCTATTTCCGAGTGTTTCTTACT

TGGTTTCTCCGAACAATTGGAAGAACAGAAGCCATTGTTCGGTTCCTTCCTGTTTATGTACT

TGGTCACCGTCGCTGGTAACTTGTTAATCATATTAGTCATTATTACCGATACCCAGTTACAT

ACCCCAATGTATTTCTTCTTGGCTAACTTATCCCTAGCTGACGCTTGTTTCGTTTCCACTAC

CGTCCCAAAGATGTTGGCTAACATTCAAATTCAATCCCAAGCTATTTCCTACTCCGGTTGTT

TATTGCAATTGTACTTCTTTGTCTTGTTCGTTATGTTGGAGGCTTTCTTGTTGGCTGTTATGG

CTTACGATTGCTACGTCGCTATTTGTCATCCATTGCATTACATCTTGATTATGTCCCCAGGT

TTGTGTATCTTCTTAGTCTCCGCCTCCTGGATTATGAACGCTTTGCATTCCTTGTTGCATAC

CTTGTTAATGAACTCTTTATCCTTCTGTGCTAACCACGAAATTCCACATTTCTTTTGTGATAT

TAACCCATTGTTGTCCTTGTCCTGTACCGATCCATTCACCAACGAATTGGTTATCTTCATTA

CCGGTGGTTTGACTGGTTTGATTTGTGTCTTGTGTTTGATTATCTCCTACACTAACGTCTTC

TCCACCATTTTGAAAATTCCATCCGCTCAAGGTAAAAGAAAAGCATTCTCCACCTGTTCCTC

CCATTTGTCCGTTGTCTCCTTGTTCTTTGGTACCCAGGATTGTGTCGATTTCTCTTCCCCAT

CCACTCATTCCGCTCAAAAGGATACCGTTGCTTCCTCGATGTACACCGTCGTCACTCCAAT

GTTGAATCCATTTATTTATTCCTTAAGAAATCAAGAAATTAAGTCCTCCTTGAGAAAGTTGAT

TTGGGTTAGAAAGATTCATTCCCCATAA

-continued

L5 C10ME 4

SEQ ID NO: 69

ATGCATCACCATCACCATCACGAAGGTAAGAATTTGACCTCTATTTCCGAGTGTTTCTTACT

TGGTTTCTCCGAACAATTGGAAGAACAGAAGCCATTGTTCGGTTCCTTCCTGTTTATGTACT

TGGTCACCGTCGCTGGTAACTTGTTAATCATATTAGTCATTATTACCGATACCCAGTTACAT

ACCCCAATGTATTTCTTCTTGGCTAACTTATCCCTAGCTGACGCTTGTTTCGTTTCCACTAC

CGTCCCAAAGATGTTGGCTAACATTCAAATTCAATCCCAAGCTATTTCCTACTCCGGTTGTT

TATTGCAATTGTACTTCTTTGTCTTGTTCGTTATGTTGGAGGCTTTCTTGTTGGCTGTTATGG

CTTACGATTGCTACGTCGCTATTTGTCATCCATTGCATTACATCTTGATTATGTCCCCAGGT

TTGTGTATCTTCTTAGTCTCCGCCTCCTGGATTATGAACGCTTTGCATTCCTTGTTGCATAC

CTTGTTAATGAACTCTTTATCCTTCTGTGCTAACCACGAAATTCCACATTTCTTTTGTGATAT

TAACCCATTGTTGTCCTTGTCCTGTACCGATCCATTCACCAACGAATTGGTTATCTTCATTA

CCGGTGGTTTGACTGGTTTGATTTGTGTCTTGTGTTTGATTATCTCCTACACTAACGTCTTC

TCCACCATTTTGAAAATTCCATCCGCTCAAGGTAAAAGAAAAGCATTCTCCACCTGTTCCTC

CCATTTGTCCGTTGTCTCCTTGTTCTTTGGTACCGCGGCTTGTGTCGATTTCTCTTCCCCAT

CCACTCATTCCGCTCAAAAGGATACCGTTGCTTCCAATATGTACACCGTCGTCACTCCAAT

GTTGAATCCATTTATTTATTCCTTAAGAAATCAAGAAATTAAGTCCTCCTTGAGAAAGTTGAT

TTGGGTTAGAAAGATTCATTCCCCATAA

L5 C10ME 6

SEQ ID NO: 70

ATGCATCACCATCACCATCACGAAGGTAAGAATTTGACCTCTATTTCCGAGTGTTTCTTACT

TGGTTTCTCCGAACAATTGGAAGAACAGAAGCCATTGTTCGGTTCCTTCCTGTTTATGTACT

TGGTCACCGTCGCTGGTAACTTGTTAATCATATTAGTCATTATTACCGATACCCAGTTACAT

ACCCCAATGTATTTCTTCTTGGCTAACTTATCCCTAGCTGACGCTTGTTTCGTTTCCACTAC

CGTCCCAAAGATGTTGGCTAACATTCAAATTCAATCCCAAGCTATTTCCTACTCCGGTTGTT

TATTGCAATTGTACTTCTTTATCTTGTTCGTTATGTTGGAGGCTTTCTTGTTGGCTGTTATGG

CTTACGATTGCTACGTCGCTATTTGTCATCCATTGCATTACATCTTGATTATGTCCCCAGGT

TTGTGTATCTTCTTAGTCTCCGCCTCCTGGATTATGAACGCTTTGCATTCCTTGTTGCATAC

CTTGTTAATGAACTCTTTATCCTTCTGTGCTAACCACGAAATTCCACATTTCTTTTGTGATAT

TAACCCATTGTTGTCCTTGTCCTGTACCGATCCATTCACCAACGAATTGGTTATCTTCATTA

CCGGTGGTTTGACTGGTTTGATTTGTGTCTTGTGTTTGATTATCTCCTACACTAACGTCTTC

TCCACCATTTTGAAAATTCCATCCGCTCAAGGTAAAAGAAAAGCATTCTCCACCTGTTCCTC

CCATTTGTCCGTTGTCTCCTTGTTCTTTGGTACCGCGGCTTGTGTCGATTTCTCTTCCCCAT

CCACTCATTCCGCTCAAAAGGATACCGTTGCTTCCAGGATGTACACCGTCGTCACTCCAAT

GTTGAATCCATTTATTTATTCCTTAAGAAATCAAGAAATTAAGTCCTCCTTGAGAAAGTTGAT

TTGGGTTAGAAAGATTCATTCCCCATAA

L5 C10ME 7

SEQ ID NO: 71

ATGCATCACCATCACCATCACGAAGGTAAGAATTTGACCTCTATTTCCGAGTGTTTCTTACT

TGGTTTCTCCGAACAATTGGAAGAACAGAAGCCATTGTTCGGTTCCTTCCTGTTTATGTACT

TGGTCACCGTCGCTGGTAACTTGTTAATCATATTAGTCATTATTACCGATACCCAGTTACAT

ACCCCAATGTATTTCTTCTTGGCTAACTTATCCCTAGCTGACGCTTGTTTCGTTTCCACTAC

CGTCCCAAAGATGTTGGCTAACATTCAAATTCAATCCCAAGCTATTTCCTACTCCGGTTGTT

TATTGCAATTGTACTTCTTTACCTTGCGTTATGTTGGAGGCTTTCTTGTTGGCTGTTATGGC

-continued

```
TTACGATTGCTACGTCGCTATTTGTCATCCATTGCATTACATCTTGATTATGTCCCCAGGTTT
GTGTATCTTCTTAGTCTCCGCCTCCTGGATTATGAACGCTTTGCATTCCTTGTTGCATACCT
TGTTAATGAACTCTTTATCCTTCTGTGCTAACCACGAAATTCCACATTTCTTTTGTGATATTA
ACCCATTGTTGTCCTTGTCCTGTACCGATCCATTCACCAACGAATTGGTTATCTTCATTACC
GGTGGTTTGACTGGTTTGATTTGTGTCTTGTGTTTGATTATCTCCTACACTAACGTCTTCTC
CACCATTTTGAAAATTCCATCCGCTCAAGGTAAAAGAAAAGCATTCTCCACCTGTTCCTCCC
ATTTGTCCGTTGTCTCCTTGTTCTTTGGTACCTTCACGTGTGTCGATTTCTCTTCCCCATCC
ACTCATTCCGCTCAAAAGGATACCGTTGTTCCAATATGTACACCGTCGTCACTCCAATGTTG
AATCCATTTATTTATTCCTTAAGAAATCAAGAAATTAAGTCCTCCTTGAGAAAGTTGATTTGG
GTTAGAAAGATTCATTCCCCATAA
```

L6 isobutanol 10

SEQ ID NO: 72
```
ATGCATCACCATCACCATCACGAAGGTAAGAATTTGACCTCTATTTCCGAGTGTTTCTTACT
TGGTTTCTCCGAACAATTGGAAGAACAGAAGCCATTGTTCGGTTCCTTCCTGTTTATGTACT
TGGTCACCGTCGCTGGTAACTTGTTAATCATATTAGTCATTATTACCGATACCCAGTTACAT
ACCCCAATGTATTTCTTCTTGGCTAACTTATCCCTAGCTGACGCTTGTTTCGTTTCCACTAC
CGTCCCAAAGATTTGGCTGTCATTCAAATTCAATCCCAAGCTATTTCCTACTCCGGTTGTTT
ATTGAATTTGTACTTCTTTATGTTGTTCGTTATGTTGGAGGCTTTCTTGTTGGCTGTTATGGC
TTACGATTGCTACGTCGCTATTTGTCATCCATTGCATTACATCTTGATTATGTCCCCAGGTTT
GTGTATCTTCTTAGTCTCCGCCTCCTGGATTATGAACGCTTTGCATTCCTTGTTGCATACCT
TGTTAATGAACTCTTTATCCTTCTGTGCTAACCACGAAATTCCACATTTCTTTTGTGATATTA
ACCCATTGTTGTCCTTGTCCTGTACCGATCCATTCACCAACGAATTGGTTATCTTCATTACC
GGTGGTTTGACTGGTTTGATTTGTGTCTTGTGTTTGATTATCTCCTACACTAACGTCTTCTC
CACCATTTTGAAAATTCCATCCGCTCAAGGTAAAAGAAAAGCATTCTCCACCTGTTCCTCCC
ATTTGTCCGTTGTCTCCTTGTTCTTTGGTACCTCATTCTGTGTCGATTTCTCTTCCCCATCCA
CTCATTCCGCTCAAAAGGATACCGTTGCTTCCGTTATGTACACCGTCGTCACTCCAATGTT
GAATCCATTTATTTATTCCTTAAGAAATCAAGAAATTAAGTCCTCCTTGAGAAAGTTGATTTG
GGTTAGAAAGATTCATTCCCCATAA
```

L6 isobutanol 12

SEQ ID NO: 73
```
ATGCATCACCATCACCATCACGAAGGTAAGAATTTGACCTCTATTTCCGAGTGTTTCTTACT
TGGTTTCTCCGAACAATTGGAAGAACAGAAGCCATTGTTCGGTTCCTTCCTGTTTATGTACT
TGGTCACCGTCGCTGGTAACTTGTTAATCATATTAGTCATTATTACCGATACCCAGTTACAT
ACCCCAATGTATTTCTTCTTGGCTAACTTATCCCTAGCTGACGCTTGTTTCGTTTCCACTAC
CGTCCCAAAGAAGTTGGCTATGATTCAAATTCAATCCCAAGCTATTTCCTACTCCGGTTGTT
TATTGTAGTTGTACTTCTTTATGTTGTTCGTTATGTTGGAGGCTTTCTTGTTGGCTGTTATGG
CTTACGATTGCTACGTCGCTATTTGTCATCCATTGCATTACATCTTGATTATGTCCCCAGGT
TTGTGTATCTTCTTAGTCTCCGCCTCCTGGATTATGAACGCTTTGCATTCCTTGTTGCATAC
CTTGTTAATGAACTCTTTATCCTTCTGTGCTAACCACGAAATTCCACATTTCTTTGATATTAA
CCCATTGTTGTCCTTGTCCTGTACCGATCCATTCACCAACGAATTGGTTATCTTCATTACCG
GTGGTTTGACTGGTTTGATTTGTGTCTTGTGTTTGATTATCTCCTACACTAACGTCTTCTCCA
CCATTTTGAAAATTCCATCCGCTCAAGGTAAAAGAAAAGCATTCTCCACCTGTTCCTCCCAT
```

-continued

TTGTCCGTTGTCTCCTTGTTCTTTGGTACCTCATTCTGTGTCGATTTCTCTTCCCCATCCACT

CATTCCGCTCAAAAGGATACCGTTGCTTCCGTTATGTACACCGTCGTCACTCCAATGTTGA

ATCCATTTATTTATTCCTTAAGAAATCAAGAAATTAAGTCCTCCTTGAGAAAGTTGATTTGGG

TTAGAAAGATTCATTCCCCATAA

L7 C10EE 6 (no mutations)

SEQ ID NO: 74

ATGCATCACCATCACCATCACGAAGGTAAGAATTTGACCTCTATTTCCGAGTGTTTCTTACT

TGGTTTCTCCGAACAATTGGAAGAACAGAAGCCATTGTTCGGTTCCTTCCTGTTTATGTACT

TGGTCACCGTCGCTGGTAACTTGTTAATCATATTAGTCATTATTACCGATACCCAGTTACAT

ACCCCAATGTATTTCTTCTTGGCTAACTTATCCCTAGCTGACGCTTGTTTCGTTTCCACTAC

CGTCCCAAAGATGTTGGCTAACATTCAAATTCAATCCCAAGCTATTTCCTACTCCGGTTGTT

TATTGCAATTGTACTTCTTTATGTTGTTCGTTATGTTGGAGGCTTTCTTGTTGGCTGTTATGG

CTTACGATTGCTACGTCGCTATTTGTCATCCATTGCATTACATCTTGATTATGTCCCCAGGT

TTGTGTATCTTCTTAGTCTCCGCCTCCTGGATTATGAACGCTTTGCATTCCTTGTTGCATAC

CTTGTTAATGAACTCTTTATCCTTCTGTGCTAACCACGAAATTCCACATTTCTTTTGTGATAT

TAACCCATTGTTGTCCTTGTCCTGTACCGATCCATTCACCAACGAATTGGTTATCTTCATTA

CCGGTGGTTTGACTGGTTTGATTTGTGTCTTGTGTTTGATTATCTCCTACACTAACGTCTTC

TCCACCATTTTGAAAATTCCATCCGCTCAAGGTAAAAGAAAAGCATTCTCCACCTGTTCCTC

CCATTTGTCCGTTGTCTCCTTGTTCTTTGGTACCTCATTCTGTGTCGATTTCTCTTCCCCATC

CACTCATTCCGCTCAAAAGGATACCGTTGCTTCCGTTATGTACACCGTCGTCACTCCAATG

TTGAATCCATTTATTTATTCCTTAAGAAATCAAGAAATTAAGTCCTCCTTGAGAAAGTTGATT

TGGGTTAGAAAGATTCATTCCCCATAA

L7 C10EE 9

SEQ ID NO: 75

ATGCATCACCATCACCATCACGAAGGTAAGAATTTGACCTCTATTTCCGAGTGTTTCTTACT

TGGTTTCTCCGAACAATTGGAAGAACAGAAGCCATTGTTCGGTTCCTTCCTGTTTATGTACT

TGGTCACCGTCGCTGGTAACTTGTTAATCATATTAGTCATTATTACCGATACCCAGTTACAT

ACCCCAATGTATTTCTTCTTGGCTAACTTATCCCTAGCTGACGCTTGTTTCGTTTCCACTAC

CGTCCCAAAGATGTTGGCTAACATTCAAATTCAATCCCAAGCTATTTCCTACTCCGGTTGTT

TATTGCAATTGTACTTCTTTATGTTGTTCGTATGTTGGAGGCTTTCTTGTTGGCTGTTATGGC

TTACGATTGCTACGTCGCTATTTGTCATCCATTGCATTACATCTTGATTATGTCCCCAGGTTT

GTGTATCTTCTTAGTCTCCGCCTCCTGGATTATGAACGCTTTGCATTCCTTGTTGCATACCT

TGTTAATGAACTCTTTATCCTTCTGTGCTAACCACGAAATTCCACATTTCTTTTGTGATATTA

ACCCATTGTTGTCCTTGTCCTGTACCTCTCCATTCACCAACGAATTGGTTATCTTCATTACC

GGTGGTTTGACTGGTTTGATTTGTGTCTTGTGTTTGATTATCTCCTACACTAACGTCTTCTC

CACCATTTTGAAAATTCCATCCGCTCAAGGTAAAAGAAAAGCATTCTCCACCTGTTCCTCCC

ATTTGTCCGTTGTCTCCTTGTTCTTTGGTACCCCGAAGTGTGTCGCCTTCTCTTCCCCATCC

ACTCATTCCGCTCAAAAGGATACCGTTGCTTCCGTTATGTACACCGTCGTCACTCCAATGTT

GAATCCATTTATTTATTCCTTAAGAAATCAAGAAATTAAGTCCTCCTTGAGAAAGTTGATTTG

GGTTAGAAAGATTCATTCCCCATAA

We claim:

1. An engineered yeast cell comprising:
   a sensing unit, the sensing unit comprising:
   a G-protein coupled receptor (GPCR);
   a synthetic processing unit, the synthetic processing unit comprising:
   a signal transduction pathway, wherein the signal transduction pathway comprises a synthetic transcription factor selected from the group consisting of STF1, STF2, SFT3 and combinations thereof; and
   a synthetic response unit, the synthetic response unit comprising:
   a recombinant signal molecule gene, where the recombinant signal molecule gene is operatively coupled to a synthetic promoter that is responsive to the synthetic processing unit, wherein the synthetic promoter is selected from the group consisting of: pGAL45x, pLExA4x, pCRE, and combinations thereof,
   wherein the sensing unit is in biologic communication with the processing unit and the processing unit is in biologic communication with the response unit.

2. The engineered yeast cell of claim 1, wherein the GPCR is capable of binding a medium chain fatty acid.

3. The engineered yeast cell of claim 1, wherein the GPCR is an olfactory GPCR.

4. The engineered yeast cell of claim 1, further comprising an amplification unit, wherein the amplification unit is biologically coupled to the response unit.

5. The engineered yeast cell of claim 1, wherein the synthetic transcription factor has a sequence that is about 90%-100% identical to any one of SEQ ID NOs: 51-53.

6. The engineered yeast cell of claim 1, wherein the synthetic promoter has a sequence that is about 90% to 100% identical to any one of SEQ ID NOs: 54-56.

7. The engineered yeast cell of claim 1, wherein the recombinant signal molecule gene is a gene encoding a fluorescent protein.

8. The engineered yeast cell of claim 1, wherein the yeast cell has at least a ste12 deletion.

9. The engineered yeast cell of claim 1, wherein the recombinant signal molecule gene is a biosynthetic gene.

10. The engineered yeast cell of claim 1, wherein the synthetic transcription factor is STF1 and the synthetic promoter is pGAL45x.

11. The engineered yeast cell of claim 10, wherein STF1 has a sequence that is about 90%-100% identical to SEQ ID NO: 51 and pGAL45x has a sequence that is about 90%-100% identical to SEQ ID NO: 54.

12. The engineered yeast cell of claim 1, wherein the synthetic transcription factor is STF2 and the synthetic promoter is pLexA4x.

13. The engineered yeast cell of claim 12, wherein STF2 has a sequence that is about 90%-100% identical to SEQ ID NO: 52 and pGAL45x has a sequence that is about 90%-100% identical to SEQ ID NO: 55.

14. The engineered yeast cell of claim 1, wherein the synthetic transcription factor is STF3 and the synthetic promoter is pCRE.

15. The engineered yeast cell of claim 14, wherein STF3 has a sequence that is about 90%-100% identical to SEQ ID NO: 53 and pCRE has a sequence that is about 90%-100% identical to SEQ ID NO: 56.

16. A method comprising:
   contacting an engineered yeast cell with a sample, wherein the yeast cell comprises
   a sensing unit, the sensing unit comprising:
   a G-protein coupled receptor (GPCR);
   a synthetic processing unit, the synthetic processing unit comprising:
   a signal transduction pathway, wherein the signal transduction pathway comprises a synthetic transcription factor selected from the group consisting of STF1, STF2, SFT3 and combinations thereof; and
   a synthetic response unit, the synthetic response unit comprising:
   a recombinant signal molecule gene, wherein the recombinant signal molecule gene is operatively coupled to a synthetic promoter that is responsive to the synthetic processing unit, wherein the synthetic promoter is selected from the group consisting of: pGAL45x, pLExA4x, pCRE, and combinations thereof, wherein the sensing unit is in biologic communication with the processing unit and the processing unit is in biologic communication with the response unit.

17. The method of claim 16, wherein the step of contacting the engineered yeast cell with a sample further comprises incubating the engineered yeast cell with a biofuel producing cell.

18. The method of claim 16, wherein the synthetic transcription factor is STF1 and the synthetic promoter is pGAL45x.

19. The method of claim 16, wherein the synthetic transcription factor is SFT2 and the synthetic promoter is pLexA4x.

20. The method of claim 16, wherein the synthetic transcription factor is SFT3 and the synthetic promoter is pCRE.

* * * * *